US007754424B1

(12) United States Patent
Ryan

(10) Patent No.: US 7,754,424 B1
(45) Date of Patent: Jul. 13, 2010

(54) ISOLATED GENOMIC POLYNUCLEOTIDE FRAGMENTS FROM CHROMOSOME 12 THAT ENCODE HUMAN CARBOXYPEPTIDASE M AND THE HUMAN MOUSE DOUBLE MINUTE 2 HOMOLOG

(75) Inventor: James W. Ryan, Augusta, GA (US)

(73) Assignee: Ryogen LLC

( * ) Notice: Subject to any disclaimer, the term of this patent is extended or adjusted under 35 U.S.C. 154(b) by 0 days.

(21) Appl. No.: 10/608,463

(22) Filed: Jun. 27, 2003

(51) Int. Cl.
*C12Q 1/68* (2006.01)
*C07H 21/02* (2006.01)

(52) U.S. Cl. ......................................... 435/6; 536/23.1

(58) Field of Classification Search ................ 536/23.2, 536/23.5, 24.1, 24.31, 23.1; 435/6
See application file for complete search history.

(56) References Cited

U.S. PATENT DOCUMENTS 5,411,860 A * 5/1995 Vogelstein et al. ............. 435/6
6,184,212 B1 * 2/2001 Miraglia et al. ............... 514/44

OTHER PUBLICATIONS

Muzny et al. (Mar. 9, 2000) GenBank accession AC025423.*
Kinzler (Mar. 24, 1999) GenBank accession NM_002392.*
Sigalas et al. (1996) Nature medicine, vol. 2, pp. 912-917.*
Watson et al. Recombinant DNA (1992). Published by Scientific American Books, 2nd edition, NY, USA, pp. 137-138.*
Andersen et al., 1996, Mammalian Genome 7:780-783.
Bureau et al., 1995, Genomics 28:109-112.
Ries et al., 2000, Cell 103: 321-330.
Rehli et al., 1995, J. Biol. Chem. 270: 15644-15649.
Oliner et al., 1992, Nature 358:80-83.
Tan et al., 1989, J. Biol. Chem. 264: 13165-13170.

* cited by examiner

*Primary Examiner*—Tekchand Saidha
(74) *Attorney, Agent, or Firm*—Cheryl H. Agris

(57) ABSTRACT

The invention is directed to isolated genomic polynucleotide fragments that encode human carboxypeptidase M and human mouse double minute 2 homolog, vectors and hosts containing these fragments and fragments hybridizing to non-coding regions as well as antisense oligonucleotides to these fragments. The invention is further directed to methods of using these fragments to obtain human carboxypeptidase M and human mouse double minute 2 homolog and to diagnose, treat, prevent and/or ameliorate a pathological disorder.

13 Claims, No Drawings

SEQUENCE LISTING

```
<160> NUMBER OF SEQ ID NOS: 4

<210> SEQ ID NO 1
<211> LENGTH: 443
<212> TYPE: PRT
<213> ORGANISM: Homo sapiens

<400> SEQUENCE: 1

Met Asp Phe Pro Cys Leu Trp Leu Gly Leu Leu Leu Pro Leu Val Ala
1               5                   10                  15

Ala Leu Asp Phe Asn Tyr His Arg Gln Glu Gly Met Glu Ala Phe Leu
            20                  25                  30

Lys Thr Val Ala Gln Asn Tyr Ser Ser Val Thr His Leu His Ser Ile
        35                  40                  45

Gly Lys Ser Val Lys Gly Arg Asn Leu Trp Val Leu Val Val Gly Arg
    50                  55                  60

Phe Pro Lys Glu His Arg Ile Gly Ile Pro Glu Phe Lys Tyr Val Ala
65                  70                  75                  80

Asn Met His Gly Asp Glu Thr Val Gly Arg Glu Leu Leu Leu His Leu
                85                  90                  95

Ile Asp Tyr Leu Val Thr Ser Asp Gly Lys Asp Pro Glu Ile Thr Asn
            100                 105                 110

Leu Ile Asn Ser Thr Arg Ile His Ile Met Pro Ser Met Asn Pro Asp
        115                 120                 125

Gly Phe Glu Ala Val Lys Lys Pro Asp Cys Tyr Tyr Ser Ile Gly Arg
    130                 135                 140

Glu Asn Tyr Asn Gln Tyr Asp Leu Asn Arg Asn Phe Pro Asp Ala Phe
145                 150                 155                 160

Glu Tyr Asn Asn Val Ser Arg Gln Pro Glu Thr Val Ala Val Met Lys
                165                 170                 175

Trp Leu Lys Thr Glu Thr Phe Val Leu Ser Ala Asn Leu His Gly Gly
            180                 185                 190

Ala Leu Val Ala Ser Tyr Pro Phe Asp Asn Gly Val Gln Ala Thr Gly
        195                 200                 205

Ala Leu Tyr Ser Arg Ser Leu Thr Pro Asp Asp Asp Val Phe Gln Tyr
    210                 215                 220

Leu Ala His Thr Tyr Ala Ser Arg Asn Pro Asn Met Lys Lys Gly Asp
225                 230                 235                 240

Glu Cys Lys Asn Lys Met Asn Phe Pro Asn Gly Val Thr Asn Gly Tyr
                245                 250                 255

Ser Trp Tyr Pro Leu Gln Gly Gly Met Gln Asp Tyr Asn Tyr Ile Trp
            260                 265                 270

Ala Gln Cys Phe Glu Ile Thr Leu Glu Leu Ser Cys Cys Lys Tyr Pro
        275                 280                 285
```

-continued

```
Arg Glu Glu Lys Leu Pro Ser Phe Trp Asn Asn Asn Lys Ala Ser Leu
    290                 295                 300

Ile Glu Tyr Ile Lys Gln Val His Leu Gly Val Lys Gly Gln Val Phe
305                 310                 315                 320

Asp Gln Asn Gly Asn Pro Leu Pro Asn Val Ile Val Glu Val Gln Asp
                325                 330                 335

Arg Lys His Ile Cys Pro Tyr Arg Thr Asn Lys Tyr Gly Glu Tyr Tyr
            340                 345                 350

Leu Leu Leu Leu Pro Gly Ser Tyr Ile Ile Asn Val Thr Val Pro Gly
        355                 360                 365

His Asp Pro His Ile Thr Lys Val Ile Ile Pro Glu Lys Ser Gln Asn
    370                 375                 380

Phe Ser Ala Leu Lys Lys Asp Ile Leu Leu Pro Phe Gln Gly Gln Leu
385                 390                 395                 400

Asp Ser Ile Pro Val Ser Asn Pro Ser Cys Pro Met Ile Pro Leu Tyr
                405                 410                 415

Arg Asn Leu Pro Asp His Ser Ala Ala Thr Lys Pro Ser Leu Phe Leu
            420                 425                 430

Phe Leu Val Ser Leu Leu His Ile Phe Phe Lys
        435                 440


<210> SEQ ID NO 2
<211> LENGTH: 491
<212> TYPE: PRT
<213> ORGANISM: Homo sapiens

<400> SEQUENCE: 2

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
```

```
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
        355                 360                 365

Asp Ser Arg Glu Ser Cys Val Glu Glu Asn Asp Asp Lys Ile Thr Gln
    370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
        435                 440                 445

Cys Ile Val His Gly Lys Thr Gly His Leu Met Ala Cys Phe Thr Cys
    450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490


<210> SEQ ID NO 3
<211> LENGTH: 99680
<212> TYPE: DNA
<213> ORGANISM: Homo sapiens

<400> SEQUENCE: 3

taattacaac tttaaacacc aaaccacagt catgttggca ctcagaattt gaatccttat      60

ctactgggct ccagaatctg tactttttaa tttatttact tatttctgag acagggtttt     120

gctccgttgc ttagactaaa gtgctgtggt acaatcacgg cttactgcag ccttgacctc     180

ccgggctcaa gcgatcctct tgcctcagcc ccctgagtag ctgggaccac aggtgtgtgc     240

caccatgccc aactaatttt tgtatttttt gtacagatga gctttcgcca tgttggctag     300

gctggtattg aacttctaga ctcaagtgat ccacccacct cagcctccca aagtgctagg     360

attacaggtg tgagcccaga atctgtactt ctaacaacaa aaatagtttc taatacatac     420

aaaatacttg ataggcctga tggaggataa aggaattaat aaagtatatt ttgtgtcctc     480

cgggagctta ccatttagtg gaggaaatat gtattcccac aaataactgt ggggcaccaa     540
```

-continued

```
gttatgagta cttttacctc cactccaatc tgccactggc tactgagcaa tggtccaagg    600
ttagagcatc atatttagcc atagtataca ttggcatgct tactgggttg tgtggcagca    660
ataaatggca actgaaccaa aagatgcagg agtctagcaa gactttttac ttctggagca    720
atttcaggct tccaaatcct tactgaatta cccttaattg caatttctcg tattactgag    780
atgatgagag tctaatcatt gagactattt cctcctaact ttgttgctat atgcaggcaa    840
ccaagcttca ttctgactgg gggttacgct aacttggatt ttaaaaccca attctgcagt    900
tcaagagaga tgataaatgg agtagaggga cctcctccct accctccccc caaaaccccc    960
aaagccttcc caactcccta tatactctaa aagacagaca ctagaaacta aacaacacat   1020
aatctgatgg gctgatcaat aatgcattgg ttttattacc tgaatatttt ggggttactt   1080
tttcatgtca gtctctcatg tcaaaaattc tcatttccct aatgcctacc ccctcaggcc   1140
ctcatctctc ttccatcttc ctcacgaatg ataatttaag gtcataaaac agatagcttc   1200
acactttcaa tataaactcc aaaaaataaa ttgttagcgg tatttatctg acccctatat   1260
tctagctatt atagtcagat aataaaatcc agggtgctcg agggaacaga tcaaggggac   1320
agttagaaaa cttaagcttc agtgtttctg ttgactctag aaaggcaaaa ctaaaataac   1380
tcatctgtag cctgaatatc attcccaata ggagttagat aaaagcctat cttggcaaag   1440
ctcaaagtcc ttaaagtttg ggtcttattt gtttgtttgt tagactattt tggatcttga   1500
gagtttgctt tgggatgggg aacagctatt agagctgttt ggcgagtggg tatgctagaa   1560
atgggttgaa attatgacat tagtataaat ttttataaaa atctaatttc tagactgggc   1620
aacatagcaa gaccttgtct ctactaaaat aaaaaaaaat tttaaaaaag ctggccatgg   1680
tggcacacac ctgtagtccc agctacttcg ggggctgagg cagtaggagc ccttaagcct   1740
gggaagtcaa ggttgcagtc agccctgatt gtgcaactgc attccagcct gggcaacaga   1800
acaagaccct gtctcaaaaa aaataataat aaataaaatt agtcattata taaaaattct   1860
ttcttttctt tttttttttt tgagacagag tcttactctg ttgcccaggc tggagtgcaa   1920
tggcgcgatc tcagctcact gcaagctccg cctcccaggt tcaagtgatt cttctgcctc   1980
agcctcctga gtagctggga ttacaggtgc atgccaccat gcctggctat ttttcatatt   2040
tttagtagag atatggtttt gccatgttgg ccaggctggt cttgaactcc tgatttcagg   2100
tgatctatgt gtcttggcct cccaaagtgc tgggattaca ggcatgagcc attgcacccg   2160
gcctcaaaat tatttctaat gtgtgcaaag atatctgata aaaactacat gactatgtaa   2220
aataaaacat actatttcct ctgcctggac tttctatttc ttcacccttc aagttacagc   2280
ttaaacagat ccatcttctg gaagcttttt tgaactccac ttaactccat ttcaactcaa   2340
tgagcacctt ctgtgctctt gaatgcaggt ttctgatgac tttggaggtt gtgccactgg   2400
aatagaggga aaaaacttct aggactttca tggagagctt atgtgttcat gaatattgag   2460
cagaacagga gttatttgca tggactgagc aaacagaaga ccaaaataat ctttttatga   2520
ttttttgctt aaaacgttgc ttattctttg tgtttttcag agtcaagaaa actttttttat   2580
ttggagctat ttacagcttt taacaactga gtaaaataca ctccagtgag caaattttgg   2640
agcgcatttc tttctctcta ccttatttct ctgtaatttg gaaactatgt ctacgtatac   2700
ttaatttatg gtagtatcgc tatttgcata agttcagtaa gcatctgttt tcttttgtaa   2760
caggacacta ttagagacac tagttatttt accaaggctt tgactggaat gacatgtttt   2820
cagacttttc agactgcttt gaggaattga ggttgagcta cagagctgat aaaaattcct   2880
tggaaaaact ggccaccttg tttttacaag gttcccaacc tgtggtaagt aaaaatgtcc   2940
```

-continued

```
ctttctgata ggcctaggaa tcccaagtta ttttggtacc tctagaaatg aggaattcat   3000
tcaattcata caggtatctg caggcacaaa taaatctttg gctgggctca agatgctttt   3060
aaaaggtcta atctgagatt ccttattaaa aaaacatcca gcaaagccaa tttttttaaaa   3120
aggcctatat agcaaataat tattcatgtt atgtttcatg caaacaatta ggcctagtat   3180
aaataaaacc aaagcttatt ttgcaaataa attggtcctg ctatgatttg tctttggtaa   3240
aaatggggga aaactggaga gggaaaaatt atgtttcaaa aaaaacctat agcatgcctg   3300
ttattagatt ctagccttgg ctgggcacag tggctcacac ctgtaatccc aacattttga   3360
gaggccgagg caggaggatg aatcacttga gcccagaagt tcgagaccag cctgggcaac   3420
atagggagac cccatctcta caaaaaaatta tttaaaaatt agctgggtgt ggtggtgcac   3480
acctgtagtc ccagctactt ggaaggctga gatggcagga tcactttagc cctagaggtc   3540
gaggcttcag tgagctctga tcatgccact gcactccagc ctgggcaaca gagtgagaca   3600
ctgtctcaaa aaaaaaaaaa aaaaaaaaaa agaaagaaag aaaagaaaag aaaaaaattc   3660
tagccttgtc cattgtttgt gagcctatac taatgactca catctgattg gttcttgggg   3720
atatttacct gaatccctca aggcttcaga tcagttctgc aaggactcct gaagctaaga   3780
ctttcacacc ttgcattagg tctcttgtag tttactgttc tcttaagtgc tatactaacg   3840
atgtggataa gaatactaac gtttttgtta taccaacatt ggggacccaa caaggcacct   3900
gggaatacat acagacaact gcaaaatggt ttcactcctc ttaccttggg ggcaacccctt   3960
gccccaacta taccccctgt caacaggaag agcagttgtc agccttttcc catctcccca   4020
gctcacacct caggattgag gtgtgctgaa gcacaaggga gggaactgaa accacctttg   4080
caaagattat gacagcaaga aaagtctaac ttgactgact ccatcttgct tctagtctca   4140
caggctggct gtctttgcta attcctgggg gcacaaagag ctaaccatgg gagggattta   4200
gtttatagtt tcacttggaa gcaaggatga taacagtccc tccctaaaac taatctcctc   4260
cttgcttaga gagtgaaaac taatgaaagg ccacaagatt agggttattg gagggacctg   4320
aattctgcta aagtataggt atacttttat aatcccttac tgctcaggag tcatgtggcc   4380
agaggtcaca agatttgtga cttccccaat tgctcttata gataacatca ctactgtaga   4440
acttaagatt ggtctcttga gatgtttttc agatttttgt attctggcca tcaactgatc   4500
ctacctggac tcatgactca tgactcaact ggtcctgtgg cccccaccca gaggcagact   4560
cagctcactg ggacagtttt ccacacccct atgatttttt tcccaactaa tcagcagtac   4620
ccattaccta gtccccgccc accaaactat ctttaaaaat cctaacgtct gagttctcag   4680
aaagactgat ttgagtggta actccagtct ttctgctctg ctgccttgtc acttctttat   4740
tgtaatttaa aaaaaaaaaa caaaaaacaa ggtgaaggag ccaggcatgg tgtctcatgc   4800
ctatcattcc tgtattttgg gaggctgagc tgggcggatg acttgaagcc aagagtttga   4860
gaccatcctg tgcaacgaag tgaggcccca tatctacaaa aaataaatta tctgggtgtt   4920
gtggcatgtg tctgtagtcc caactgctca gaaggctgag atgggaggat tgcttaagcc   4980
cagaagttca aggcttcagt gagctatgat tataccactg cactccagcc tgggcaacag   5040
agcaagaaac tgtctaaaaa gaaaaaaagt aagtacgttc tgatagtatg tctcataata   5100
tcctgtaatt ttctttctgt aataggcatc aaaatggcaa ctgagtgact gcttatctct   5160
gtatcatctt tcccaataca atatgaactc tatcaaagtg aggactatgt ttctctttta   5220
caccatggta ttcatagtgc ttagcatatt attagatgtt cattaaataa ttatcaacag   5280
```

-continued

```
aaggaatgaa tgaaccaatt aatcatgagt catgaggaga caaaagaatt tgtttggcta   5340
ttgtctgagt atatttataa tttgactttc cagaggtcat tgttgaatag atatgatgta   5400
tgctgttttc aaaagggtca ttgaaaagta aatgattaga tgaacttaca aattattaac   5460
tatcttcaaa cagtctcttt gtcactctgc tatatataca tttttccctt cttcccacac   5520
tccccctgcc tttctttctg ctacaggtac agggtattaa caaagatggc agattctttc   5580
tcaaatatac agtttttaaa aaaaaaaaaa tccagaaatg gttttctcga catttgaaac   5640
aaagctagaa aagaaataaa tttcagtaag tatattgttt cctaagagac aagagtatga   5700
ctttcatctg ctgttatgtc agattgtttg atatcacaca atccagatta aatgcagcta   5760
aataggactg tctttgcttt ggaaatcggc cttattagag ccaagaagct ttcttgcaaa   5820
tctataatat aaacaaagta tagtaggaga agtaagcatt attttgcact caaagaccat   5880
gagtttaaga gaaaaagtca ctattgtaac aattgctttg taattgtaaa ttatcacaaa   5940
tttatggttg ataaaggtct attccactat tgcaaatatg ttggaaggag ctgggatgtg   6000
gaaataaata agataaatat aaacatatac tatctgttgt atccctttct gtcttgttca   6060
tcttcactag atggtaataa taataaaaat gaattcagct tgggacttat aaagcattta   6120
taacaggcca gacactgttt gttctaaact ctttgtatat gttaactcat ttaatatatg   6180
caaccctgta aggtcactat aatcctctaa gatcaatacc atgagttagc ccagtttaca   6240
gaaaaggaca tgaatgcacc aagaggtgca gtgacttgct cagggcacac agtaagcgac   6300
agagctgggg tttaagctaa gatggtgtgg ttccacagac cttactttta ataatttact   6360
atttagtta ttacatataa tctcttgatg ctatattctt cctagaataa cacttataaa   6420
tcagcaagca tgcactgagc tctgacctag atgccatggg ggaaacaaaa aatgacacca   6480
tttgatgctt cactcactct atttggggtg tcttcctgaa ctgaaattaa tttcaaacgt   6540
ttagattttt cctgacattg tttctcagct gatgtgttag ggcatactgg agtgtcaaac   6600
tttgatctga ttacatttta attttgcttc accaacagta gatagaatgt gaagctaaga   6660
aggtcatgct gtgcagtaca gaatgtggta caaaccacta ggggataaga cacaagaagc   6720
agaaagtaat attatgccag ctccccaaga aagatcacag gtttctttga acatgtgaaa   6780
ttctttagtg gagattttttg gctcttgtag aatgtaagct acctaagggc agagatttgt   6840
tctgtcttgt ttacagtcgt attccctagg agcaagtgca gtgcctgaca cagagtaaac   6900
aataaataat tgataaggaa atgaatgaat aattaaaaat cagagagtgg ggcaaagcag   6960
aaataggttt actctcacag tgacatagtg ccaacaaggg acaatagtgt gataacggtg   7020
catgatttta tagtcattgc tgtgtatttt tatattcttc ctatggtacg ctttttgatt   7080
atgtagatag catttttttta gtccttttct ttctttgtgc catgaaaaat tctaggattc   7140
agaaatttat cacgaacaca aatgtgtata caaatccttt ctaaatctct caaaggaata   7200
ctaatgcatt tacagttgca catccaaaat aaaagaacta ctctgtttgg tttttgatag   7260
acaacttgca taacaaacag aaaacacagc cacaatttct agagaaatgc ttattaaaaa   7320
gacatacagt tctaaaaaac aaagtctact aataaaaaaa taaaggaaca atttttaaaa   7380
gatgcacagc caagactaca gagtccttgt tttaaacaga gaatgcttga gttgagacat   7440
attctttcaa tctctgagtc ccactgttta gacatcaccc gtggtagttt agggaaagga   7500
tcatcttgga ccttaacaaa aaccatccag cttttcacta acaattttct tatctctagc   7560
tataaatagc aatctttcct ttctgaagaa ttgcaaggtc actttccttt tttatcaaaa   7620
acaaacaaat ccggttttgc tgggggtact gatctgagtt gggggagcta ctttgaagga   7680
```

-continued

```
ggtaggttta gtactggggg aggtaccagg agatcccagc ttaagataaa tgcccaaact   7740
ccctcagata catgagaagc agcagacaat agaaagaatc attgagcagc attagtataa   7800
ggcattatat tctacttgtg aaatttcaag aaaatgtgtc tttaaggcct aggcaggcag   7860
atcacttgag gccagaagtt cgagaccagc ctgggcaaca tggtgagact ctgtatctac   7920
aaaaaataca caaaaaaata gccatgcgtg gtggtacaca cctgtagtcc cagctacccg   7980
ggaggctcag gtgggaggat tacttaagcc tgggaggtta aggctacagt gagctgtgat   8040
cacgtcactg cactccagcc tgggcaacag agccagaccc tgtctcaaaa acaaacaaac   8100
aaacaaaaaa caaaataatg taaaataagt tttaccttat tgggcgagtt atttctgagc   8160
gaccatttga tgcttcactc acactatttg gggtgacttc ctgaactgaa attaatttca   8220
aatgtttaga tttttcctga cattgtttct cagctgatgt gttagcttta tatacacaca   8280
cacacacaca cacacacaca cacacacgta ctcagcacat cttcaaatta cttctgtagc   8340
acaaaaacac acaaattgac caatggaaca gaaataagcc agtcacaaaa agacaaatat   8400
tgcatgattc cacttatatt aggaatctaa actagtcaga cttttagaaa gaatgttggt   8460
agccaggagc aggagagaga gagaaaaggt gggttgttgt tcagtgggta tagagtttca   8520
gttttgcaag gtttgaaaaa gttctagagc tctattgcac aacagtgtgc atagagttaa   8580
cacaactgca ctgtacactt agaaacagtt aagatggtaa ttttatatgt tttatagcac   8640
aataatttaa aaaatatagg aaggacatgg tctcagaata aagggccatc ttttatcata   8700
aagaaaaatt tgcaacccaa ttccaacatg ttaaggtgtt ctcttcttgt tgtttcattg   8760
agaactgcta aaagtctcag tgcccttctc atttggatgg tggtcctact caaacgtttg   8820
gagaccaaag ccccatttgg taataagaag gatgtgttgc ctggcctggt gctctgggca   8880
tatacacttc aggagaacct ttcgtaggta ggggttaagg attggaatct gtcctgacag   8940
aacaatgtct tcacacaatt aacacatagt tcacatacta gatgaaaaca aattccaagt   9000
ggactacaaa tataaatctg gggggaggag agagggatga ataggtggag cacaggggat   9060
cactagggcc atgaaattat tctgtatgat actgtaatgt tggatacatg ccattataca   9120
tttgtaaaaa ctcatagcat atgcaatata aactatagat ttagttaata ataatgtgtc   9180
aatattggct catcaatttt aacagatgtg acacgctaac gccaagatgt taataataag   9240
ggaaactgtg tatgtgggta gggcaggaaa agggtatatg ggaaccctat actttctgtt   9300
caatttttct gcaaatctca aactgctcta aaaaaattaa ttttaaaaaa tgagatgaaa   9360
gaagaaaaat gaaaaaataa aaataccaaa gaaataaaaa tagaagaaaa tataaattaa   9420
tttataattt aagaataaac tttctaagaa tatatcaaaa aactatgaat ccagaaggaa   9480
aagactaata cacaaccaga aaaatgagca aaagctatta atagactatt ttttaaaaga   9540
agaacaataa atgttcaata agactatgag agaaatgttc agtcacatta atactaaaac   9600
ttaaaattat gagatttcat ttttatctat gaaattggca aacattttta aaagagataa   9660
tagtaatcat gaggagccaa acaggcattt tcacatatca ccagtgagga ctgtaaattg   9720
gaatgacctt tggtcagaaa aaatttttca aaacttggaa agcaaaatat gattgcataa   9780
tttgttttca tgttaggcat tgcctaacca gtccatctaa ggtgaattga atcctgactc   9840
gttattacag atttgcacat tttacaactg taaattcaaa tgttagtttg tagaaaattg   9900
gtgagatgct atatttttgt ccaatggaga tataatttct gtcctgcaca gatgaaaata   9960
attttgctct gtaaagatag caccaaacat tatggtttat caccctgtaa gacattaatc  10020
```

-continued

```
agatttatat ctaatttagc aataatgtag aatgatttta gtattctttt ttatatattt  10080
atgtatatat ataggatgta tatttacata tgtatattat atatagtatg tatatacata  10140
atataaatac aatatgtata taggtatgtg tacacataat acatatacta tatgtatata  10200
tgtacataat atacataagt atatacatca tatacatata tgatgtctat atgtatagac  10260
atcatataca ttatgggatg tacatacata tatacataac atatacatat attatgtata  10320
tattattata gatatatgta catatataca tacatatatg tatgtagtaa atgtatatat  10380
agatacatat gtgtatacat atatagatgt atgtacatat atctatgtat atacttatag  10440
atgtatgtac ataatatcta tatatatact tacagatata tttatataat atctatatac  10500
ttacatatat gtactatgta tatttagata tatacacata tttatacata tatgcatata  10560
cacatataca tatatatgta tgtacatata taaatagata tacataatat atgtatatac  10620
acatatagat atatatgtac acatatagat atacgtgtgt gtgtgtgtgt atacacacat  10680
atttctcat gtctttcttt gaactggctt tgttatcctg ctggtttcct cattaataag  10740
ttaaaattaa aacttgaact gtgcttactc tatatttgta tgagaatact ttttaacatt  10800
ttttaaatta tacatttgac attttatagg agtataactt ggccaaatat tttaagtctt  10860
aaaagtgtac atgcttttta acctagcaat tacatgtcta agaaatgatc ctaaggaggt  10920
aaggacatgc tcaaaggttt agctctgaga atgtttctag atgtgctgtg tataataaag  10980
aaataccaga aacaaatgtg ccacattagg gcgctggtta atacctaaat gtgtgtgtgt  11040
ttgtttgatt gttttggggt ttggggattt ttttttttta agacagagtc tcattctgtc  11100
acccagaatg gagtgccatg cgatcatggc tcactgcaac ctcaaacccc tggggtcaag  11160
caatcctcct gccccagcct cctcagtagc tgggactacc ttgccccatc cctaaatgtg  11220
ttttaagaat ggttgtttcc aggtaagtaa aatttgtaag tttaaaattt ttcttttatc  11280
ttgttcagat tttcttgtga cactttcaaa gaaaaaagtt tgaaagtcac aaagtctagt  11340
tatactgttc tcattcttgt tgacatctat tgaggtactt agccccgact atagttattc  11400
cctctgtccc aattcctgct actatcttag ggaaattcag agtccttaaa cagaaccaat  11460
ccaacactct ggctttttca ttccttaatt tcccatttcc agtgatcttt acctcctctt  11520
cacttttgta attcactcta agatattttg atcctgtttt cattcagaat tagtcattgg  11580
tcctctctaa cacttttgtg ctttttcctc tgctttgctt ttaaattaaa atgccttcat  11640
tgtttttcca atttaaaaaa gcaatgcatg tttggtggaa aaacttttca gaaaatacag  11700
aaagatgtaa aaaagaaaat taaaacattg caactcgtgg atttgcactc agcatgttgg  11760
taaccttaga aacacattgc tgggaatagt tttttttgt ttgctttatc taaatgagat  11820
cttactattt attttacttt tattatctgc ttcttgcctg aacaatttgt ctttccaagt  11880
gaataaatgc agatctacat tgacattatt atggctgaaa aacaattaat tgtacagcta  11940
taatattctt taacccaggg tgtcttaact tcagcactat tgacattttg ggctgaataa  12000
ttctttgttg tgggaggctg tgttgtgcac tgaaggatat ttaatgcctc cctgccctct  12060
gtatcagcac tagatgccag tagctcccat ccctagttat gacaatcaaa aatgtctcaa  12120
gatattgcca aatgtctgct gtgggcacta ctgcctcaag ttgagaacca ctgatctaac  12180
caatctgctg ttgtttgaca tttaggtttt atctactttg tcacaattta aagcagcagc  12240
acttatgaag ctcctaacat atacaaactc aacacatctt caaattactt ctatagcata  12300
aatttctagc aaggaatggc acatacaaaa ttttgatgtc tattcccaga tttccctcca  12360
gaaagattgt attaatttag aacaccattg aaacagcata aatgtcattt cctgagatcc  12420
```

-continued

```
tgtctacttc caggtattgt caatcttttt aatcttgctt tgtgataagc aaaacaaagt  12480
attactttac ccttttaact tgtaattctt tgattgctta ccaggttggt aacctttact  12540
atatttatta gctatttgtg ttactgcttt tatgaactgc ttattcatct cctttgctca  12600
ttctttattt tgtaagagca ttaattcctt cttccagctt gtaatttttc tcataacctg  12660
atttaaacct ttcttcttat aacctttata aggttttctg tacagaagtc atacatttgt  12720
atgttttcaa attattagcc tttttattat ggttttacct ttaatggtgc catacttaga  12780
aagatcacct ctaggtccag gcctggtggc tcacacctgt aatcccagca ctctgggagg  12840
ctgaggcagg cagataattt gaggccagga gttcgagacc atcctggcca acgtggtgaa  12900
accccgtctc tactaaaaat acaaaaatta gccaggcgtg gtggtgggca cctgtaatcc  12960
cagctactca ggaggctgag gaaggagaat tgcttgaacc cgggaggtgg aggttgcagt  13020
gagctaaaat tgtgccactg cactccagcc tgggcaacag agcaagactc tatctcaaaa  13080
aaaaagaaga aagaaagaag atcacctcta aaatctctaa acttcagtat tttactctat  13140
taggctaacc ttttattttg ctgttatctt tcatactctt aacactaaat tttttttct  13200
ctcttgacca gtgcacctta aacttgaatg tacatataca tcatctggaa atcttattaa  13260
aatgtgtgtt ctgattcagt aggtttggag tggagtgaca gattctacat ttccaacaag  13320
ctcccaggtg atgccagtgc tgtccctggc ctgcactctg agttactagc tcctaaacct  13380
tcagcactca gtcctctgta ccccctacct ccattctctg actccttcct gaagttgcct  13440
cccttcctac ctagtgtgaa ccccaatggc agcaatttca actatagctc atctctgttt  13500
ttccagaaca acaatcctgg caatctccat tccagtattg atgaagccac catttcttcc  13560
agtctccagc cacagcaccc tgcaggaaat cagatagtgt ccacgtactt ctcttaaaaa  13620
gataggattt ctaaggtaca tcagcaagcc ttcactttgt tcccacccag ttccctttcc  13680
cattcctaga gtaactttgc ctaaatttaa tcttctcaag ctccagtccc cctcctcaga  13740
cctcttagtc aatgaacaac aatgaaaggg aaacgtcttc aacccttcca gtggaaataa  13800
catttagcat agtgactact gcacaattaa aaaaaaaaaa acctactcaa agactctaca  13860
atgtcatact aagacttcca actcttaggc caggcaaggt ggctcactca tgtaatccca  13920
gcactttggg aggctgaggc agaaggatca cttgaggcca ggagttcaag actagcctgg  13980
ccaacatggt gaaacctggt ctctattaaa aatgcagaag ttaggcatgt gtggtgtaaa  14040
aatacaaaag ttacgtaggt gtggcgatgc gtgcctgtaa tcccaggtac gttagaggct  14100
gaaacacaag aatcgcttga acctggaagg cagaggctgc agtgagctga gattgcacca  14160
ctgcactcaa gcctgggcaa cagagtgaga ctgtatctca aaacaaacaa acaaacaaac  14220
aaacaaacaa acaataaaac aacttctctt taagaaaaaa aaaaagatgg ccaggcacgg  14280
tggctcacgc ctgtaatccc agcgatctgg gaggccgagg caggcagatc gcccgaggtc  14340
gggagttcca gaccagcctg gccaacatgg tgaaaccccg tctctactaa aaatacaaaa  14400
attagccggg cctggtggca ggtgcctgta atccgagcta ctcggtaggc tgaggcagga  14460
gaattgcttg aacctgagag gaggttgcag tgagccgaga tcatgccatt gcactccaga  14520
ctgggcaaca gaattgagac tccatctcaa aaaataaaga aagaaataaa aaattaaaaa  14580
aaaaattcca actcttggaa aattcccttt aaagagttac gaattaagct ggtttattta  14640
tgtaataaac gcttcgcaca gttcttacaa tgtgcctgcc aaccttattt aggtaggtac  14700
aattaagact tccactttac acaccagaaa ataaggcaca gagtcgacac agccactgag  14760
```

-continued

```
tgtcagagca agaattggca ctcatcccgt gagcgcctca gttctttttt tttctttata  14820
tatactttaa gttctagggc acatgtgcac aactgtggca catatacacc acggaatact  14880
atgcagccat aaaaaaggat gagttcatgt cctttgtacg gacatggatg aagctggaaa  14940
ccatcattct cagcaaacta tcgcaagggc agagcgcctc agttcttaaa ccactcttct  15000
atgctgcggc agaatcactg gaagtctcag ggagtcctga gtgcgcaatt ctaggaaaag  15060
tatctatatc tgtaagaaag aaggggcagg gaatctaacg gttctcagct cttgaaggca  15120
cattagattc attcaaggtc ctctctaaaa atacactttc ttgggcctcc acgagaaaaa  15180
ttctattcaa ttagtcgtgg gcttgcatcc gtatttttag tctgtaaaag tggaatgtta  15240
tctcaaatca gtggttttca aactttttat attctgcgga ccttgacacg ggcccccaat  15300
accctgacac ggttacttac aatccgggag agagtgggag aaagggggag agagggaagg  15360
ggagaggggg aggggagaga gagagaatga atgagaatga atcttttaga gaggtagagg  15420
gggttggccc gtgccacaaa ccacctctca ggtttgagtg aagccttcgt tctctctcgt  15480
gcagagacca tgccatcctt ccagaaagga gcattttagg acgttttagg acgagagacc  15540
tgtaattggc ctaagactca ggtgcaggtg gaggaagcat cggatttaca acagtggtcc  15600
tgccttcttc gatgtgactt ccagttttaa attcaattct aatttacaca aatcccaccc  15660
actatgtaaa cttgttggaa aatgtcctgc actctgcact tcgtggcatt taaaacttcc  15720
acacacgcgc gcgttctttc tcgaagcccc gtgattgctt agcctcgctg ggcagcttgg  15780
cactgctggg agcttggctc gccctgccgg ggccgacgcc gcccgtcccg caggagcccg  15840
cgcggggctc agggcactca ggactccgca tgcgtcccgg ctccaggtgg gccccggcac  15900
cgccaaccgc aggaaacccg ccgagcccta aacgtctccc aagcggctgc agtctgcgac  15960
agagagtgtc cctcggtgga gcgccctgtg gctgcccagg ctacagccgt ggccgaggcg  16020
aggacacact tctgacctgg ggctccagca aagactgtcc gcgagcggcg actccatgcc  16080
cgcagccctc cgcccagctc agccgcccgg ccgcgggcac cagcagccgc gccacgaaag  16140
ggcgcaccgc gcgggcgccg tctctcctag gtgcgaaggc ggctgaggcc ccgcccggga  16200
ggcacccgcg cggctccgga gtgggccgga gggacgtccg ggggcggggc ccgggcgcgc  16260
ccgccctctg accgggctat aacacccggc cccgccgggc ggccgcgggt gggtagaggt  16320
gcgcgcctgg gacctggtga ggctgggggt gcgcggggcc gggcgcagct gtggcagctg  16380
ccggacggcg gaggcgccag gaggaggagg agagggaggc gcgggcggct gggtcgaggg  16440
caccgaggct gcccgtgctc ccggtctctg gttgcacggc tcactcccga aggtgttgct  16500
tccagctttt gcctccttag gaggcaggga gcgtcagtgt cgggagaccc tgagaccgga  16560
gtaccgagac gtagctggtg atgcccccgc ctgccctcat gtgttctcag gttcttctta  16620
tttttattca tctctagaac atggacttcc cgtgcctctg gctagggctg ttgctgcctt  16680
tggtagctgc gctggatttc aactaccacc gccaggaagg gatggaagcg tttttgaaga  16740
ctgttgccca aaactacagt tctgtcactc acttacacag tattgggaaa tctgtgaaag  16800
gtagggtccg tctcgtgaac actttgccaa accctcagtc ctccctttca gtattcatta  16860
aatatgcccc agcttcctgt ctgctcttcc acgcacctac tctgagtggc acagaacaag  16920
tcaaccggta ccgtgcgtgt tggttgtttt ctgcttttgt tgggaggaat agtaggaaga  16980
actgaatttt actggacttg tccattgtaa ttcagtgtca ctgagtcctt tccattattg  17040
gagttcttct gtctttttgg atcttgcaga cattggttat ttgggatgta tgttttagtt  17100
ccttttcaag ataaactccc aagtaagtcc gtttatccgt ttcagttccc ctttgtgtgg  17160
```

```
gcttctttat atatgacttg gactgttaat gtcatttctt catgtctctt ttaaactgaa  17220
ataatgcagt tttgttggta agatttctgt gtcatctgta gttagccttt tatttaaagt  17280
tatgcaaaac tatcatttct gcaagtttct tttaatctaa gtagtacagt tctgttggtt  17340
agatttgtgt cgtgtataat tagccctatg gcttaaagtt atgcaaaaaa gtggttctat  17400
gattaaaggc tgtttttaaa atgtatccat ttgaagaaga caatgctaga taatgaatat  17460
atattagtag tgattgaaac tcttcccagc attttcatat ttatcattaa taatttattg  17520
ttctaagtta gaaactacat aaagttattt tcatttttat agacagcaag tttgaatcag  17580
ataaattaaa taatttgttc aaggtctccc agatggtgaa ttttatagcc aggactggca  17640
cccatccggc caaggcaaat aatttgatca gatatcgtta tttcatcttt ctttctttct  17700
ttctttcttt cttttttttt tttttttttt tttggtcaga gtctcgctct gttgcccagg  17760
ctggagtgca gtggcgtgat ctcggctcac tgcaacctcc ggcttcctga gttcaagcaa  17820
ttctcctgcc tcagtctccc gagtagctgg gattacagga atgcgccacc acagctggct  17880
aatttttttg tatttttagt agagatgggg tttcaccata ttggccaggc tggtctcaaa  17940
ctcctgacct tgtgatcctc ctgcttcggc ctcccaaagt gctaggatta caggtatgag  18000
ccaccgtgcc cggccgagat accattatta cttaatcatc ttttattatc ctgatgttcc  18060
caaagaggtt accagaaaac ttagtcctta aatcaaaagt ttcataaatt ttatgcaatt  18120
tggatctcaa ctttttgtaa ggtgtgttca aactctacct tgattttagc tctgaacttt  18180
tgagtcaatt gagagtctca taattaccat attcttcatc atttttcaaa aaaatcaagg  18240
ctatggcttc tatattaaag aaaaagtatt atataaatgt atttatgtgc aatgcgaagt  18300
caatatcctg ggctgtgtgt aatagtaact ttgtttttaa acagcattgc caaagagatg  18360
gtgccagaat tactctatat tgctctataa tccaaaatta tagaggttgg gtgtgtgaga  18420
aatcatatct tgaatcagca tacgtattca gccttctgaa atcatttttc cctagggcta  18480
gagtagagca atttaaaaag atctaggaat actaattata ttaattaaaa atatatagaa  18540
cacaactagc ttgagttatt gttcagtcat catttcaacc acaagatgat gaggatgttg  18600
ttaattttaa gtactaagtg atttggtaag gttttgtatt ttcaaacaca atgtgcttgt  18660
gacagttggg ggctctcttt cctaatatga atcagcagtt gtgatctatc ctgcatgata  18720
tcaaaccaca atcacagtga aagtcagcag gcttaatttt gtttttaatt ttaccttgta  18780
tgcactcttg cggttaaagg cttgaggagt tatcatgtaa aaataaaatc tgacactagt  18840
ggttaaatat ttgtgttgaa tatgttgttc tgaataataa ctcggattaa gaaaaatccc  18900
aaatctgcca tttggctcca actggtagat gaaactgtat gccagtaact gggagtcagt  18960
tgccaaagtg tcactgcaca ttagtgtgac aattgagaga tggtgctcct ttgttggtgg  19020
tctttttcac tagatatttt ccctaaccat tctgccctct gatgtaagat aagtttgctt  19080
agaaaacaga atttatgacc aggcccagtg actcatgcct gtaatcccag caccttggga  19140
ggccgaggcg ggaggatcac ctgaggtcag gaatttgaga ccagcctggc caacatggtg  19200
aaacgttgtc tctactaaaa atacaaaaaa ttaaccagac atggtggtgt gcacctgtgg  19260
ttcccgctac tagagaggct gagaccggag aatagcgtga acccaggagg cagaggttgc  19320
agtgggccaa gatcatgcca ctgcactcca gcctgggtga caagagtgaa actctatctc  19380
aaaataaaag aaaataaaca gaatttatta tacacgtgtt atttatttat ttatttatat  19440
tacatgtatt aacgtgggca gtcttaccca gaagggaaag taatattcct aagtaactaa  19500
```

-continued

```
atacatgttt agtttttgta aaaacttaaa tatatgtgct atgcctatgt aaatatatgc  19560
atatcacata ttttctttgt tgtaattgtg gattatattc tgcttgtttt ttcatttcat  19620
gttatttcct tagatatttc catgaattga caaagtcggt agatgtgaat tcgttgctgt  19680
ttagtattct atcctcttga ttatgtgaat tttcttagtc attcacctct ttgagcatct  19740
gtatagtttt tggttaactc tgttataaac agggatacta taaaaccatt gatacatgtc  19800
atgataatta ccttctatta ttattggtga tttttaaaaa cgtttttatt ttgaaacttt  19860
taaaatccac acaaaagtta aacacatcta tacccagctt cagccatagt agaccatatt  19920
tcagttgagc cttttgaagg aaatcccact gcctagtgac atagtaaaga aaatcttagg  19980
tgaaacaaga gaagcaaaaa agtactgatg acttagttca gaaaaatcag aaaaggtaca  20040
gtgttcatca gttcgttcgt tcaatcctcc gttcaattaa ggaagcacct cccatttttt  20100
gccccaaccc ctttgtctag aaggatgcct ggcacataat caataatcta tatctattta  20160
tttaatggat caaatatttg ctgagcaaaa ggcatgggaa gcaaacaaac gtgtgtgtca  20220
ttcattccct gccattaggt agctcatttt caaatacaaa tgtatttact gtgaatttct  20280
cagggtagtc tctccacaca caccccaaaa ttagtttagg aacattttat tattttttta  20340
aaaaatgaac ccttgtgttg agggttgact atcaatagat agcaatgaaa gaactgctct  20400
gctacataca aaaccccaaa gggccatttt aaatgagatt tcctaccatc tattttaaga  20460
atcttgcatt gactgggtgt ggtggctcac gtctataatc ccagcacttc aggagaccag  20520
cctaggcaac atgggagact ccatttctta aaaaaaaaaa aaaaaattta attaaccagg  20580
cataatggtg catgcctgtg gtcccagcta cttgggaaac tgaggcagga gaatcacttg  20640
agcctgggag ttcaaggctg cagtgggcca tgatcgtgcc accgtactcc agcctggcct  20700
acagagcaag accctgtctc aaaaaaaaaa aaaaagtatc ttgtcttgcc tcctgctaag  20760
tctgatcatc attgtatctg aatacagtag gcgggataat aacaccttcc ttactagtga  20820
taatactatt agagattttt taaagccagc caaatttagt agtctctgtt atcaagtact  20880
ttccatgtag taaatagttt aagacattat ttcgatctca gcaactcaaa gtaggcctta  20940
tcctcattta caaaacaggt aaaatgaggc acagagaggt taattaactt gctgaagata  21000
acatagctaa gtattagaag attcaaactc agatctgcct atttcccaag cacctctcta  21060
ttctctttta aaaagcagct tgacatttaa gtctttaatc catcttgaat taatttttgt  21120
ataaggtgta aggaagggat ccagtttcag ctttctacat atggctagcc agttttccca  21180
gcaccattta ttgaataggg aatcctttcc ccattgcttg tttttctcag gtttgtcaaa  21240
gatcagatag ttgtagatat gcggcgttat ttctgaggtc tctgttctgt tccattgatt  21300
tatatctctg ctttggtacc agtaccatgc tgttttggtt actgtagcct cgtagtatag  21360
tttgaagtca ggtagcatga tgcctccagc tttgctcttt tggcttagga ctgacttggc  21420
aatgcgggct ctttttttggt tccatatgaa ctttaaagta gttttttcca attctgtgaa  21480
gaaagtcatt ggtggcttga tggggatggc attgaatcta taaattacct tgggcagtat  21540
ggccattttc acgatattga ttcttcctac ccatgagcat ggaattgttc ttccatttgt  21600
ttgtatcctc ttttatttca ttgagcagtg gtttgtagtt ctccttgaag aggcccttca  21660
tgtcccttgt aagttggatt cctaggtatt ttattctctt tgaagcaatt gtgaatggga  21720
gttcactcat gatttggctc tctgtttgtc tgttactggt gtaagactta aacgttagac  21780
ctaaaaccat aaaaacccta gaagaaaacc taggcattac cattcaggac ataggcacgg  21840
gcaaggactt catgtctaaa acaccaaaag caatggcaac aaaagccaaa attgacaaat  21900
```

-continued

```
gggatctaat taaactaaag agcttctgca cagcaaaaga aactaccatc agagtgaaca  21960
ggcaacctcc aaaatgggag aaaattttcg caacctactc atctgacaaa gggctaatat  22020
ccagaatcta caatgaactc aaacaaattt acaagaaaaa aacagacaac cccatcgaga  22080
agtgggtgaa ggacatgaac agacacttct caaaagaaga catttatgca gccaaaaaac  22140
acatgaaaaa atgctcacca tcactggcca tcagagaaat gcaaatcaaa accacaatga  22200
gataccatct cacaccagtt agaatggcga tcattaaaaa gtcaggaaac aacaggtgct  22260
ggagaggatg tggagaaata ggaacacttt tacactgttg gtgggactgt aaactagttc  22320
aaccattgtg gaagtcagtg tggcgattcc tcagggatct agaactagaa ataccatttg  22380
acccagccat cccattactg ggtatatacc caaaggacta taaatcatgc tggtataaag  22440
acacatgcac atgtatgttt attgcggcac tattcacaat agcaaatact tggaaccaac  22500
ccaaatgtcc aacaacgata gactggatta agaaaatgtg gcacatatac accatagaat  22560
actatgcagc cacaaagaat gatgagttca tgtcctttgt agggacatgg atgaaattgg  22620
aaatcatcat tctcagtaaa ctatcgcaag aacaaaaaac caaacaccac atattctcac  22680
tcataggtgg gaattgaaca atgagaacac attggacaca ggaaggggaa catcacactc  22740
tggggactgt tgtggggttg gggagcgggg gagggatagc attaggagat atacctaatg  22800
ctaaatgacg agttaatggg tgcagcacac cagcatggca catgtataca tatgtaacta  22860
acctgcacat tgtgcacatg taccctaaaa cttaaagtat aataataata aaataaaata  22920
aataaataaa aataaaaagc agcttgacac agatggggat gattccatgg aagttgaggt  22980
cattagtaga gggttttagg accatggttt gggcacattt gacctgaagg tatagctcta  23040
ccaaggatct agagctgttc aattcagtag ccattagcca ctaagcaatt gaggagttga  23100
aatatgacta gaccaaactg aggtgtgcta gaaagtgact ttgaagactt aatacaaaaa  23160
aggaaaatat ttcactaata atgttttata ttgattacat gttgaaatga taatatttta  23220
gatatgttaa ataagaaata ttttttttaaa ttaatttcaa ggccaaaagc agtggctcac  23280
acctgtaatc ccagcacttt gggaggctga ggcaggtgga tcgcccgagc tcaggagttt  23340
gagacccgct ggggcaacat ggcaaaaccc catctctacc aaaaatacaa aaaattagct  23400
gcgcatggtg gcatatgcct gtcatcccag ctacttggga ggctgaggtg ggaggattgc  23460
ttgagcttgg gaggtggagg ttgcagtgaa ccaagattgt aattgtgcca ctgcactcta  23520
acctgggtga tagggtgaga cccccatctc aaaaataaat aaatatataa ataaaaatta  23580
atttcacctg tttcttttta cattattgta actagcagaa gattaaaatt atatatatga  23640
cttgcattat attttgatcg gactgtgctg ctatagagtg caatttgtta ttattaattt  23700
tttcctgcgt acaaaaggaa ttctagttca tttagaaaat ttggatcata caacaaagca  23760
ccaaaaagaa aattaaaatc tcaccatcca aaggaaacat ttagtagact gcaatcatac  23820
tacacagttt tgagcctttt tacccccctg agtcaaatat cttattttgt ttgtccatgc  23880
aaacatgtta tctctaaaac ttgattttta atttctgttt tgtgtcctgt caatagatat  23940
tttattgttt aacttatgcc ccactggtga atatttagtt tgtttctaaa ctttcgctgt  24000
tatgatcaat gctgtagtga acatccttgt agctaagaca gcaaaaatct gagcacaggc  24060
tttggaatca cctgcccaag ttcaaattcc ggattctcag ttttgtagct acgtgaccat  24120
gggtctttag aataattcct ggcacatagt aagtgctatg taaaagctgc tattattatt  24180
attattaata catacccaaa aaggaaatta ctaagtctaa agctgtttta agtatttgat  24240
```

-continued

```
atatatacca aattgccttc caaaaagatt gtgttgattt ataatttctt gggaaatgca  24300
tattaagaaa aataaaacaa ctcttctaaa acttacacta gtcataaatc aatactgtca  24360
ttagtgcttt gaaagatgat tgtagtatgt atttctcatt gttatgttgt aagtatgagg  24420
gagaatttat ttctcttgcc cctttcccta agaactctca ccttcccatc attaacagac  24480
attcactgaa ttcctctact aggagtccta taccatttca gatgttcaga aatctcccta  24540
acattggtta agattcttgc tcctaagagg aaagtactat gttcacatac acagatctct  24600
catgatcact tgccctcaac tggatagatt ttagccggtg atttaccctc agaaaacagc  24660
attgtatata aaattttggc acaacacttg gtcatccgtc acactctgct catttcccaa  24720
atatgctcgt aaaaccagtt tgcttgagat cctgtataaa atgcctattg tgatgcaaat  24780
actgacatat tgaggatgaa tatgaagaaa accactaaaa tctaggaaat tcagctataa  24840
tatacatgtt tgtgatttaa agttatatgg gtttagtaag cctttcccct ttaacataat  24900
acgcagagta cctttctgag acatttatca gctatcagcc ttattcttat tcttgaaaca  24960
ttcagggttt cttaaagaca ttgccttttt tttttttcta tatggagtct cgctctgtcg  25020
cccatgctgg agtgcagtgt cacaatgtcg gctcactccg cctcctgggt tcaagcaatg  25080
ctcctgcctc aacctcctga gtagctaggg ttacaggcac ccaccattgc gcctggctaa  25140
tttttggtag agacagggtt ttaccatgtt ggccaggctg gtctcgaact cctgacctca  25200
taatctgccc atctcagcct cccaaagtgc tgggattaca ggcgtgagcc actgcgccct  25260
tcctatcact tatcttgtca tgcttacatt attccccaca attttaggtt tttttttttt  25320
tttttttaa gtagagacag gtgtctcact atgtagccca ggctggtctc gaactcctga  25380
gctcaagtga tcctcctgcc tcagcctccc gtagctctag gattaaagga atgagccact  25440
gtcccctccg cccacaattt tctaatgtcc tccatagggt aagatgagct tacaattatc  25500
tgagcctaaa accaaaatct tttttgtata caaatacaaa atatttcccc ccaacagttt  25560
taatatatac tgaacttttc agggatgcca ctatatgtaa attgaggggga aattatattt  25620
tgttttgctc ttaacgtgac tgagagatat ttcatattca gagaatcctg acaacagtga  25680
acaaagagcc aaaccaatct gcatttgtaa tctatatgtt cacggtgact ctcaagtata  25740
gatacaagca tgtgatttct ttgtcttcta gtggagtacc caagttattg catatggata  25800
ccatatctta tgtaaattgc attctttttt tatttctgct ttatatagtt tgaacactat  25860
attgatcttt tgaaattatg tatgtaaatg tgttagaatt gtatgccagc atgataaaat  25920
agaagttgca aaatattgga tatgaaagca agaggcatca tctgatagag ttaagaacta  25980
ttggtgtaaa agcacaaaga gagctgttaa ggacccactt gaagctcatg tggccagcat  26040
ccaaaaggtg cttagtttct gttcttaatc cctgaacgtg tgtatctgac ggtaacactg  26100
tggttacagc agtatctaca tttgagatgt gataactgcc attagtcctg attcctcctt  26160
tcagtttgtg tgtttagaac accccttttct ctaagaatgc aaagtaagaa agtaagatgt  26220
aaaaaaaaaa acaaaagaaa accttaaagt gaaattactc aaaacacaca cacacacaca  26280
cacacacaca cacacacaca cacacacaca cacacactct atatcaaata ccaacatgca  26340
tttgggttaa gggaaggaga ctaagtcaaa tttagtcaaa tcttcctgtt tggagctagg  26400
cttggtcctg tagtcccagc tacttgggag gtttacacag gagaatcact tgaacccagg  26460
agtttgaggc tgtactgcac tatgatcgca cctgtgaaca gccactgcac tccagcctgg  26520
gcaacacagc aagagtctgt ctctttaaaa caaacaaaca acaaacaaaa aacacttctg  26580
tctagtgatt taaaacaatt gacattcttc ctagcaatta aatgtaatac tgtatagtag  26640
```

```
tttgtgaaga ggttagtaag tcctaatttg aatttgtgtt aaaataaaag acacaaaatg  26700
cacattaaaa atgtttctca tctctgtttt ctgaggactg ctgcatgtca caggttttaa  26760
aaatacacat tttctatctg tgacctttca catacatacc tttgtcaagc tcaactggag  26820
ggcttaatct ccactgcatc aaaaaaaaaa aaaaaaaaat gctgccaact tcaaacaaat  26880
tgccttggag ctggcttcac agagttatca cgcacttacc cggagttgaa gataactacc  26940
ttgacagtgg ggatacaaag gcagtaatga tagtgcctac taccccagtc tttagtctat  27000
cacagaattc aggagaagcc aattaagtaa tccttctgtt tgtttaaaga actttcaatt  27060
agttgcttat ccagttttta aattattctg atgcaaatcc gtgaaaacta gaaccacact  27120
taaaaatcac aactaaagta tcatgaattg acagttattc aaacacataa ctaagcctcc  27180
tttcccacat aatacacacg cacatataca aatacaggca ggtgaaattt agcataacat  27240
catgttttta gagcacgaat aaatgttaga gaccatttga tcattcatta cgttaattga  27300
aacttagttc aaaatgttgc ttcctccagg aagccttttt ctattccctg ggcagagtca  27360
gaatctcctt ccacacctct tctcctcttg agcatcttcc agtaactcta tgttcacata  27420
gaggccaagg accaggcttt gttcagcttt gtatcctagg cactaagatg tgcttattac  27480
atgtaacaga tactctcaag gacaaagatt aagagttatt atgtgcttat taaatgaaac  27540
atatgaatgc aaatatattg tatgtagtat attaaataat acataagtat ataggatgta  27600
catttttaaa tatactttta tattgttaca tatattatat gtaactttat acacttttat  27660
atagttacct atattgtatg taagttcttc agtccctcaa gaaaatgaca ttgttttctt  27720
atgaactttt tgttaaaatt agttttatat tagtagtaaa taatatgata acttagagag  27780
gtagaattgg gggaccacaa ttatgcccca gttcaagata agtcactggc atgtaggaga  27840
aggcctcaga gaagttacgg actttcaggc agtaaaggac acagttgaat tattcactgg  27900
ctagcctaaa atgggtctac ccccacccct tgccttcagc cccctaaaac actgaccaaa  27960
catgtaataa gaaaagagta attataggag gttcaccacc atcacactca cccctgcctt  28020
cattaagaag tgtttaggct ggttgcggtg gttcacacct gtaactccag cactttggga  28080
ggctgaggcg ggtggatcac ttgaggccag gagtgcaaga ccagcctggc caacatggtg  28140
aaaccccatc tctactaaaa ttacaaaaat tagccgggca tggtggcagg tgcctgtaat  28200
tccagctacc tgggaggctg aggcaggaga atcgcttgaa cccgggaggt ggaggttgca  28260
gtgagctgag agccgagatc acaccactgc actacagcct gggtgacaga gcaagactct  28320
gtctcaaaaa aaaaaaaaaa gtgtttaaat aaatgcctct ggctttattt gaacagtcca  28380
ggaataattc aagggtctgt cacagaattt tgacaaagaa aaaaggtggg agggatcatg  28440
tgaagaaggc ctttttttccc ccaagagtta agcaggggcc aggcacagtg gctcaggcct  28500
gtaatcccag cactttggaa ggccaaggca ggccgattgc ttaaggccag gagtttgaga  28560
acagcctggc caacgtggca aaccccgtg tgtactaaaa aaatgcaaaa aaaaaaaaaa  28620
ttagccaggc atggtggtgc acacctgtaa tcccagctac tctggagtct gaggcgggag  28680
aatcacttga acccaggagg tggaggttac agtgagccga gactgtgcca ctgtactcca  28740
gcctggccca cagtgagtct ctgtctaaaa aaaaaaaaga aaaagaaaaa gaaaaagaaa  28800
aaaaaagctt aagcagagat atgaaaccct tccattttaa gtgtcttttc ccccctctat  28860
actcagaaat gttgtactta ttttaggtga aggcagatga tatgtctaac tattcttgct  28920
gtgagtggtc cagaagggca cagttttgga aatacacaga tgaactgttg aaggtagttt  28980
```

-continued

```
caccttaatt tttagtcctt gttaaatatt tattcccttg tccattgttg gtgactcagt  29040
tgagcccact cgttaaaatc cttttcacgg ggatagtcac tcttatgaaa acatagacac  29100
ctagagacat gtgggaagcg tagggtcatt taacatgtgg cgattctaca gcagttttcc  29160
cattgtttaa ctggagagat ttatttacag cttgtgttag gctgttcttg ggttgctaga  29220
aagaaatact gggtaattta taaagaaaag aggtttaatt ggctaagcgt tctgcaggct  29280
gcacaagcgt ggccccagca tctgctcagt ttctagggag gcatcaggag gcttttactc  29340
atggcagaag gtgaagcagg accaggcacg tcacatggtg aaagcagaaa caagagaaag  29400
agggggtggg aggtgccaca cgcttttaaa caaccagatc tcgtgagaac tcactcatta  29460
ttgtgaggac aacaccaagc catgagagat ccactcccat gacccaaacg tctcccacca  29520
ggctccacct ctaacatggg ggatgacatt tcagcatgaa atttgggggga acaaatatct  29580
aaactattca caccttacta ataatactaa atgtgcacag ttaaatttca gataaagatt  29640
gttcaattgg ggcagacacg taattttttc cattgctctt tgggactcag atgaataatc  29700
ttagtgtggt agagataagc ctagctggtt tgtcatgtgt tactgtcagt tcctttcaat  29760
ttatgaagaa acagaaagat aaattgggaa atgtcacatt ctagccttga cgaacttttt  29820
agttggactt ggccatcttt cgagttgtaa gaacatgtac ttctaagggt acaaaatgtg  29880
tttccaaact ctatggcata cagttctagc ataacaccat gtcagtcaat tgcagaaact  29940
tccaaacatt ttttacactg agagctcttt ggtcaaataa ttcttgcttg gaagtaaatc  30000
ccagtctgtg tgtgccaggc actgtgttag gctagagaca gagtcatgag caaatagcat  30060
ctctgctctg atgtttctta catgtgctag tgagggaggc aaacaaaaaa caaggcgagt  30120
tcagattttg atcattgcta tgaagcaaat acatagttta gtataatgga gagtgacagt  30180
tactgtggaa cataggttcc atgaaagcat ggagcctatc ctacttgtca ctgtattttc  30240
agtgcctaaa acatagcagt tactgtttga gagaatgttg tatggaaaga atgacaggag  30300
gcctgcctga aaagatggta ggttaaagtg gagatctgaa aggtgacagt cagctagatc  30360
ttatagcctg attacaaagt gcacaaagtg caagtgatgt gcaaaggcct cgaggtggaa  30420
agagtagaac agaagtgaga ccagggtggc tggagcccag tgagcaaggg gaaagtggtc  30480
tttgagcaag ttggaaggta cacaggggac agagcataga gtgccttcta agccaattct  30540
aaagtggaga gtttgaattc tgttctgaga ataatgggaa accattgaag ggttttaaga  30600
agagagtgat gcaatctgat gtgggtttta gaaagataac tttagctgct gaatacagaa  30660
aatggccaga atagaagcag ggagactaat ccagttacag tagtcctggc aaatgttgat  30720
gatggtgatt tggattaaga tgctctgtta ggaatggagg caagtgaaag gattggaaat  30780
ctgttttgga aataaaacca agagtacttg ctaatgggtt gggttgggtt gggttggatt  30840
ggattggatt ggattggatt ggattagatt ggattggatt ggaggaggaa ggcgtgtgag  30900
cagaagagga aaatcaagga tgatgcttag gttttgtgct cgactgagtg tatgaagtgt  30960
tcttatgtta gatggacaaa actggaagag gacagatttg ggatgaaatc aagggctctg  31020
attcagacat tttctttaga aattgtgaac tcctcaggag gtatccagtg gagacggttg  31080
ggtatataag tggagctcaa gagagaagtt tggctgcaga aagaaagttg ggagtcatca  31140
acatagaaat ggtattgaaa cctgcaggac taataaaata atctagcaag agagtagaga  31200
taaagaaaag aaggccagaa tcgagctata gcaccgtcac acagttagtc tgatagagta  31260
gaggagccaa gaatggagat gggaaaagat cagtaatgag gtagaaggaa aattaagagt  31320
gatgtcacag atgtcaaaaa ggggagtggc tcaagaaggc agttgttttg ggagtaccca  31380
```

-continued

```
tgaccaccta ctagtgattt gctggaagga ctcactcacg actcaatata gaatcatatt  31440
caaggctaag atttattaca gcaaagggta tggtgcagga acagcaggat acagatatat  31500
ggtggcaaaa ctagagaagt cgtagtaggc tttcttgtcc tctctctgta gggattccac  31560
atgtttctca ggaatgcatg tttctctcca gctgtaaact gcagagacat atgcaaaacg  31620
cctccaccca ggaaagccca ctcaagtctt aggggttcag agctggtcaa gggagctggt  31680
cgtgtagcta tgtaaccagc caggatgcag accccaaact aggtactagg atgcatcagg  31740
aatcttcatg tcaactttaa acaatgatac tgtcttgata tattttgacc actgccttga  31800
gggcacaaaa ataacataac taattagtaa gcatttcagg gagtttagtg ctcaggattt  31860
gggtcagggt cattgctgtg actgcaggtg ttcccaaaga caagcaagaa ctgagtaaaa  31920
catactggct atgttaactc tttcctctag aggtcatggt taatgttgaa tgcaggtgaa  31980
agtcaaaact gagagccata aagttaattt ctatatccca aagtatagtt agtgaaatta  32040
tatttctctc cagatagatt cattccactt atttagtaaa catttattga atgcctaata  32100
tagttcatgg catgtgctag catgagacta taggggtaaa taagttagac atggcacctg  32160
ccctgaagga gttgacaaac caataaacgc agatgtcatt agctgtgtgc gagaatatga  32220
cagaggtctc acggctgaga cctgaaggat aagagatcag ccaggtgaaa agggaaaggc  32280
gaggcaataa atagcacgtt caaaggcctg gaggtgaagg agcatattga ctttgaggag  32340
caaaagaagt tcagtgtggc tggaggggag aaaggagaag gtgagtgtgg ggtagattat  32400
ggaggacctt atacaggctg ttaaacacgt tttgcttcat ccacggggag atataatcct  32460
aagggttttt gcttgatagg aaaatgacag atttgttttc ttgattgaaa aatttctgat  32520
aattttacag ttagttttgc attgcaacag agattctctc tctctctctc tttttttttt  32580
tttttttttg agacaagagt ctcgctctgt cacccaggct ggagtgcaat ggtgcgatcc  32640
cagctcactg caacctccgc ttcctgagtt caagcgattc tcctgcctca gcccccgagt  32700
agctgggatt acaggggtgt gccaccatgc ccagctaatt tttgtattta tagtagagat  32760
ggggtttcac catgttgtcc aggttggtct cgaactcctg accttgtgat ctgcctgcct  32820
cagcctccca aagtgctggg attacaggca tgcaccaccg tgcccagccc agagattctc  32880
tttaagaaat ttggtgcaac agtcatttct gggacaaaaa gtagtgagaa aatacaaaca  32940
caccagggta aataaaccag agcgccacaa aatgtaatat taagtgtgta aaaataataa  33000
tccctgagag ctatcagtgt gaaaagtttt tatttgaatg ccgtaattga atggaattgt  33060
tcatttaaac cttcaagtga atttattttt atgtctaaaa cttattagaa atgtttcaat  33120
ggtgattata tgtagtttct tttttgcctt caacagagca cagatcacac agaaaggaat  33180
gatttttttt ttaatcagca attttggaga caaattctat gaatgccaac ctatacagaa  33240
actgacaagc attaattatt cagaatgtaa agagaaatgc cagagtatta aggaacagat  33300
acctagattt aaacataatt ttggaatatt ataattatta tgaattacaa ccacttatat  33360
ttgaggcagt atgtaacagc tgtgtgcgtg agcaggaaca tgagagggaa cgtaacctgg  33420
tctcattttc tagacaagcc attcaagagg agcaaagaga gtgggaaaat gaaagcaatg  33480
ccactactga ttattgaaca tctttatctg ccatgcactg tgctaggccc tttacacatt  33540
ttccttcttt aagctattta aaaactgcga taagttcctt acattcccat tttataggca  33600
agagcaaata gattttacag atgaagaaat tgatgtccca aaatgatatc ttggtaggtg  33660
atagattcgg ttcggtaacc caaatgtgtc ttttagcgat ttatgtattc attcaacaaa  33720
```

-continued

```
tattcattga gttcctactg tctaccagaa cttttgtaag ggatgcaaa gaagaacaga  33780
cccaggtctt tccctttatg aactagggca gtgggcctta cacccaactg ccgtaatggg  33840
aaaagcattg taatggggct ttgttcgtta cagtcaacag tgcagtgtag ggatgctttg  33900
taagctggcc tacagggtga ttggtaaagt tgagaaaggc ttatcaggga ggctgacatt  33960
tgaacaaagg tttggatatt accaggcaga gagatggagg tggtaggaat tccaggtaaa  34020
gcgactggga aaacacatgc tgtgcttggg tggcaggagc agtccaggga ggacatggtg  34080
ggactgtgct gcaagaagcc ttgtatgcca aggagatgag acttcccttg tacatacagc  34140
caaggataag aatttgatga cgatttctaa tgtatcttag catctaagtt cccttaattt  34200
gtgctcactg gaaaccacag agttttagaa ggcttttgtc attgtggttt aaaagaaaaa  34260
aatagattgt tcaaagaaca gtgatacata gggaaaatat tttgactcag gaacgtaatt  34320
tctcactaaa attggcaata tttgtagccc catgggaact atgtttccat aggacattct  34380
gttcgctgtc cttgggaagc tatctaaaaa aagaagaaaa aaacacaata aaaagaggta  34440
tttggggatc agtaataaaa gttgtatact ttattgaatg tgttactgtg tactagctac  34500
ttatccatat tattttaaat cctgacacct attaaataat aggtagtatt atccctgttt  34560
tacagatagg aaactgaggc tcagaaaaaa gtgacttgcc tgagactact tagctagtaa  34620
ggagcagagc tgggaattca aacccaggtc tgtcaggatt caaaacccca gttcttccag  34680
tctctagagc ctggtctcta gagcctggag acttctgtgg aggtgaccta ggccacttca  34740
ataggtgagg agacagagga ccgcttgggg atgcattcct taaatcagag cagctgattc  34800
tatgaatgcc aacctaatac agaaactgac aaacattaat tgttcagaat gtaaagaaaa  34860
ctgccagagt atgaaggaac agacatctag atttaaacat aattttggaa tattgtaatt  34920
attattaatt acaaccactt acatttgagg tagtgtgtaa cagctgtgtg catgagcagg  34980
aacttgagag ggaacgtatc ctggtctcat tttctaggca agccattcaa gagcagcaaa  35040
gagaatggga aaatgaaagc aatgccactg ccgattattg aacaccttta tgtgccatgc  35100
actgtgctag gctctttaca cattttcctc ttttaaatta tataaaaact ctgtgataag  35160
ttttttaag tatacagact tttgtgctaa attggaaaac ccgtactgga acctgggggt  35220
gggggcgggg cagaggtctt ctaatgactg gccttgtgct ctttaagctg cactagctat  35280
cccactttga aaagaatgtg tgaaacacag ttgcagtcat gcatactcca tctccaaaga  35340
atggattcat tcttcaggcc atagtatact gactataatt ttctgtttgt aattacccag  35400
attccaagcc tgtttatagc atttatacct gaggaatgga atagtgagga tttgaagagg  35460
ccgcagtcct tgaggttttc tttgataata atatctgtgt agctgcatca aacacaaatt  35520
tgatattctg tgtatctgta gcacaggtca tgtgactgta aattcttttg atatcttgtt  35580
gcatactgag gtcaaggaac tggctcttga tgtaattccc cgcatcctca tgggagttgt  35640
taccatcata ctctggaaaa caaatgctga gatggattaa ctttttacac tgggtttccg  35700
catgggattt tataggaata aaggttccac taccagcagt gagtagcctg aagtctgcca  35760
cattgaccag gaacctttgc aagaataaac cgaggatgtg ccctctgcag gtgaatgtgc  35820
taggctctct ggggttgcca aggagtttga gtccccatcc ttgagtcccc atcaactaca  35880
tctagttgat gtacacgtga tcctttgcaa aggttctgag ccctctaaaa ctgatcaaaa  35940
ttgcatctgt tagaaaatat taaatatatt ctatatatca agccaaatac taggagcttg  36000
tgtaagcaac agagtatctt ggtggatcac gtgggtgttg ggttaggcaa aagatcccac  36060
tgttggccct ccccacaccc acatccttac tatgctctgg gcagacagag ttactccaac  36120
```

-continued

```
tatctcaaaa tgcccagaaa cccttaacca cctctactga tttgcctgta ttcaggagcc  36180
tccttcttca cagctgagat tcagacttca ttgagggaca aggtgaatga gagggtaggg  36240
gacagtaggg ggcagaatct ggtcatcagg aactttggac tttccagtga gcacagactg  36300
agatacctca ggtgctaaga ctgcagcacc cctggaggaa gactgtacac tagacaacaa  36360
caaggctggt tggcaggaca gcatctaccc agcatcctta acatccggga ggagatgatg  36420
gtgccgtgta gggacacttg accctgccca tagcagcctc agcccctgtg catcctggga  36480
gtgaagtgat caggtcatgc aagtaactac atcagtcctc accactggga tcattgctac  36540
agaggggaag gcttttccct gtgtgttgga gatggagata gaagtgtatt aatggaggaa  36600
aacaaaataa gcttttacat ctgctaaatt aacagaatcc caggctgcca aaaccctgag  36660
gcttgctcaa tcagcagtcc aaactgtatt tcctctaagg gacaaattat gagctgctgt  36720
aaaggtacac acagtctagt gagaaaccat tcaattttga gggggaaact ctagggaaat  36780
agagtaagtt aaaggagtag agtgtgccag tatgagaagg caactctcct ggagtttgag  36840
ttccaaaact cagtgggctc ataggtcatg gtgtgatctt agaagtcata agtgaccaac  36900
aaggagttta ataacgcctt ttcttatact ccctcttttt acatagcctt tataccaagt  36960
tatcatctgg cagtcatttt agatataggt ttctaagtta gacggtaggg tccaaatgaa  37020
gtgtttggca aagtcatctt aattttttaa aacttgatat gaaaaagatg gtggtatcag  37080
gtattgaaat tgaggagcta tcagaatagg gaaaaattcc ccatttatgc ccatactcac  37140
aaatacacaa atatttataa acaataatga tacaggcagg catggtggct cacacctgta  37200
atcccaccac tttgggaggc caaggcaggc agatcacctg aggtcaggag ttcgaccagc  37260
ctggccaaaa tggtgaagcc ccgtctctac taaaaataca aaattagccg agtgtgttgg  37320
cgcatgcctg taatcccagc tacttgggag gctgaggcag gagaattgct tgaacccagg  37380
aggtagaggt tgcagtgagc tgagatcgtg gtattgcact ccagcctagg caacaagcgc  37440
gaaactctgt ctcaaaataa taataataat aatacaactt atttttttcc ctttgggggg  37500
ctttccagca aaaaccagaa agcctattag acaaatttta aaagagctgt aacactataa  37560
taagactgtt taataatggt tgagaacaca gagcccgaag aacacagatt gcctgggttc  37620
aaatcctggt tctgctgttc agtggctgtg atcttgaact actgtcttac cctatctgtg  37680
cctagttcct attttgtaaa atagaaataa tagttctacc tcgtaggttg tcgagagggc  37740
taaataagtt aataaacata aagtgctcag aatatgattg gcacataagt gctatggaaa  37800
tatatgctac tcttactgca gttacataaa ttgtgatatt tggcagcctt gaagcgtggc  37860
cctgccatat gctttgtgtt taaaaccctc aaactactgt ttattgaggg catctttgat  37920
gtcaggcaca gggctaggca atgttcctgc tgtatctcaa tgaatctaca caacacccta  37980
tgaggtaaat accaatttac agctttagat actgacttgc cagtggttaa gtaacttgcc  38040
caaggccaca aagcaagtac ctggtagatt caggactgaa gcttcaagtc tagagagctt  38100
ggctccagcc gcagctgcag tttgggctga ccttgttcct gccagcacac tttgggacct  38160
gggccataca agttatagca tcctggacag accctctatt ttatagaaaa ggaacctgag  38220
gccctaggat taaatgaatt gccagaggtc actctccaaa gagactctga ggtccagatt  38280
aggaaacctg aactaacatt gaagccgtgt ctttctgtat aagatccaac tgcttgtggt  38340
atgtttggcc aaaaagactc aggttaaagt cagataccaa ataatatatt gacatctagc  38400
atatttatgc ccagatgccg tatagcaaat catccttcac tttaattagc ttatagttat  38460
```

-continued

```
atactcgaca atgtgaatga acagagaaaa acaaggtatt ttttttttcat cttctaaatt  38520
tgcttgggaa attcctccgt gtcttttaca ggtttaaaaa tcatgtttaa cgataatgta  38580
gttatcttag gaaaaagacc aacccatttt tatcactctt tatcattggg ccatcacaga  38640
tgagagcttt ctatcttata gaatcatttg cacaaagtat atatgaggat atacagcatt  38700
gtatttgtag catttcttat aatagtaaaa aaatgaaatg atacagtcat ctagttaatg  38760
ccactgagtt gtacacttag aatggttaaa taacaaattt tgttatatgt gttttgccat  38820
attttaaaaa aataatagtt taagaaacta gtgacttgta tacttaaact gagtggattg  38880
tatagtatgc aaattatgtc tcaataaaga tattttttaa aacccataca tttatccata  38940
gagaattggt cagattatgc caaacccagt caatggagta ttttacaacc tttattaaag  39000
aattaggtag atttatatgt tttgacatgg gaggatgtcc agaatatatt gtgaagtaaa  39060
aaaaaagttg atgtgcattt ccatatgctg tatacacacg tctacagttt tgtcttatga  39120
gtaacactct tgtaaatgtc attatgcaac ttggcttttt cacttatgtg tgttatgtta  39180
gaggttagta catatagaga tacctcattt ttttaactgt ttcaaactat tctgtggtat  39240
aatcttatct tagtttattt agtcatttcc atattgatga gtctttaggt catttataac  39300
ttttagatat ttcgaagaat gctgcaataa atactgttaa acaagcacat tagctccata  39360
atttcccaag ataggcacta ctaaatcaaa aagtacatgc atttttttcc tcaagtttct  39420
ttctttcatt gatgatgctc ttcttcctcc tcttcttcct cttcttcttc ttcttcatta  39480
ttattattat tattatactt ttaagttctg ggttacatgt gcagaatgtg caggtttgtt  39540
acataggtat acatgtgcca tggtggtttg ctgcacccat caacccgtca cctacattag  39600
gtatttctcc taatgttatc cctcccgtag cccccccacc ccccaacagg ccccagtgtg  39660
tgatgtttcc ctccctgtgt ccatgtgttc tcgttgttca actcctactt atgagtgaga  39720
acatgcagtg tttgattttc tgatattctg atagtttgct gagaatgatg gtttccagct  39780
tcatccatgt ccctgcaaag gacatgaact catccttttt atggctgaat agtattccat  39840
ggtgtatatg tgccacattt tcttaatcca gtctatcatt gatggacatt tgggttggtt  39900
ccaagtcttt gctattgtga atagtgctgc aataaacata tgtgtgcata aaaggtatat  39960
gcatttttgt gcttgatgga tactgacaga ttaacctaca agaggatgta ttatttacac  40020
tcccagcccc acgtgagtat gtgtatttcc ccacatccta accaacacta atttttttcc  40080
attctaatgg gtgaaaaaaa aaatctccat tttaagttgc attttcactg agcatggtgg  40140
tacacaccta cagttccaga gacttaggag gtcaagatgg gaggattgtt tgaggccagg  40200
gccaggagtt caagactagc ctgggcaaca tagcaagatc ccatctctaa cgaaaatttt  40260
tttaaaaact agccaggcat gatggtgcat tcctgtcatt ccagctaccc aggacaccga  40320
ggctggatga ttgcttgaac ccagggccat ggtcccacca ctgaactata gcctgggtga  40380
cagagcgaga acctatctct acttaataat tagtagcatt tacatgattg aaaatcagaa  40440
tgaacatgtt ttcacattaa ttcaacatta gataaacatt gaggtactgc cccagatgaa  40500
caaacacaaa cccctgcccc tgtggaactt ctgttaaact ctattggtca tttctatttc  40560
ctcatgccat ttgcctgttt ttctatttat tcatgctttg ttatgtgtgt ggcaaatatt  40620
ttcacctctt ctgtggcttg tcttttgagc tccattttca gtatctttgg ccttacagaa  40680
gtttttaatt tttatgagat cgtattcgtc agtccttttc tttatgcttt tatgttccat  40740
gcctcactta aaaaggccct ctttccccca aggtcataaa tatattctat accctttca  40800
atatttttat ggttttagtt tttatgttta gcacctaact ccatctggaa tctatttttg  40860
```

-continued

```
ggaatcgagt ggtatgtaga tagatttcat gtctgacaat atatattttt gagcactcaa  40920
atttttaaaa agtatgtatg actttggtaa gcagaaagag ccaagaggag tttgaagaga  40980
cactcagaaa gtggatgtcc attctgggtg ggcccaggag tttgcaattt tagcagatac  41040
ctccagagaa aagagaaagt gatgagaaaa aaaaaaaaaa agctgtgtcc tgtggagtag  41100
attcaggtca taatggctgt aggtagagac acagcagaaa gagtagcccc gggttggcct  41160
tgtatcctgg tacctacagc accttaggaa atacataaaa tacatgaaat gtcacagctt  41220
tgcaagaact agaagaccag ccagaatgaa tcagagaagg gattcttcag tgtttctact  41280
tgtaatggaa tttttaatcc ctcatctggt acaaaaatga gtttgagata atagtccatt  41340
taaaaataac ccaagccggt gtggtggctt acgcctgtat tcccagtact ttgggaggcc  41400
gaggcagggg aatcacctgt caggagttca tgaccagcct ggccaacatg gtgaaacctc  41460
gtctctacta aaaatacaaa aattagtcag gtgtggtggc gggagcctgt aatcccagct  41520
acttgggaag ctgaagcagg agaatcactt aaatccggga ggcggagatt gcaatgagcc  41580
cagatcgtac cactgcactc cagcttgggc aacagagtga gactccatct caaaaataaa  41640
taaataaata aataaataac caacccagcc ctggattaat gatgaatttt cattctggct  41700
agcaaaggtt agcaaaagtg gatgactaca tgtaggcatg ttaattaaca ctttttagat  41760
tctggaaaaa gaatgttgtg tggcagaaat atgggtacaa atgtgcaagc cttctgtaga  41820
tgattcttta aaggcaggtg gagtgggagc cgctgggcta acctacccca aatcactgca  41880
cttcctttct tcccttgtca ttaaaaccat atgacccctt tagtgtctgt gttgcactca  41940
tgagttcaga agttccaatg catctatcaa acacatgtgt ttgcctactg tgcatgttgt  42000
tctaagtgct ccttcactgc ttctgacaac cctatgaggt actattataa gcctcctttt  42060
acacatgagg aaactgaggc tccagagagt taaataagtt gcccatagtc ccacaggcag  42120
tggtggcatt gggatttgga ctcaagttgt ctagctccag gttcgcagaa tcaccctaat  42180
aatgtgccct ccaaattggc tatttcagca actgcagtgt tcaggaaaga attatactct  42240
gatgagcctt catgaggcag ggttgaaaaa cctgtgtcag gaaaagatat gacaccttac  42300
tggttatcag accatgctag aaggagcctc tttaaaatcg aacaacagag ccactgctct  42360
ggtgcaagca gcactctcac ccagccctct gacctcagtc acagtgtgag ctctatagtt  42420
cctggcaaac tttagccatg gggtcaaaaa tggagaagcg tgccttcagg tataagatgt  42480
gatgtgttca tgcagggatt agctctgttt aggcttaatt ctggaagcca gggttcttaa  42540
tttggttccc attccctgac ggaatactat gcagtcctga taatgaatga tttacattta  42600
tacaacagta tgcatggatg caccacaggg gacagtgcct ggaaataggc acaagggtgc  42660
tttgaggctg ctgtctacac aaatgtgtgt ttagtttatg aaaatccaca gtggcgcctg  42720
taatcccagc actttgggag gctgaggcgg gcggatcatt tgaagtcagg agttcaagac  42780
cagcttggtg aaaacccgtc tctactaaaa atacaaaaca attagccagg tgtgatggcg  42840
gatacctgta atcccaggta ctcgggaggc tgaggcatga gaatcacttg aacccaggag  42900
gcagaggctg cggtgaacca agatcgtgcc actacactcc agcctgggtg acagagtgag  42960
actttgtctc tcaaaaaaaa aacaaaatct acagtgagct cttcagcata tagctttctc  43020
tgcatattgt attccatgta ttcattgtac tggattcaat gtacagtatt ctatgtatat  43080
tgttatttca ctgaagagtt ttttcttaat ggcgtgaatt agagtcagct gaggtatttg  43140
tgaaaaatgc agactcctga actcacgcct caagattcct gttctggatg gggcccagga  43200
```

-continued

```
gtttgcagtt ttttacaaat acctcaggta attctgctgc aggtcatctg aagatatacc  43260
tgtaagaaca tagcaaagct gcagacctgg tctgctgttg atgtgcttaa tactgggcat  43320
caataggact ctataagtag agcaaaagaa tgacttgaga atgactaggc tcacacattg  43380
ggatggtagg aaaacagcct ggtgcactgc aagggtaaca ccatcttgaa gcgaaaccac  43440
cacgatgacc gatgcttgag tcctgcatgc caaggtgttc ttgcagcaag gccaagaaac  43500
aatgcctgta gcacagataa cccctcataa acatgcttat ctgacttccc cagtggtcac  43560
cagtgttccc caggaggatc tgagacatga ccagctgtct ttactctaaa cacttgctat  43620
ataaaggatc atttctggtg ggtggacaca gggactcact ttctggagca gcccaagaca  43680
tcgcttctat ttgtaagtcc ctattaaata ttttttctga agaactggat ttatcagcct  43740
ctttcttaag cctcttagtt ccctctgcct ttgtgggtag gtttgcgtag acctactcac  43800
caagaaacaa ggctatatct tacatgtatc catgattttt tttaatgcac aaaaatgtaa  43860
aaagactata taaaatacct acaacaagat ttctgttggc caggtacagt ggctcatgct  43920
tggaatccta gcattttggg agggtgaggc gagtggatca cttgagccca ggagttcaag  43980
accagcctgg gcaacatagc aagaccctgt ctttacaaaa agtacaaaaa ttagctgggt  44040
atggtggtat gtgcctgcag tcccagctac tcaggaggct gatgtgggag gattctttga  44100
gcccaggagg tggaggcagt ggtgagctga gatcacacca ctgcactata gtctgggtga  44160
cagagtgaga ccctgtttaa aaaaagagag agagagagaa aaaaaaagat ttctctgaat  44220
ccttctcatg cgtatcatga gagatgtttt aaaatgtttc tatattttgg ccgggtatgg  44280
tagttcacgc ctgtaatcct agcaccttgg gaggctgagg cgggtggatc acctgaggtc  44340
aggagttcaa gaccagcctg gccaacatgg tgaaaccccc atctctacta aaaatgcaaa  44400
cattagccag gcgtggtggt gcatgcatgt aattccagct actcgggagg ctgaggcagg  44460
agaattgctt gaatccggga ggtggaggtt gcagtgagcc gagatcacac cattgcactc  44520
cagcgtgagc gacaagaatg aaactccatc cccccaaaaa aaccactttt ctgtatttta  44580
atgcacagtt taaaaatgcc agacctggct ctattctact taggtttctg ttcattagat  44640
aggagtcatt catgtatgac tgaatcacta tgaggatcct cctctctctc ttcttcccct  44700
tccacccaca tgccaggctg tggttcagac tgccttctgc tttctcacgg gtctctgttg  44760
tgtgatcttg tgcccacctc tctgtgtgtt aaatggagag agtggcttga acagtaccct  44820
catggttggt cttcaagagc tcatctaatt ctgaatggta gttgggcatg tctgaaggta  44880
ttagcaattc tgttgctcag cattgctgat gtattgagca atgtgaaaac cttggcgaat  44940
cttgttgcca tcttccccta agaatctgcc tcatcctgaa gcccaaccat ttgactctgt  45000
ggtaaaatga agtaacttca gtaaggtcca tgtctaccaa tttcttaatc tcatttgagg  45060
taaatagatg cacattatca gaaaggactg gccactatgt actgcaaatg atgggcacag  45120
agttgtgatt gtcccagcag acttgagatg agctagggat acatcagtcc attatgagac  45180
ggtatctgtt atagtcaaga gtgtctctgg aatggcttct tgtaattatt tggactttct  45240
accaaggttt ctgtgccata gcctatggaa aagtagattc ctttcaagag acctgacttg  45300
ccaagcatgg tggttcacac ctgtaatccc agtgctttca ggggccaagg cggtgggatc  45360
acttgaaacc aggagtttag gaccagcctg ggcaacaaag tgagaccccc atctctacaa  45420
aacattagcc aggtatagtg gcgcatgcct gtggtcccag ctacatggga gggcaaggcg  45480
ggaggatcac ctgagcccag gagttccagg ctgcagtgag ccacgttcac accactgcat  45540
tccagcctgg gcaacagagc aagacccagt caaaagaaag aaagaaagaa agaaagaatg  45600
```

-continued

```
agagaaaggg agggagggaa gaagggaggg agggacggag ggacggacgg cgggacggac  45660
agagggaagg agagacagag ggagggaggc ctgacttgta tatttatgtg cacgaaatcc  45720
gttctaggcc tctgaatatg gcacctggcc cactctttct tgagaacagt ttgccagtga  45780
gcaatgtgcc tcatgtcctt tgtgaaactg gcagagcata aattattaat ttaaaataca  45840
caaactaaga tcaagataag atgtgcttta atgaacgggt aaactcaaat ggcttattaa  45900
caccttcatt tcctcatgct gcttctgaaa tgggcatttc tcaacttaca ttttaaggta  45960
ggagctgatc tgagatgcaa gttaattata cagtttgtcg aagccaaaga gttgggtttg  46020
ggagattttc tgacctgaaa atgttcagtg gcggtgccca tgtaatcttg ggcctactct  46080
gacagacagt tcagagcctt aacattcagt gttggtcctt tggatatatt gaacataagc  46140
tacagtttac gggtatgaga ggacattatt gactgagact tcaatagttc caaaggggga  46200
aaaaaagaga aagatggctt ttttaaagct actgtcttca gctcaggaaa aaacatgtga  46260
tcagccgact gtaaatgcac agcttgagaa atttagcaat tcccaaaata ggttcaagtt  46320
tctttgtgag catgtaggcc tacttgcagg taacattgac tttgttaaca acgtttgtta  46380
acaataacat tgtaggcagt taatgtctca gagctcttat agatacaaaa gaaaataaac  46440
ttacaacttc cagaaagcat cttctcattg atgagtctaa ataatgctca tctattggag  46500
aagcaacttg ttaatagtga ctttttgtca cttttgtaga gtggggagag ggacatggga  46560
gatgaagctc ttactttatt tgggaagtga gatgtctcaa gttctttatt ctaaaaaagg  46620
taaacatcag ttgcctctga ggtagtaata gaagaaggtc tgttttactt tggaggaaca  46680
ttaaccttag agtaaaacaa acgaaaacac agttcaaagc ccaggctgtc tgagcccatc  46740
tcgtcatttg taaaatgagg ataataatac ctgccttact tatctcatgg tgtttctgtt  46800
gaggattaaa tgataaagca ctttggaaat tatgtaaaat atctgtattt taagcaggta  46860
tgatttcccg aaatccttga gtttttcctc tgattccatg attatgacat cacttaaata  46920
tgccacccct ctgctatcct aataccccaa atctcagtga aacactggaa aagtccgaaa  46980
ccaatagaga tttctaaagc agatcccctt attatgcccc tcaattagtg atcattgtta  47040
gtgggtctgc tcagagcatc attgccaagt gctttgataa gctgaagaaa tctgttgata  47100
atttcttgag gcatggtatt tcagtgtgtg gaatacttgg gtactagttc ttgggagttt  47160
tttaaagtaa aatacttata tttgtgttga ctttgcaaca gcaggtacag caaatttcac  47220
atggtacctt gctacagaaa ttaattagta ccactcatgg tttaaattat gtagaatgat  47280
agtatgctca tattcttctt ggctgtctta aaaatgaata gaaacaaaaa ggtaaacaaa  47340
gctcatattt acctctcctt ggaaagaggt tgagtgattg tcatgtagct tctcatttat  47400
caagtatgtg ttatgatttc gttaaaggat aaattgaaag gattcttaaa gcaacaaagg  47460
tttggtcctg cattgatgca tattaagtaa agtagagctc ctcagttggc attcccaggc  47520
tgggtgacac agaggtgcct ctttctgata ctctccttcc cagctcctgt gccatcccct  47580
cccctctccc cttctctctc ctctctcccc ttcttctcct gtaatacttc tgctacttgc  47640
tctgttctac ccagagactg aaggaagtga gtggtgatct aattgagact gaataagtcc  47700
gaacatttat tttccttccc cttcactcca tccaaagtcc aatcctgagg aagacatgga  47760
ggttatgatt aaacttgccc aacactcaaa ctttactgac tgcttattct tatgttaatc  47820
acttggcctt tgctagatta atgactgagt gaccagaagt ctcaatgatc ccataaatcg  47880
tatgatttta aactatttgt gtagcttttg ctagttgtaa taaaaatttt cacatgattt  47940
```

-continued

```
tttttccaaa tagagaggtt taataaagct aatgtgcttg accaggtttt ggagagttta  48000
catactaatt tcttaacccc tttctaatat ggttagtata gctctgtgtt ttcatcagag  48060
agaagcagac tgtgaattcc tcaccttggg gcttccattc tccctccagg tggcctcacc  48120
tttcaggtga acaacctgac ctctctggct cctaaatccc acccttacaa gccgcaggag  48180
ccggtgcatg gggcatagt ttcttacctt taccttttc aaacctttcc ctcctcacca  48240
gctttttttt aagactttat tttcttagag cagttttaga gcaaatttgc tgtacctact  48300
gtggcaaagt caatacaaat ataaatattt acttaaaacc caagaaccag tacccaaaag  48360
caaaattatc taaagcaaaa ttgagaggaa ggtacagaga tttcccacat accccttgtc  48420
cctatcccca cacgcgcata gcctctccca tgatcaatat cccccaccag agtggtacat  48480
ttgttacaac taataaacct acactgaagt aggggtttgg acaaatgtat aatgacattg  48540
tagtatcata cagaggagtt tcactgccct aaatacccta tgtgccatct tttcatcctt  48600
ccctcctcac tagcctttgg caaccactga tctttttatt gtctccataa tttcgcctgt  48660
ttcaaaatgt catatgcttg gactcatata gtatagcctt ttcagattgg cttcttttac  48720
ttagtaatat gcatttaagt ttcctccatg tatcttcatg gcttgataga tcatttcttt  48780
tcaacactga ctcgtattcc attgtctgag tgtaccacag gttatttatc ccctcaccta  48840
ctgaaggacc tcttggttcc tttcaagttt tggcaatgat aaataaaaat gtaaatagct  48900
gtataatttt tatatggacg taagttttca gtttattttg ttaaataaca aggagcttgt  48960
ttgctggatc atatggcaag agtaggttta gttttgtaag acacttgcaa actgctttcc  49020
aaattggcca ttttgcattc ccaccagcaa tgaatgagag ttcctgttgc tccacatcct  49080
cgccagtatt tggtgttgtc agtgttctga atttttgcca ttctaatagg aatgcattga  49140
tatctcattg ttgttttaat ttgcctttcc ctgatgacat atgatgtgac atatgatgac  49200
atcttttcat atgcttattt gccctctgtt tatcttcttt ggtgaaatgc ctgctgtttc  49260
catcttttgt ccatttttta attgagttgt ttattttctt attgttgggt tttcagaatt  49320
ctttctgtat tttggataac tctttcatca gacatgtctt ttgcaaacat tttctccaag  49380
tctgtggctt accttttcat tctcttgatc cctccagctt tttatttaga aaattttcag  49440
tcctatagaa aaaaatacaa aaatagtaaa ataagcactc acacattatt catatacatc  49500
caccagttgt taatattttg ccacatttgc tttatctctc tcatgagctc catctgttga  49560
ttttactgaa ccattagaag tgataaatgg catgtcacat catcccaaaa aacaccaata  49620
tgcatctcct aagcatgact tcttactgcc taatcatgac acatcattat taaactaaaa  49680
ataataactc agtaatatcc aacaacatac tgcattttta aagttctcca gtagttccca  49740
gaatcaaatc aagcaaggct cacccatcgt ctacagtctc acaatctagg acagttcccc  49800
tgcctttttt tggcattgac cgattcatat tgaaccaatt ttatgtcatt ggttgattcc  49860
taatgaacca tttccttgtc tacaagctct tggcttgccc tcttacagtg atgagttgga  49920
gtctctccat gacagcacca gactggaaat tcttaacatg ctttccaggc tcattaacat  49980
tgagatagtc aaaatctaca cgatgtcctc aataattttg agaacaggcc atgaaagaaa  50040
atgttgtgaa aaatgtgttt atggttaatg attcaacaca gttaacagag gtgacttggc  50100
tttctgccct gccctcatgg caacatgcgg cttcccagtt cagcactgtc ctctgctgtt  50160
agggcctggg aattctgaat gagattcagt ccttggagtt gaaaaagtaa tttacctgat  50220
gcttggtggt gtgaatgttt gtgacagttt ttgtgctaat acattttgaa ggacatgttc  50280
tctcaaaata gccccttcca ctttctgaat ccacactcca gttttctttt taacttcagt  50340
```

```
gagtggtagt ctatttgacc tgatgtgcag atcttctggc acatacattt ctgctgtctc  50400
ttggcataac aaattggcag tctatcccta tgttatgtac actgtttata ttgaaaattt  50460
gtctttaatt ggtctgatac tacatcatct gctagggcca gtagtttgtc atcagccaat  50520
ttgtacacct gaggccctca aacaaacacg tgcttacaat gtttctggca ctatttttaa  50580
agcttgtaag aattaaatga gatagcacaa caaccccatg agggtaagta ccgttaatcc  50640
cataaatatgg atgaggaaac tgattcattt agagggatta agcaatttgc ccaataccac  50700
atggctagta agtgacagag ctgggtttta gctctgacac tttgattctg gaacctgcac  50760
atttcatcat tatgtcagat gccctgaaga ggatactgta tatcatctca tctcacatgc  50820
tgtgttcagg caggtgacgt gctgctcaat gctggttttg atgtctttac taaactactg  50880
atctattttt gagatttaaa tctcaaaaca gtgatactag tgagaagtag tccacctttg  50940
ttaatccacc aaatgttccg gttagggaac ctaattttgg taacttcaag gcctctcctg  51000
ctattgggag ctaagcatcc ttcactctgg actctcactt gcttcacttt agaatgagag  51060
ctttttaggg taaaactcag gaagtaggat gactgaaaga aaagcctttc ttctccacag  51120
tagcttatgg ggaaactagt aaattaattg ccattattcc ttgccactaa aggatgagtt  51180
cttatggtag caataaatag acaatagggc tgtgcagacc tccaacaaac tgtcttttct  51240
ggggtcaaaa ggggtctgaa ttaacctctt cttaaattac agctctgtga cacctgcagg  51300
cactcataac aaataagaac accaggccag gcacagtggc tcatgcccgt aatcctaaca  51360
tcttgggagg ctgaggtggg tggattgctt gagctcagga tttcaagacc agcctagaca  51420
gcatggcaaa accccatctc tacaaaaaaa aaaaaaaaat acacaaatta gccaggcgta  51480
gtggtccatg cttgtagtcc cagatactca ggaggctgag gtggctgact tgagccctgg  51540
gaggtcaagg ctatagtgag ccatgattgc accactgcat tcctgcctgg ctgacggagt  51600
gagaccaata gggcagcaag aaacaaaacc tcaacactga accggaatgt ccatgacata  51660
ctgtaaaaaa agaaacctca aatggacaat aactgtatag tgctagttgt aatgattgtg  51720
cctttttttt tttttttttt tgaaacggag tctcgctctg tcacccagac tggagtgcaa  51780
tggcacgatc tccactcact gcaacctctg cttcccgggt tcaagcgatt ctcctgccca  51840
agcctcctga gtagctggga ttacaggcac acaccaccac gcccggctaa ttttttgtaa  51900
ctttagtaga gacgaggttt ccccatattg gccaggctgc tctggaactc ctgaccttgt  51960
gatctgccca ccttggccaa gaaatctctt taagtattca tttgtacttt aaggtaatgc  52020
tcgatctcgc tcttagtaca gctgaattgt ccttcaaaaa gatgatctgg ttatgtttga  52080
cctcttcctc aagggaccaa aaagggaagt tctcagcttt ttatagtatg aggtccctag  52140
aggttttcac tttggggatt taaaaacaag tttcctgtag ctatatggag gaaaaaaaaa  52200
aaaaaaccta aaggggaaca tggaagaatt ataatgattg gggcatgata attatgtcca  52260
gtttttaaaa ctccattctt aaaaatgtct tataatttat aggttaaaaa tttaaatgtt  52320
tagaggaagc aggacaggtt tatgagtctc tgacctggga atggagtggg aggaatagag  52380
aaggtggggt tgcaagagga gaaaggcaga ggaatttcct accgtcttcc tgttttttgt  52440
tgatggttag tgattaatga gacaagctgt tctgtttctc tgggagtctt gactgtcttg  52500
aagaaaaaaa agaaaattta ttgcaaccca atgcagcttc agatttttcc tctatttttt  52560
tttttcaatt aaaaacgtaa ctgtccctaa tttaggaact gaaattccca aacctcccca  52620
ttcacctatt caggaagaaa tgaaatggaa cctaacatct acatttcttg ggtataatat  52680
```

-continued

```
caaaacttta atactatggg gatgaacatg taagcaaatg caactctatc tccccataat  52740
gttggaagaa tctaacttga aaccagacat ttggtttgga tcttggcact ttcttgcatg  52800
gaaatattcc aagaaggtgc attgactctt gatttgatct agaaaactgg gttctttcca  52860
gagcccaccc aggatggcac ctcatagact aactatggac ttttccatca atactggaaa  52920
acagtttcat ctaatccccg gaccaaaggt gactcggact ccaagtgagc ttcctcaggt  52980
ttgtttgtta atttatccaa tcatccattc actcagcaaa catttatcaa tcatttgcta  53040
tgtatatgcc agacactaca ccagattttg caagcacaga gatacaaaat cccttgcttg  53100
caggaaaacc tttggtttca ataaatgata ggagaggggt tgcaggggta ctatctatga  53160
aagttcaaag gaagcatcta acttagggtg gtaggggatg gggctgagca gaaggatcag  53220
gaaggtgttg gatggcagga ggcttttagc tgagccttga aaaggcaagg ggaggttggc  53280
cgctttgatg gggtgggcta aggactatcc atgcagaaga aagagcaggt attaaaggtg  53340
tcaaggcagg gagttacctc ctttgggaac tacacataaa gaagaatggc tagggcctgg  53400
tgtatgggat tggggtggga aacccaaggc aggaagaaga cagatcccaa gaggtctggt  53460
gtgcatgctg aggggatcag gtgccatctc aatgccatgg ggagtcattg aaggaaaagc  53520
agttagagcc atgggatcca gttcacatat gatcaatcac ccaaacaaag gaaagtttac  53580
tcaacaacat gttttcattt ggacttcatt ttgtcaaagc atgaaagtga tgtcagaaat  53640
agaaatgagt gtattcatgg cacaccacca cacccagcta atttttgtac tttttgcaga  53700
gaactcctga cctcaaatga tccacctgcc tcggcctccc aaagtgctgg gattacaggc  53760
gtgagccact gtgtctggcc taaaacacat tttctaagat ttctttactt ctgggccacc  53820
tccacaaaat tttatggttc tgggaacccc tatctgaaaa agcacaggta tcagcaataa  53880
gtataatgaa cactcactag agggaaagtc attttggttt gggttggtta tggaagcagt  53940
gtcatatgaa aagggctgga ctgtactgca gaaatagaag acccacaaat tgctatggct  54000
tataacagaa aaataaagat ttagatgtca ctcatatgtc cattattgaa cagttgtgac  54060
tctgctccct gtcaccttcc ctccaggacc gaagctgaca gagcaccctc tatccaatca  54120
ttgcctgtct tatgtcagag ggaaaggaga tggcaaatca tgcatcagcc cttaaagctc  54180
tgcccagaag tggtacatta ccatttctgc ccacatttca ctggccagag caggtcacat  54240
gatatgcctg agttcattag ggcaccagat gttgggcaac caataataca acccaccact  54300
gaggtcttta ctaagaagat gacctgggcc ttagggaatg gccatgattt acctggtaga  54360
cacagcaggg gagcaaaagg aaaatatgac aatattttta tgaaatcaag acttggccac  54420
atgaaacttt tttttttttt tttttttttg agactgagtc tcgctctgtc acccaggctg  54480
gagtgcagcg gtgcgatctc ggcttactgc aacctccact tcccaggttc aagtgattct  54540
catgcctcag cctcccaagt agctgggatt acacgcacca ccatgcccag ctaatttttg  54600
tatttttagt ggtgacagtt tcactgtgtt agccaggctg gtctcaaact cctgaccaca  54660
agtgatctgc cctcctcagt cttccaaagt gctgggatta caggcatgag ccaccacacc  54720
tggccgtgac acccttagaa aactaacttc aaggcagaat gcttcacagt gacaaatctt  54780
aggatgccac tttatagaaa tattctgaag agagaaaaac ccaggtgagt cagagcagcc  54840
tggggaaact tcttagaacc aggattttgt ggaattcaga ggattttaaa aggcagaaaa  54900
tccaatgaag ccattttaag ctaaaacaat gtaaataagg tggggctgtg cctagggtac  54960
tagggtgcag aaaggaacct gcctcctgtg ggcgcatttg tgttagcagg tagtgggaaa  55020
ttcgggtgga gggcaggtga tggaggaccc tgaacaccga gggaagactc tggatgttat  55080
```

-continued

```
gtgccaatat ttatcaagaa aacgcagtcc tggagataca ccaataattt ttgaaatgtt  55140

acagtagata ctaattgaaa cctacagtgc gccaggcacc gttaggttag cagtgaacaa  55200

aaccagcaac ctaaacaaaa tggtgaacac accaggcagt gcccttgtgg gttacatttt  55260

ggtgagacag atagtatata gataaacaaa tatacaatct caaagagtga aaaagttgtg  55320

aagaaagatg acacaggatt agagagtgac tagggtgtat atggtggcag tggtggtggt  55380

ggtgcagcca aggggtgggg tggaggacaa gacagctgtg aagactggtg agcatgaggt  55440

agtccctggt aacaaccagc gctccacacc ctaccctcag agtgccattg cagggttagc  55500

atactccact gagtaaagct tccttgtcca ggcaatcagt tagaagagcc aggaatgctg  55560

ggcccaaaga ggttggccag agagaaaagt gcaggggaca tggttcccag atccacgcag  55620

aacccctggg gaccactgag ttccacaacc tcaacaaggc ccagggttat actaacacag  55680

caggtggcct cattttagac cccacaccag aatctgtgca acgggaaatt ccagtgcagc  55740

agaagttgga gtcaaatgcc tgcctatttc tcattccatt ttgggaagcc taaacaggga  55800

agccttctgt gttcctctca ttcccatatt aaactgaact gcaaaactca tggctctaag  55860

tagactttag aattgaccta ggcagaagaa atagcccagc cccttcatta cttcagagca  55920

gaatagagca cttactctta tcacagcagc acaagacccc tgggacacct gactccctga  55980

gacccttcct tgacaggttc ccctgtccat aaacaaagtc aggaattccc agcccactac  56040

acagaatatg acagttaagc ttcattggga tcctgtggct gacctggggc aggctagagg  56100

gcatcacatc tgtacaggct ctcagctttg cgagttcaga aacagactgg gtgttcatgt  56160

ggactggccc aaacctgaaa ctctacagaa atcgcagtgc atgccaggtg gtttgccatg  56220

aaaaaaggtg tgtgtcccag agacagggtg tgtatggtac aaatggattt tgtccacgtc  56280

tttccttccc ttgccagtcc agccacccta ctgtcttttt tttttttgt cagtttttgt  56340

tttttttaa tttaagttct gggatacgtg tgcagagcat gcaggttcgt tacataggta  56400

tacatgtgcc atggtggttt gctgcacctt atcaacctgt catctaggtt ttaagccctg  56460

catgcattag gtatttgtcc taatgctctc cctccccttg cccccaaccc tccaacaggc  56520

ccaggtgtgt gatgttcccc tccctgtgtc catgtgttct cattgttgaa ctcccactta  56580

tgagtgagaa cgtgcttacc ctactttctt ttcggtttgt ttttttgttt gttttgagac  56640

gagttttgct tttgttgccc aggctgaagt gcaatggtgc aacctccgcc tcctgggttc  56700

aagggattct tcagcctcag cctcccgaat agctgggatt acaggcatgt accaccacgc  56760

ccagctaatt ttgtattttt agtagagaca gggtttcgcg atgttaggca ggctggtctc  56820

aaactcccaa cctcaggtga tccgcctgcc ttggcctccc aaagtgctgg gattacaggt  56880

gtgagccacc acgcccggcc tacctaccct actttcttag cctatttgct gactagcatt  56940

caaactgagt gcagggagaa cacctagcag cctgatccca gaagtgcagc tactccacat  57000

tccacagctc tggggcagag tgactaaggc tcacctgtag tccttaaatg gagagcaatt  57060

tgggatgtac cagctaatca aataaaacca aggcagcaaa caatagccat cacttctcaa  57120

accatcctca ttgtgcccct cgactccctc cttccatttc cagttctccc cagaggggag  57180

acagacaata acctcaacaa cagaagccag tacacagcaa gcttgcttca cacgttcacg  57240

tttcttttgt ttttctttga tgttttttct ttgatgtttt ccattttcca tctctgaggt  57300

gattagcagt acagcatagt ggttaagaac agagcaggga ctccacggat agactaccca  57360

gtcttgtcct ttgttacagt ggttcttaag ctttcaggtg actgggaatc acctggagag  57420
```

-continued

```
cttattaaaa cgtagatttc cagccgcgtg aagtggctca cgcctgtaat cccagcactt  57480
tgggaggcca aggtgggcag atcacttgag gtcaggagtt cgagaccagc ctggccaaca  57540
tggctaaacc ccatctctac taaaaataca aacatgagtt ggccgtggtg gcacacatct  57600
gtagtcccag ctactctgga gactgagaca tgagagtcgt ttgaacccag gaagtggagg  57660
ctgcagtgag ccgcgattac tctaatgcac tccagcctgg gggacaaaac aacaaagcga  57720
gactctgcct caaaaaaaaa cccaaaaaaa caaaacaaca cagattactg ctccccaacc  57780
ccagagtttc tcattcagca catccaggat ggaacacaag gatgtgcagt tctaactagt  57840
tcccaggtga tactgatact cttggtacca tgaccacact ttgagaacct ctgccttatg  57900
aagtttccaa agactgttga cttgtgtgtg aaaggataac cctataccta ccacttgtgg  57960
ctattagggt taaatgagtg aatatacgta aaatgctttg agctgtgaat aataaaatgc  58020
aagcatagct agtctggaaa cttcgcccat gccttttgtc tctgttttgt ttgttaacct  58080
ccatttgttt tgtttgtaat aaaccactta gccaggtacc tcttcctctc cttcaaatac  58140
agagggcgtg tgaactttgg agaatgagtg tttaaactga cctaaataat atgtgatttt  58200
caactcttct gtggattcac tcattattca atgtgggctt tgcgtgccat atgtgataaa  58260
cttcttgtgt gtggggtata gtgggaatgt gcatacgtga aattgatgtc agatctttgg  58320
atcgttgtta gggaagataa aaggaactca cactacagtg cagccttgcc agtagggctg  58380
ttattcccac ttacgtggaa gaaactgaaa ctcagttcat tgaggaaact ctctcaagct  58440
tggacttagg tcagaggtga cttgtaagga tacacacaga gaaacatcca agcctgggaa  58500
accagctgat ctattactct gtgtaccaga actttatgta tcagaccaaa cacacaacaa  58560
gcctcacgaa aaactggaat gtgcttcaca tcactgcagc tttgtcccaa tgactgggcc  58620
acccaaggtc tctgcttctc cctaggcatg tcccattgag actctccaca tagagatagt  58680
ctgatggagt tgtgacatta acacccaatg tggaatgtcc cggtggggtg gcctcggatt  58740
cagttgtctt gttctgtaat cagtcatagc caggaagaaa gcccagtctt gctccaggag  58800
caaaccgtag cagcatgctg ctgaaagaac tgcctgggga ctttttcccc agagtggggt  58860
tggctttggc ctgtctagta ctttcaggga cattgaggca gccttagatc ctcagaagag  58920
cacagatctt tggaatcaga cagacttgga tttgaaccct gtttctgcca cttaagtttc  58980
ctcaactatg cattgtggct atcacacacc tcacaggtgt gaagatcaaa taacataaag  59040
tgcttagcag agtgcctggc acatagtatc tgcacttaat gaatgatagg gtttggtttt  59100
ttttttttta aattaaaaaa actggaaaga tggaaaggtg aaaataatta ctcagcttta  59160
tcatcctatc atttagcctc ttatccctga cagtgtgcca ttttcaatcc tgtagggatg  59220
cattcattat tattaatttt ttaagagaca ggtcttgctg tgtcccaggc tggagtgcag  59280
tggcacaatc ataattcact gtaacctcaa actcctggga tcaagggatc cttgcacctc  59340
agtctcctga gtgtaaggtt cttgtattgg ttggaaccct gagagcgcgc caacagaaaa  59400
cacgaggcgg tgtgaagcaa catgctgttt taatgagcac ctgggtacag gcaggctgaa  59460
gcctaaaatg gcatcagccc caagtgagga cagggcagag gttttatagt ctcttgtaaa  59520
caggaagtgt cctagtctga cgtaactgct atgttgtacc caggtggcct gtttctcgat  59580
caggggtaca tgtcttcgtc cagggtaggt gtcttcctgc cggctctctt cctgcttctg  59640
ctatcttgct gacacacgct gctgacacaa gtggacttgc gccttgggac tgggcctgag  59700
aagggaggag ttattcatct ccttaagctt tcaggccccg gggagaatct tataccgcgt  59760
agctaggatt acagacacat gccaccacac ccagctaatt tttaaagttt ttgtagagat  59820
```

-continued

```
ggcatcacac tgtgttgccc aagctggtct caaactcctg gcctcaagta atcctcccac  59880
ctcagcctcc caaagtgctg ggattacagg catgagccac cacacctggc ctcatccatt  59940
atttaattta aggctttata tgctacgaag ctataggttt ttaatagaaa gtctgtttta  60000
catggttgta attatataat tttgcattct ttttccatac tataaaatat tttaatgtta  60060
taaattctgt acgtaatttt agtgaacatg ctataattta cataaaattc cttatcattg  60120
gacacctaac aatagagaat tgattgaata aatggtagtg cattcatata ataaaatatt  60180
aatcagccat ttaaaaaggt ggattagaag tatacttctt aacatataaa catgttcacg  60240
attatgtata aaatgaaatg agtgtaccta aatatcaact acctctcaag tctgtctgga  60300
cattttccta cctcagtctc agcaactttc aaactttaat gagcctccca atcaccaaag  60360
gaacttgtta aatgccagtt tcacgcttta ccccaagagt ttgactgaga ctggggctca  60420
ggaattggca cttttacaag gatcccaggt gcctctgatg tgggaaagac acctcaccta  60480
tttctgcctg ttgaagctat acttaatttt ccaagcttct ccttcttctt tctcctgaag  60540
tcctgtagta ttttgtagca cttgtctgct ttcttgtctt agagatctta gcaaatgctt  60600
ctaaattgta aaacttttcc tgatcctcca accaaaccta gttatgcacc catgtcacag  60660
ccccagaatt tgtgttaaac cctgtgtgag ttgctgaata taaatactga aatctctgga  60720
atccaaactt catttacttt gtggtggaga gagagtggct gagtacttca gaactcttta  60780
gaacacctgt tatagcagga acttttggga ataaaggtgg tctttctaac cttgatttaa  60840
aacaaaaaca aaaacaaaac cttgtttaga ttacttttac ttacctgaca gtcaggttgt  60900
gaaaagtaaa tagtttgtcc tttgtgcatt tgctctggtc taggccagag atagccagta  60960
agctggagag ggcagttaaa acccttcaag aggcctgtca ttccaaagaa tagttttctt  61020
caggtctgtt ggttggtttt cattctcaga ctgtgtcact gaggttgttc aaggtaagat  61080
tcttatcttg cagttcactt agggaccact tatgctaaaa ttgagactga gttactcatc  61140
aaagtacttc ttcacttaga tttttatcag tgtgatttcc ctccttcttt aaataatatt  61200
ggatatccat atcaagtcag gtttatgtca tcttacatta tcttttatgt aataggccag  61260
cttgcagatg catagttata aataactatt gataaatatt atattgagat gacactgaaa  61320
ttttgtcctt gcttgtaaga gaactagatc atattctgta taattagtta acacaaaaga  61380
attcctcaga aacaaacttt aaaagccagg tataacagct cactcatgaa aagttccttg  61440
tttcatatga aaatggtaac tttgtagaag taaagctcca gacaacaaag aattgacagg  61500
gttggggaat ggaaggttaa tgaaattggt taatcaaatg cttctgatgg ggaatcacca  61560
catgtagtgt acttgtccac atggcaaact cggaatcact cttcagaacc ttgtgtagag  61620
gcatcatcta taaaaccctg catctgtaag gctttttcat cagcccccctc cttggaaaaa  61680
atttcttttt ttattctatg cccacaacag tacactacac acacatctat catatgtcac  61740
actctagtat atgcttgtgt gttactatta tccaatagat cagaaattca ttgggcatag  61800
agcatgtggc ttatttgtgc aatctgaccc aggttcagtg cctggatata gtagtattca  61860
ttaaatagat gtatgaataa gaattctgca ctgaacaggg tacataaatc atataaactg  61920
cattttgtgg gtgttttctg agaactcctg cagttaaatt taaagcatca ccttatgaca  61980
aatttccata aaatattgtt ataataaatt atgaataaat gttgaaaata acaagcccag  62040
tatctgctgt tccctgagtc cctgatggca actgcatgct ccccagtctg tgggactcct  62100
gatttaaaga gctagatctg aacttctgca gaaacctgct caacatttgc ccattggttg  62160
```

-continued

```
ctgtgaaatt cctctcctgg gctcttaaat tccacagagg cttaattatt acagatattt  62220
aaactttgta catacatgac ggatatcaaa catacccaca tctctaaggt aaactgtatt  62280
aaaagtgcca gacaatttta aaattgaaag ggacttcgtc atttttactg gttaggaaac  62340
caagcctctt aagagacaag cagtttttgt tagtgggagg agcactagaa ttgaagtcaa  62400
atagaccaga gttcagttct tggctcaggg gctcaaatca cagcctctga tcggcagtgt  62460
gatcataagc cctttactta atatttttga agatcagttt tttcatttgt aaagtttggt  62520
taataatccg tctcagtggg tcacaacaag ggattacttg agattacctg agccagagca  62580
gcacacataa tatctgcaca aagcaaatcc tcagtgagct tttgtctctg ccctttcttg  62640
cccagatcac acagagctaa gacttagacg ctttctttgg gttgtggttc ccagttcacc  62700
tgacaggact cacacatatc aaggatgctc ccaaggggct gtgtcacatc agcatttaaa  62760
tacagaattc aggatctcct gctttaaaaa caatctccct tctgagttac tctttttaaa  62820
ttttatttat ttatttattt atttttgaga cggagtctcg ctctgtcgcc agggctggaa  62880
tgcagtggcg cgatcttggc tcactgcaag ctccgcctcc ggggttcaca ccattctcct  62940
gcctcagcct cccgagtagc tgggactaca ggcgcccgcc accacgcccg gctaattttt  63000
tgtatattta gtagagacgg gatttcactg tgttagccag gatggtctcg atctcctgac  63060
ctcgtgatct gcccgcctcg gcctcctaga gtgctgggat tacaggcgtg agccaccgtg  63120
cctggccctg agttactttt attgctgttg tttttttttc tttccttgta ctgcgagtta  63180
tgacaccctc ccagtcaacc atcaactata atttaacttt atataattgt gtgaattagc  63240
aagatcctag gaggctccag gatctcaaag gctccaggat ctcagggtaa tgtatataca  63300
cattttagaa gagtaagatc tacatcgcct aataagtctt cagcttttaa aaatcacatt  63360
ctaaaataat aagtgaaata tttgtgctga attgaaaggg tttccataaa ttctgacggt  63420
aaacgatgag tgttttaagc atggagatgt tagtcataca aacttaagtc accatgaaac  63480
aggcgatcaa gtgggggaag cagcatcctg tttcctagtc ttaccagagt tcatttgtca  63540
ttttaagaga caacttactt ttccatcttt tcttcttttc ctgtaaaggt agaaacctgt  63600
gggttcttgt tgtggggcgg tttccaaagg aacacagaat tgggattcca gagttcaaat  63660
acgtggcaaa tatgcatgga gatgaggtac gtatgtggct tgaatttctg aaatgtcacc  63720
agagaagctt cccctagggt ctcttgagct ctgtataaat gctaccgagg aagcctggag  63780
aagtctccag catgcattgt acaaagaagc aaggcccaga gaggtcttcc tgtgaggcct  63840
gtgggaggtt aaggaatcag ggtccaacaa ccaccacagc tgtatggttg tgtacccagc  63900
accctgtcag agtagctgga gcttgttttg tgtttggggc cggaagaaca acagttcccc  63960
agccctgaac ttctgccagc caatccctgc atctcctttc tgggttaagt tttcccacct  64020
cctggtcagc atgaaggtga cccagcaaag gagctgtatt gtatccgaac ccacaaccat  64080
cagaaactcc caaatagcta cccaaattcc tgagatctgg cttttcaaat gcttttgtta  64140
ctctctctta aatctaacac tcattgtctt cagtgctcca gtttagacaa tcacacttat  64200
gattctctcc tactcaccat tcaacaaaca cttggctggg tgcagtggct cacacctata  64260
atcccagcaa tttgggaggc caaggcaggt agatcacttg aggtcagtag ttcaagacca  64320
gcctggccaa catggtgaaa ccttgtctct actaaaaatg caaaaaatta gccaggtgtg  64380
gtggcgcata cctgtaatct cagctagtcg ggaggctgag gcaggagaat tgcttgaacc  64440
caggaggtgg aggctgcagt gagccaagat cgtgccactg ctctccagcc taggcgacac  64500
agtgagactc catctaaaaa aacaaaacaa aacacaattt taaattcctt aataatatct  64560
```

-continued

```
tgcctctttt ccaacttagc agggataaac tctcctttta tttttaggtt ctacaaaata  64620
ccatttacca ctgttaccta cccagccatt cttgccaggc agttgaagat gttcacctct  64680
gtttctcacc ttgcttcctc agaatatttt gagaccatga caactgaaat attttctgtt  64740
taccaggact ctataaaact gagcgatcaa agagtcccca gccatcccag taaggaaact  64800
ttgcacagga atgtgggtat taccctgtaa aacacaactt ataactttag ggactttctc  64860
atttacatac atattccaat aagtactacc tgctgacttg ttaaaacact tctggatttg  64920
caatagtatg ggtggcatgc tctaatcagt gctgagcttc ctgttctggc ttaagccctc  64980
cccaaactct ataggaactg gatctaccct tcatggtaca ctccgcctgc ccttgccagg  65040
catgctgccc aacctgtcct gctgagagag gatacttctt gcagctgcag ctaagatgca  65100
agcacctgcc cctagcaaag gaataagttt ttgaacccga ttttggggtg ggtgcaagtt  65160
tagcccatct gtgacttttt gagcatcacg ggcggcttct ttaaaaaaga ctacgttgca  65220
aggagtctga ccaaagttag ttttaataaa acaactgttc gttatagaca gcagctcaga  65280
ctgcgtttcc cttttgctat cttgtctatt gatcgaggtc ccttgatcaa ggtccctcag  65340
aatgcttttt tttttttttt tttttttccg atggaatttc gctcttgtct cccaggctgg  65400
agtgcaatgg catgatctcg gctcactgca acctccgcct acaaggttca agcaattctc  65460
ctgcctccgc ctcctgagta gttgggacta caggcatgca ccactatgcc cagctaattt  65520
ttttttgtat tttttttttt ttttagtaga gatgggggtt tcaccatttt ggccaagctg  65580
gtctcgaacc cctgacctca ggtgatccgc ccgcctcagc ctcccaaagt gctgggatta  65640
caggtgtgag ccaccgcgcc tgactcagaa tgcatttgta acaagagaca tatggcattc  65700
attgtcttta gtagtttttt tattgctggc atttcagagg ttccagctat ctactcagaa  65760
attagtcctc agaactgaaa ctcccaaaga taagcaagag tcctttccgt cccctacccc  65820
cgaatttgtt tattctttcc atgcactttc ctaaatttct ggcatcttgt tgtctggtgt  65880
atcgttcaaa tcagggctcg ctagtgcgct ctgattcttt gagaaatgct gagggctgag  65940
actaggcagc ggggaaaagt cccagtgtat tttggggtgg gaatctgaag cacttttacc  66000
cccttatgtg acccagctcg tggcaatgtc tgggggctct atggggctag taagaaattt  66060
attattctga atttgagacc ttatctattc tgtcctcccc atgccgctag gagctgaaga  66120
aagtgatggc ttaacattgg agcagagaag tccttctgaa tacaggatat aacaaccccc  66180
tttttcctcc catagatctt ttgaaattga aagcattttt aagaagcaac agagctaaca  66240
ttttagggca gtgattctta accttttttg gtgtattcct tgctattctg ttataaattt  66300
gacctgactt cagggtctgt ggattaccta ggagtttatg gaccttaggt ggagaatccc  66360
agcagggaac acatacacac tgagtggcag ggtggacaga attggccaca ctatttttaa  66420
aatgggaccc cacccccact gtgcgtgtgt gtgtgtttgt gtgtgtgttt ccacacttaa  66480
tactatggct agatgacagg aagcatcagc tgcatcaggg agactcagct ctgctgatta  66540
cacctgccat tttcccccat gtatttttat tttacttatt tatgccttgt tttagaattg  66600
ggtctttttt taaattagaa attgtctggt ggccaaaaag catatgaaaa agtgtctaac  66660
aacactaatg atcagagaaa tgcaaatcaa aaaccacaat gagatatcat ctcataccag  66720
tcagaatggc tattaataaa aagtcaaaaa ataacagatg ctgatgaggc tgcagagaaa  66780
aaggatcact tacacactgc tggtgagaat gtaaattagt tcatccactg tggaaagcag  66840
tgtggtgatt tctcaaagaa cttgaaacag aactacgatt caacccagca atcccaatat  66900
```

-continued

```
atacccaaag gaatataaat tggtctgcca taaagacaca ttcacacgta tgttcattgc  66960
agcgctattc acaatagcaa agacataggg ttagtctaga tgcccaccaa tggtagactg  67020
ggtaaagaaa acatggtaca tatacatcgt ggaatactat gcagccatga aaaaagaaca  67080
agatcatgca cttgcttata gaacaagatc tataagcaaa ctaaacagaa aatcaaaaac  67140
cacatgttct cacttataag tgggaactaa acattggata cacatgggca caaagaaggg  67200
aacaatagct accagcatct acttgaggat ggagggtggg aggatggtga ggataaaaac  67260
ctacctgtta gatactatgc ttattaactg ggtgatgaaa taatccatac accaaatccc  67320
cacaacacac aatttaccta tagaaccaat ctgcacttgt acccctgcac ttgtaacatt  67380
tacctataga accaatctgc acttgtaaca tttattttta aaataaatgt taaaaaaaaa  67440
aaaaaaaaaa aaagcaggcc gggcgtggtg gctcacgcct gtaatcccag catttgggga  67500
ggctgaggtg ggtggatcac ctgagtttag gagttcaaga ccagcctggc caacatggtg  67560
aaaccccatc tctactaaaa atacaaaaaa ttagctgggt gcagttgtgg gtgcctgtaa  67620
tcccagctac ttggtaggct aaggcaggag aatcacttga acccagaagg cagaggttgc  67680
agtgagccaa gatcatgcca ctgcactcca gcctgggcga cagagtgaga ctgtctcaaa  67740
aaaaaaaaaa gaaaaaaaaa ttattacaaa atcaacatat gttcatgtta gaaaaagtat  67800
aaacaaaaca ttatatactg accttcccaa aattagtgct cttaatttct tatttgtttt  67860
tccagatatt tgtgtgtgca tgtactttta ccaaaagaga tatgctattt gcaacacttt  67920
taagtaaata ctagctacct ttttgtacca ataaatcttt atcctatctt tatcttatcc  67980
cccactttct agtttctcca attgtcctca aatgtctcta aaattaccca aatcaggatc  68040
cagtcctggc tcatgcatcg catttagtgg atatgttgga tctcttggat ctcatttaat  68100
ccagtatctt tttattatga tactaggctt gataaagagc ccaatcagtt gtctgccctg  68160
tagaatgcca catattctgg atttttggtt tgcttcttta tagtatcact gcagttgtac  68220
ctctagtccc tgactttact tcaaactgga aattaaatct aaaggtttgt tgaatttaat  68280
gtggctaata cacatcttag gagttgtgac gataggttca tttgattgat gctgagggtt  68340
caggctaatt cacctggcta cactcaggaa tgccaaaagc aaactccggg tagcaaaatc  68400
aacttaaaat ggcccatttt cagccaagta ttgttacaaa ataagtaaag ttaaactcac  68460
tcctcatttt gcatgaattt cacgtattct cttattcttg caaaggtcat tgttctacta  68520
ggatcatggc tcatactgta gatatttttc ttgtcttcag tgaccttcca ttgtctcaca  68580
tgctttctat ggcacaggct cactatgcca cattaatcag gctggcaagt tgcctcctca  68640
aacagtgctt tacaagaaaa taataacaat agctaacatt tatggagcac agatgacaat  68700
aagtgcattt taggcctcgt ttctttggat cacctctgca gaaggcatgt ttattagtcc  68760
catgtaccat gaagggggcc caggtttatg cttggtcacc agctgtggga acccggagcc  68820
tgaacaccaa gctttgccca gctgtggatc cactccttta ctctctcttc tctgttttta  68880
aaatgttctg ttttatggtt ttcattctta agtatagatc tatgatctat ctcaaattaa  68940
tttcactggg atggatacta agttgttgca gcaccatttg gtgagaggat ttgggcttgc  69000
tgttatgtaa aagagtaaca agctcttgga gggcaacact ggaataagta tcttccagtc  69060
acctacctgt ccctttcttt cccctactct tcacttctct ctccttgact gctggggagc  69120
tgacagacat agcactcgtg gtgagccttt gtcaccgatg tttattcatt ttttggagca  69180
gcatgggaga aacatttctg ggttctttc tcattttaat aagactagta ggtgtttttc  69240
tggttcatcc aggcacacac attatttgca cacatattgg catgttggat tgaagcctca  69300
```

-continued

```
attctaggtt taatttacgc aagctcctaa ttggcatcac ttggcatacc tacagttgaa  69360
tcttttttt ttaattggaa gggttgatgc cagtgcaggc tgaatggggt tctctgccat  69420
tcctgtatgc tacagatatt cagattgcct gggaacagga tccttgtccc ctcaccttcc  69480
cccatcacct cattctgctc ctggcttggt gtgtagtaaa ctataaccaa tactctaaaa  69540
tcagagctat actgaaaact gggaccatgc cctgaaacca ggagcatcta acatcctcag  69600
cctaaatgtg gatgcagaag agaagcctgg gaaaatcttc cccagccctc cctactcttt  69660
gttttgtgct tatcttctat cccatgtttt tcaaattttg cagaaaaaat acttttcttg  69720
ggtaatctct aggttggtaa gacatcttta attcctgcct aatggaaata ttgaagcaag  69780
gcatgactgt gtgcttaaag aattgggtgc ccaggccagg catggtggct catacttata  69840
atcccatcac tttgggaggt caagctgggg agattgcttg aggccaggag ttcaagacta  69900
gcctgagaaa catagtaaga ccttgtctct aaaaaaaaat ttaaaaatta gctaggtggg  69960
gtggtgcata cctgtggtcc cagctactca ggaggctgag gtggaaggat tgcttgagcc  70020
tgggaggtcg aggctgcagt gagccatgat cacaccactg tacttcagcc tgggtgacaa  70080
agcaagaccc tgtcttaaaa aaagaattga atgcctagag ttttaagcca accctagtaa  70140
cattaagcaa agtatcatag gtcagagcct gggttcaaac ccaggtttcc ttgacctcag  70200
tgccaagggt cttaaatact gtactgtagg agtaactatt gaatatgctt gtaaaataat  70260
ttaactaaat tgcaattatt ttttatttta gagttgggat ctcgctctgt aacgcaggct  70320
agaatgcatt ggtgtgatca tggctcactg taacctcaaa cacctgggtc caagcaatcc  70380
tcctgcctca gcctcccaca tagctaggtc tagaggtgtg tgccaccaca ccaggctaag  70440
tttttatttt tttgtagaga tggggtccca cagtgttgct cagactgttc tcaaactcct  70500
ggcctcaagc gatcctctgg ctttggcctt ccaaagtgtt gggattacag gcttgagcca  70560
ttgcgcccag cctaaattgc aattctgctt ttttggggag atggggggta ggaatttttt  70620
taagccttag tttcttaaag agcaatgaag tatttttact aagatagact taatatgggc  70680
ttttgtaact gcccaacagg ttcattttgc ctgttgtcca gatagagcag atttatcaag  70740
acaggggaat tgcgatagag aaagagttta attcatgcaa agccaactaa acaggagacc  70800
ggagttttac tattactcaa gtcagtctcc ccaaaaattc agagactggg agtttttaag  70860
gataattttg tgggttgggg gagagacagt ggggagtggt gattggtcag gtcggagacg  70920
aaatcatagg gtgtcaaagc tgtcctcttg tgctgagtca gttcctgggt gggggccaca  70980
agaccagatg agccagttta tcgatgtggg tggtgccagc agatccatcc agtgcagggt  71040
ctaaaaaata tcttaggttt tacaatagtg atattatccc tctgagcaat tggggaggct  71100
tggaatcttg tggcctctgg ctgcataact cctaagccat aatttctaat cttgtggcta  71160
atttgttagt cctacattca ggaaaaggct attatcatct ttgtttcaaa gttaaactat  71220
gaactatgtt agtttagcct atgcccagga atgaacaagg acagcttgaa ggttagacgc  71280
aagatggagt tggtttcatc agatctcttt cattgccata attttctcac tgttatgatt  71340
tttgcaaagg cagtttcact tttgaaaaat tcgcatcaca tttagaattt tatgattgtg  71400
gcattggttt atagtttatt gtattccaga aatataggtt gaaaagagaa aacattccct  71460
gggtaatagt ggccatattt gtcaacctga aaataaagag ataaaggata aatgactttc  71520
acacaccttc taagtataag agacagttga tgagatgtag tttgcatgtc taaatgtttt  71580
acttaggggg tattttaatg gtttacgcag acagtgggac acaatatctg aaattatggc  71640
```

-continued

```
cgttctggaa aatctgggaa gtacagtcaa catgcagtag aggttcccaa cttatcatta  71700
aaccaaaaca caacattaaa gcttgtcttt ctaaatgccg ctgcccaagc tccttttcct  71760
accactatcc tcaggtgata gtaaaatgtc ctcagtaacg ctctgtggtt tgaataatta  71820
aattctttct ttttagattt aggcagagct cattgttttc caggtgaaat atctaattca  71880
ttttaagcat gttttaaatt aatgaactgt ttggtgacca gatatcccaa gtccctgtca  71940
tgagcgtaat tgttagcctg tgcctctata aaatgtgttc ggtatttaaa aatccttcag  72000
ataaaatagc ttgatcattt gtacatctcc ccttacaaag caccttaagt cctcatgtga  72060
atttcagaaa gttcttcctc aggatagtct tgatcttata atgaattttc aacagtagtt  72120
tattagcaat tatttattga atacatgata taccaggagc tggacaagct acaccaagaa  72180
cacagggata cagagaaaaa ccgtgaaggt ccctgacttc ggggcttcga tggtggagtt  72240
agagaaaggg aggtcagtca aggtcagcca agtgattgta acgtgtgtga cccgcattag  72300
ataacacagg tgtcatggtg aacccagact tgggaggtca agaaaagtat gctagataaa  72360
tgtcatgttt aggctgatat ttgaagaaga aggattagct aggcaggtca gacaaataac  72420
ttaaatctat aacacacaca ccactgtgga gccccacagc ccgatgactt tccccccaga  72480
agctgcatca cagggtagca tttcaaaaac agattccatt gttaggatag ctgaagattc  72540
tctctctctc tctctctcac acacacacac acacacacac acacgcatgc gcgtgcacac  72600
acacacacac cacacaacac tgcctgggtt gtagattgtt ccttcaaaaa tttttttctg  72660
ttttttttaa taaacattct gtgaagaacc agaacactca tttgtatctg tgtggcaaat  72720
tccaacttga ctgaattgaa ctgcagctga tagagaatgt attttctgct ttctgggtga  72780
ctgccatttt aaccaccgga tgaaggagat ggagtgagag tctccggagg ccggtgtgtc  72840
catcaggccc ccgtttcttc atgagggctt ctccctgaag tctgtgctct cacaggaagg  72900
aagccagcat gctgggtgaa aggctgcctg ggcaattgga gactcttttg accacattct  72960
tttttaaaat ttggactctc cagggtttcc tgtcaaagac ttaattttca atgaagggag  73020
gtttatacat aaaacatgaa tgagtgtttg aaacatttat attaaggttg ggaagaatta  73080
atttgaataa tatttggcat aaatctgctg ttacagaggc aggaaaagat ggcccaaaaa  73140
gaaaggagga ttttgtttaa ctgcctctga aatttcatct gtttatctca gcatttaaaa  73200
aattatctga tgcttagttg gttctttatc ttattttcaa gatttttatt tacccttgca  73260
attgagaact tgtgatttgt tgtggactat tgagacacac aaaaaatact ttggttacat  73320
acttgtttcc ctgaaagaat catgatttta ttatttttgt aaaaatgaca taggttttct  73380
ttaaaaagaa taagaggaaa taaaaatcat tcagaatact gtacccagaa atagccatca  73440
ttaatatttg tcagacatca ttgtagacat ctatatattt ctgtagtaag agaatgagag  73500
gaattaaaag aatataaaat aaaatgtctc atatgttata ttgtatgaaa ttttatttta  73560
tttgaattaa cagaagaata aaactgaagt gaaactaaaa taactggtga aattgatgct  73620
ttctcaaaat aagaaattga ttatcacatt tgtctttctt tttttttttt ttttgagaca  73680
gagtctcgct gttgcccagg ctagagtgca gtggtataat ctcggctcac tgcaacctcc  73740
aactcccagg ttcaagcgat tctcctgcct cagcctcccg agtagctggg attacaggca  73800
cctgccacta cacctggcta atttttatgt ttttagtaga gacagggttt caccatgctg  73860
gccaggctcg tctcgaactc cctacctcag gcgatctgcc tgcctcagcc ttccaaagtg  73920
ctgggattat aggaatgagc caccgcgccc agcttgatga tcagattttt ctaaagttaa  73980
gaaaaaagat tattaaaaac tttgaaattg tagtcatttt atgtgtatat attttaactt  74040
```

-continued

```
ttgatagtat tttatgtccc cttactatga aatgtgaagt aattaacact ttgaaaattt  74100
ctccctcaac ttcttttttt tttgaggtgg agtcctgctc tgttgcctag gctggatgga  74160
gtgcaatggc acaatctcgg ctcactgcaa cctctgcttc ccaggttcaa gcgattctcc  74220
tgcctcagcc tcccgagtag ctgggactac aggtgcccac caccatgccc ggctaatttt  74280
tgtattttta gtagagacga ggttttacca tgttgcccag gctggtctcc aactcctgac  74340
ctcaggtgat ctgcccacct cagcctccca aagtgcttgg attacaggca tgagccaccg  74400
tgcccggcct caacttttat attttgttct atacccatac taccaagact gcttaatcta  74460
attctgtatc taacagaata ccaactcaac ctagcctcct aatcatggtt tctttactct  74520
tccttttcac tttctttcgg ttgggtgaat ttcattgcca actcgtgtcg tgattgtttg  74580
catgctggag agtgtatgat tcagatagct aagagacaaa ttcacattta gagtcacatg  74640
gggattctga tatcacttcc tctctgttct tgacttggga ctcagatagg ccagggattt  74700
ttgccgattg aaccatacta tggcctctaa ccagcattta gacatttaag gaactatggg  74760
actcctggtc acttcctcct caccttcctg tacctattcc tccccaaacc cttctgagaa  74820
agcttcttaa accaacgatc tttttcacat ttttttggtt ttttttcgag atggtgtgtc  74880
tcactctgtc acccaagctg gtggcgcgat ctcggctcat tgcaacctcc gcctcctagg  74940
ttcaagcgat tcttgtgcct gagcctcctg agtagtgggg attacagtca cctgccacca  75000
tgcccagcta atttttgtat ttttagtaga gatggggttt caccatgttg gccaggctgg  75060
tctcaaactc ctgacttcgg gtgatccacc cacctcggcc tcccaaagtg ctgggattac  75120
aggcttaagc ctccacgccc agccccttt cacatttaaa gttactgtca cagttttatg  75180
ttaccagctc ctccccactg gctttagggg aggtcataag tagctcatca aggttacttc  75240
caaaggtgct ggaccttcaa aaacctatta tatcttaaaa ttggaaccca gtggggtgta  75300
caagtgactt ttttggttat tagcttgtaa ggactttttc cagtgacaat tttgactata  75360
aaaacaaaaa tctggccggg cgcggtggct cacacagtaa tcccggcact ttgggaggct  75420
gaggcaggca gatcacctga ggtcaggagt tcgagaccag cctggccaac atggtgaaac  75480
cctgtctcta ctaaaaatat caaaattagc cagacatgct ggtgggcacc tgtaatctca  75540
gctacttggg agggtgaggc aggagaattg cttgaatcca ggagacggag gttgtagtga  75600
gccaacatgg tgccactgca ctctagccct gggtgacaga gtgagactct gtctcaaaaa  75660
aaaggtagtg gaagaggaag ataaaaaatg agtaggaaaa aaagttgaag tcaggattgg  75720
acataatctg actctaaatt ttatggttgc ctatgaatct ataattcata tatcccaaat  75780
tttctttctt tctttttttt tttttttttt gagacagggt ctcactctgt cacccatgct  75840
ggaatgcagt ggtgcgatct cttctcactg ctgcctcaac ctcctgggca gcacaagcga  75900
tcctcctacc tcagcctcct gagtagttgg ggccataggt ctgtgtcacc atgcctggct  75960
aatttcttat tttatgtagt gatgggatct cgctatattg cccaggctgg tctcaaactc  76020
ctgggctccg ccttagcctc ccaaagtgct gagattacag gcatgagcca ctgccaccag  76080
ccccaaattt tcttagtccc aatttcaatt attctgtgtt cattaggata acaaatgttt  76140
aaaatgtggt ctctttatgt gccagtgagg gaatcaagtg agaagtggtc atccaaggac  76200
cgcttatcct ttgtcacaat gttgaagtcc tacagtgaaa tcatgactgg aaattcttct  76260
gaggctccat gaaatctttt cttgcacagt gtctacatga atgtgcctgc agcactctcc  76320
tgattttctc acctgctgcc cctgagttct catttactaa cccctcaaca acatctgttc  76380
```

-continued

```
ttctgaagca gattccttga acctaaaatg atagggagaa tttgatgtag tctaagcaga  76440
tcttcctatg ataaggctga catttaaatt acttttttta aataagaaaa ataatgactc  76500
tctctcctgg ggagggatta taaagcaagt tctctcacag gccttcagtt tcccaagcct  76560
tattgatact gcaagctaat ttaggtggat atgacagctt ttaacatttt aatagtcatg  76620
cttttactta atatatatta gaaatatata tctagaaaag tgataatgat atgaagtttc  76680
tcaggagttg gaagccagcc ttagcaacat agcaagaccc tgtcttaaaa aaaaaaaaat  76740
ctacaatgtg atgattttaa gtctgttatc caccaataca tacatgataa gcttcatatg  76800
caccatgcat tctcatggaa atacgtgatt cctgtgcttc tctgtaactc aacctcttgc  76860
tctcccactc cagaagatac tttggaaggc aaccaaatga aaaatgttgt aagaatcatt  76920
attgcggccg ggcgcagtgt ctcatgcctg taatcccagc actttgggtg tctgaggcag  76980
gtggatcact tgaggttagg agttcaagac cagcctggcc aacatagtga aaccccatct  77040
ctactaaaaa tacaagaatt agctgggcgt ggtggcacac gcctgtaatc ccagctactc  77100
aggaagctga ggcaagagaa tcgcttgaac ccaggaggcg gaggttgcaa tgagccaaga  77160
tcgcgccaat gcactccagc ctgggtgacg gagttgagac tgtctcaaaa aaaaaaaaaa  77220
aaaaaggaag cagcagcagc agcagcatta ttccactcta attcattttt gcaatatgta  77280
aactatttac aaataggtac tttcactctt actagcattt ttcagcatac ctcaggactg  77340
atcgccacct gatggccact tggcagagca taagcatgct tgagaaagag tgatcttaca  77400
aactagtttg ggtctgagat atcatgtgta gagaccccta ttggggaatt tgtaccgtag  77460
ggagtgcttt ccttattgcc tctgacctaa taatgtcctc ttttctcttt aacacatata  77520
gactgttggg cgggagctgc tgctccatct gattgactat ctcgtaacca gtgatggcaa  77580
agaccctgaa atcacaaatc tgatcaatag tacccggata cacatcatgc cttccatgaa  77640
cccagatgga tttgaagccg tcaaaaagcc tgactgttat tacagcatcg gaaggtaaag  77700
aggggctggt ctatctttac ttgaaaacaa cacaacacaa aggctcccga caggcacctg  77760
ttggccttgg caagaggaga tgtgtcatgg tgagagccct cagagccggt gtcatgtcgc  77820
tgatgtgcca aagctcaagg cacatcaggg ctgcctccgg cttgcaggaa gaaatgcaaa  77880
taaggctact ttgccccggt gcccacctag cctctccatc ttcatttgcc actccttctc  77940
tctcccctgc ctcctcccct ctaggcctcc ttcctggaag taccaggtgc tttcttacct  78000
cagcatttta cacacaccgt ttccctgcct aaatagcatt tcctccaaga ctctttctct  78060
cgacctgtca tacactagat cccctgataa actctcacat cacctggcac tttactgtca  78120
gagcacaact tttaatatct aatttcttgc ttcatgtctc tccccccact acactgcaag  78180
ctacctgcag gcaggaatcc tgtccattgt gtttgtcgtt gttagatccg cagtgcctgg  78240
cagagcaccc aggcccttgg taatgaccgg ttgatttatt aggccagtag tccaagaact  78300
aaccataagc aagaacgggt cttgaaggag ctctgattta aacagtttat tttgtttcaa  78360
gctgccttgg gaggtttgga atttctcaga tgtctaatat acattcatat gtatgcaatt  78420
tacatatatg tgtttgcttt accaaagctg aacaaaatct caccacttga ttccctccaa  78480
ttttaagttt ttcaaatata tttaaacatg gctgttccac gtttcacaag tacttctgtg  78540
taatgtgttt agtgttgttt ctgttatcag ttgctactta acgaaccacc ccaaaattag  78600
cgacttaaag caacagcctt tttatttact gttgattcca taggtcagga atttgggcag  78660
ggcagagcag ggatggctac tgtccgtgcc acaggtctgg ggctcagctc tggtctttct  78720
gagacaattt acctggagcc atggactctc cgtggactct ccacgtggcg accattggga  78780
```

```
tctcaaggtc ccaaaaggga gcatctaaga gcagaagtcc caaatacaaa cacttatcaa  78840
acctctgcct gcatcacaat agctagtatc tcattggtga gagcagatca cgaggcaggg  78900
gatgccatgg gatgtaagtg ccaggtgtgg gtcatggcag gccacaaggg cagccatcca  78960
ccacacccat actcacgttt ggaaagacac ctggagccta aaccaaaggg caagacactg  79020
taagaatcca ctccctcatg ccctatcaat aagccctaaa atattctttc ttttaaaggg  79080
aaaattataa ccagtatgac ttgaatcgaa atttccccga tgcttttgaa tataataatg  79140
tctcaaggca gcctgaaact gtggcagtca tgaagtggct gaaaacagag acgtttgtcc  79200
tctctgcaaa cctccatggt ggtgccctcg tggccagtta cccatttgat aatggtgttc  79260
aaggtaagca ggtgcgggtc cagttctggc ttcttaagtc cagagtgggg ctgaaaactc  79320
tctgcctctg gatggggatc agctctccct tcccctctta acttctctgg cagggtgaaa  79380
agagcttcat gttcccaact ctagccatcc ttcctgtgat tcttcaacag cagatgggca  79440
gtgtggctga actgacaacc cacagctgga catgcatcag tgaattagtg aaatttagat  79500
tctagaaaat acaatctaaa tagtcagatt ttgattctct gacaagagac aacatggcta  79560
aaataacata aaactggaac aactcacttt tttttttgct aatcatatat gaacaataat  79620
tgttgactct tcttaaaact ctgtgggatg aggacccaaa atattacagt agctttattc  79680
acccctataa tacctaaaga aattgtcctt acctccagaa attagcaaga gtgactgaga  79740
ggacacttaa tttttaagct gatttaggag tttggatttg tatctgactt atttgggggc  79800
tatcaccttg catatgttta ttataaagta gaaagaagaa tagaggaggt ggatgaagga  79860
tttctctcta gggaaattag agcatgtgtg tgtgatgcga ttatgtcttt gctaatatgg  79920
tgtttgtgtt tcctcttact ctcaagtcag tttaaaggtc ttggttcatc ttttaaatgc  79980
agcaactggg gcattatact cccgaagctt aacgcctgat gatgatgttt ttcaatatct  80040
tgcacatacc tatgcttcaa gaaatcccaa catgaagaaa ggagacgagt gtaaaaacaa  80100
aatgaacttt cctaatggtg ttacaaatgg atactcttgg tatccactcc aaggtgagtt  80160
tctcttcatt tcttccattc tccttattgc cttcacccag aagtgccagc tggtttattt  80220
tgatccagca gttgttaaaa gaactttagg cacaataggc ccttcactct gtccttatca  80280
gctaatatca taagagcagt ggagatgact gattgtttga gagatgctca gacatgttcc  80340
tcattaccaa gggccttctt cattcattca ggtacttatt ctgtgtctgc ctactgtgag  80400
ccaggaactg aaagatgaac aagacacaca cctcaccctg gagttgaata ggggagacag  80460
acacgcagat aagtaattgt gatagcagtg caattagaat aaaaacagat ttagagaagg  80520
tgcagtgtac cccaagggtg cacagagcca aaatacaata gggagtagtg aagagcttgg  80580
agaaatgtga tgcttacatc ccatctaaca gggacagctg ctactagatc tagctaatta  80640
ttgtcatgca gccttgggga gccaatactg ccagatcttg cagtttgtaa agagaagctg  80700
aatttgtaca tgaagtatca tgattttaaa gccattttgc gggctcaaca aaagagctct  80760
tcagacagga tacagtggga ggagggcccc cagttctcca atcttggaat aagacagccg  80820
ggtaagggac aggatgagat tgtcatgtag gcaacatgga aggagagata ttcttattag  80880
agggaataat ataaacagaa acccggggta ggagggacct agggtggaag gacaggagga  80940
gagacggact ggaactggat ttccatgcct caggggaaaa cattcccttt tagactcgtt  81000
agcctgaccc caccaacagc aagttgcggc atgcatttct gcgtgcaggc cacttccaaa  81060
ggtgccttcc ctaattgtca ctttggatgc acaggctttc aggtaatctt tcacaagctg  81120
```

-continued

```
gtatttttat gcctgggtgg ctctctgtca gttttcctgg taatataaat aagcatagac  81180
cacaactgat aggcaacagg tccaggcagc attccaaacc tctctctggt gtccaagata  81240
cagccccctc tcctacctta gggcttctgc atcgtccctg ctctccacaa tttgtagcta  81300
agaaagggcc catcctgtcc agtggcagag ctgtccttca tgttcactgt ctaactttcg  81360
aaggcaaatc cagatgtgta ggaaattagc tagaaacggt tgctgctggg aattgttccc  81420
cagtgtgcct gtgtgtgagc tgtgtatcct tctcagacaa aaaacaggtg aagccagctg  81480
ccttgaggag cccagaagaa tgtgcctggc ctggcctgga tgttttgttg gccaggcctg  81540
acccgcctta tccagaactg ccccctccac gcttggcatt ctcagttctg gctatctgct  81600
agggatccat aatgcctgcc tgttttgcta tttaaaacaa accctttgaa agtaagggac  81660
cagaggagag aactggaaag tcagcatgag cagtggcagc ctgggctcca caggggggccg  81720
ggccgttcac ctctgagagg cagtgcagca ctctttcttt gatccccagg agcactctgg  81780
catattgggg aagcccacag gtgctggcgg aaggtggcct gcactccagt gtctgtcatt  81840
tactggccaa aacccctgag cacttttctt taacatctgt gatcatgttt cctcatctgt  81900
aaagtagggg caattgctgt gaggattaaa tgagctgata caaagcactt catatggtac  81960
ctggcaatag tgaatgttgg cccatgattc ccccaaatta gcatgcttag ctttgcttag  82020
taagtgtatt tataaatgat ttgtagaaat attttaaagg aatcttattc tagcttatat  82080
ccatgtaaaa tgtaatttaa gaaagaaatg aaattcaaag aatcattttt gtaatgtagg  82140
atttcaaaaa ataaaaacaa aaaaggaccc ttccttcacc cgtcacttaa ttttgatgca  82200
cagttgaact tcagtcagct ctgatccagt tacccatatg ggaatattta ggattgtcta  82260
gtcacgcctg ggtaatagaa tgtcaagccc tgattttaca agctaatatg tcaaattcat  82320
tttttcctgt ttacatgtag ctgtctgatt catttgtccc cgaggcacgt gatacttggc  82380
tccactccaa ttttagaccc taacaaaaat taaatatgct tgtgtttagg tggaatgcaa  82440
gattacaact acatctgggc ccagtgtttt gaaattacgt tggagctgtc atgctgtaaa  82500
tatcctcgtg aggagaagct tccatccttt tggaataata acaaagcctc attaattgaa  82560
tatataaagc aggtgcacct aggtttgtaa aattttctta ttaattccct attaatacaa  82620
aatagagcat ctggcaagac ctctgggttg actaaacgca agcctttatt tatgctttgt  82680
agttatagcc tcatttcagt gccagatctg atggttaaga attctctctg catgagtatc  82740
tgcagtgtgt gagaaatgca gtgcccactc attcatagaa aaggaagcat gatgcatgtt  82800
cctttaatat gagggtataa aaatccagag taccaggtgg tcgtggtggc tcatgcctgt  82860
aatcccagca ctttgggagg ccgaggcagg tgtatcacct gaggtcagga gttcgagacc  82920
agcctggcca acaaggcgaa acctcatctc tactgaaaat acaaaaatta gccaggcgtg  82980
gtggcacacg cctgtagtcc cagttacttg ggaggctgag gcaggagaat cacttgaacc  83040
cgggaggcag aagttgctcc ctccgccaag gagccaagat ggtgccaatg tactccagac  83100
tgggtgacag agtaagactc catctcaaaa acaaacaaac aaacaaacaa acatccagag  83160
tccccctaat tttacatgtt gaatgatcta gaaatctggc aaaatatcag gaaaataggc  83220
tgctactctg ttacatcatc tcccatttag aaaaatacta tgtttgcttg tcactcacca  83280
cgcagtacca aggaccctga gaacactgga cataccactt tgcatttttt ccagaattgg  83340
ggtggtgagc tagcaccatt accttcaacc cctctcacct ccgaactctg ccagatgtcc  83400
tggtgctaga aatcttgcca gcctgtttgc tgaaggctgg ctggccctta tcacagatag  83460
acagactaaa tgtggcagag agtgatagct ttcaaacgtg cagtggactc accgggagcg  83520
```

-continued

```
cttgctaaaa cagattgcca ggccccaacc cggagtttct gtttggacca ccttaccacg  83580
tgatgctgat gctgctggtc cagcggctat acttagaaag ccattgcact agagaaacac  83640
actgctagag atgatgatgg aatcttgtac agttcaagtt tattaaccag gtggtgtctc  83700
tttgggcaag gtgtggaagg ctcttctata tttacagagg tgaagttatc tttctccatt  83760
cagaatggct tggggagaga aacatatcag gaattggcat aatagctatg ataccacatg  83820
gagagagaga gagagagagt gtgagtgtgt gtgtgtgtgg gtgtgtgtgg gtgttgaaaa  83880
ggtttgctgc atgggcctac tgcataactg cataattccc ggaattttct gcatgattca  83940
cagcaaagct ttcctcctgc tacaaagaag atggagaagg atgagggaag gtagcacagg  84000
gccagagggc tgagtgcaag gatgattagg acccttcctc ggcacacatc cctaaaaggg  84060
atgcccctgc cctctttcat acctgtatcc ccagcctcca tgccctgacc tgaagagaag  84120
tacacaaaga ttactggtaa actcacaggg ctatgtctaa ctggctgagt cgttcatgga  84180
ctaggttgac tccctgtgat aggggatgtt atgaaatatc gttctttctc accagcatct  84240
taataaagat tataaactta ttattgggac tttcaccttc ttcattatgt catcaaacgt  84300
tgtcttgggt tctctcttgc ttagtattct ggtaattctt tctccactag attttcctca  84360
tgaggcatgt catgtattag tctaacattt ctattatatt tctacctcta ttgatccttt  84420
agtttgttaa tctattacta ttattatcat tatcatcatt ttagagacag ggtctcactc  84480
tgtcacccag gctggagtac agtggcacag tcattgccca ctgtaccttg aactcctggg  84540
ctcaagtgat ccttctgcct cagtgtccca agtaagtagg actacaggtg cacagcacca  84600
catccagcta attttttaaa caattttata tagagacaga atcttgctat gttgtccagg  84660
tgagtcccaa actcctgggc tcaagcgatc cttctgcctc agcctcccaa agtgctggga  84720
tcccaggtgt gagccaccgt gactggctct gcctatcctt ttctgaaatt cattcttcac  84780
cagtatcaac atgggtatgg gcgtgcaagt gaacatcaaa tatgctctgt gtaactgcac  84840
tactattttc agaacctcaa tctagctgta aagattattt accaagcact gaattaaggt  84900
gggctttgaa gtatcatgtt gatgtaatat tgccagggaa agggcaatat aaattgcagt  84960
atacctatta ttatttttaa taatttggaa ggcttaccag tccatttgca ctaggttttg  85020
tttttttgtt tttgagacgg agtctcgctc tgtcatctag gctggagtgc aatggtgtga  85080
tgatctcggc tcactgtaac ctccgcctcc caggttcatg tgattctccc actcagcctc  85140
ccaatttgct ggaattacag acacccacca tcatgcccgg ctaattttgt atttttgtag  85200
agacagggtt tcaccatatt gcccaggctg gtcttgaact cctgacctca ggtgatccgc  85260
cggcctcggc ctcccagagt gctgggatta caggcatgag ccaccatgcc cagcccattt  85320
gcattaggtt ttataaagaa tgtgtatctg cctgtctcta taatcagatg caaacaactc  85380
actcaaaaaa tacatatatt ggcacatcaa ccctgccccc ttgtggttta agacagatgc  85440
ataacatggt ttaataatga aaccatattt caaaatacca atacagtgtg gttattacta  85500
cttaatagaa aggttctctc cctactagtg cccaataaga aactaatgaa tattttgttt  85560
gtgaagaatg gcagcaaaca cccctttatt ggtattgctc tggtttaaag acattattga  85620
tattcgtcaa actgcattgc atttactggt tccattttac caattgctag gatgcttctg  85680
agtttctgag gttttgaccc atctggaagt ctctgagcca ccttgtctgg gaaggaaagg  85740
ccttctgctt tagtggaagg gccttgccaa gagggtagag gcttaggtag agcccaagct  85800
gttttgtcat ctggcgatgt ttgcaatctt gagcaagcac ttgtctgaat ctcagtgtag  85860
```

-continued

```
tcaacagaaa gttgagagta atagcatcag ccttgcctcc caccagcctg ttctaaggct  85920
tcagtggtgt tattccttca attagaactc actgcagacc tcaactgaaa ctcgggcccc  85980
ttggtgctgt gttgtcctgc ttagaggatg atttactagg ttcaagttga gatgagggtg  86040
tcggcagaca ttaaaaccaa agtagcaaag gagggcaagt ctgaattcta gaggcttaaa  86100
atgtcttgct tgtcccggtc tctgaggaga agcaaagatg agccagacac ggtgttacct  86160
gcctgctgcg gccctgtctt tcccctggac tcctcaaagc agatctgaac ctagagagca  86220
agggaatggc tcacagcatc cagaaaccta agcaacctgg gcataaaaga atctggtatg  86280
tgctgagttc cagaagcctg tgagccacag atgtggatct gttatcacat ccaaaatagg  86340
aggcaactgt gaccatgcgg tggggacatg ggcacaaaca agcagtctcc taagtactgt  86400
cccagctccg actctaaatt gtggccaaca gatgcagaat tctagtgctt gcccagccaa  86460
gacttttcat tcatgaagct ctaatccatt tccaagggaa aaagagcttt acatttctcc  86520
catgtatctc cccatctggc cacagaattt atatctcaga ttttatgtct tctcatttgt  86580
attgtatctg agcatttttc aaatttttcct tttttttttt ttaatatagt gttggctctc  86640
tctgcgtctc ttagggtcta ccagtctttt tttcaatgtt tcaacttcag catatagaaa  86700
taaatcacat tttctggtaa aacaattact tccctcttaa gtaaaaggtt tggtggtatg  86760
tagacaaaat attgtaaaga catatacaag ctaaagcacg cttttatttg gctggtggga  86820
ggggtttcc tttgaatata aattccatac ataagcatgg tctgtgtttg cccagtaaca  86880
gtgatattcg catacccccag gcttccatag ctggaagaac catctttagg tttaggtaag  86940
agtcatatga aagtgagtct ttgggcctgt aatcccagca ctttgggagg ccaaggtggg  87000
cggatcactt gagatcagga gttcgagacc agcctggcca acgtggtgaa acccatctct  87060
actaaaaata caaaaaattag ccaggtgtgg tggtgggcac ctgtaatccc agctacttgg  87120
ggtgctgagg caggagaatc gcttgaaccc gggagatgaa agttgcagtg agccgaactg  87180
gtgccactgc actccagcct gggcaacaga gggagacttc aatttaaaaa aaaagaaagt  87240
gaatctttgg gttattaggg gatgacgaat gagggtcaaa ctggaatatg aagattttca  87300
gacatttctt caaatgcaaa ttgttcttcc tttttctatc tttgagggta ggcagaccgc  87360
aggttgactg gagccttgat tcagctgcag cacacactga tacgtaggtg ttgttcaagt  87420
ccctgaggcc atccaaaatc actgtcatgt gactgtcaaa aaagtcaaat ctgttctatt  87480
aaagtgtaac tgcttctagc caagaagaaa tttgctgcct ttttttaaag ggtaccatga  87540
cttttttttt tttttttttt tttttttggt gtcttctgcc aactactcat tactagtacc  87600
ctgaattcta tttcatcatt atctccaatg ttaaagaatg gtgtaatgtt agccgggcgc  87660
gatggctcac gcctgtaatc ccagcacttt gggaggctga ggcgggcgga tcatttgagg  87720
tcaggagttc aagaccagcc tgaccaacat ggagaaaccc tgtctctact aaaaatacaa  87780
aataagatgg gcgtgatggt gcgtgcctgt aatcccagct acttaggagg ctgaggcagg  87840
agattgcttg aacccgggag gcagaggttg cagtgagctg agatcgcgcc attgcagcct  87900
gggcaacaac agcaaaattc catctcaaaa aaaaaaacaa aaaattgtgt aatgtcagtt  87960
tcaatgatag ctctgcttca ttttttatgc acttgatttt cttcgatttg gttggttttg  88020
gggaagtcaa caaaaaatac aaaagatgcc aacagacaca acaccatcca gcacaagtta  88080
ccttgctgaa acgcatggat tttctaagtg gcatgaagac tgtaaactag ctcagagccc  88140
tggaaaagga aataatatgc atagcttctt ccctcacata ttcctgcttt gtggaacaaa  88200
gttgaattaa gactccagaa attcatctaa tatattctcc ccccgccaca ccacatagtt  88260
```

-continued

```
tttcttaatc caaataagag gaaaggaaag aaagccaggc ctggtggctc acacctataa  88320
tccctgcact ccagcacttt gggaggccaa ggtagatcat gtgagctcag gagttcaaga  88380
ctagcctgtg caacatggcg aaaccccacc tctacaaaaa aatacaaaaa ttagccaggt  88440
gtggtggtgt gtgcctgtag tcccacctac ttgggaggct gaggtgggag gactgcttga  88500
gcatgggaag tcaaggctgc agtaagccct gatcacacca ctgcactcca gcctgggtga  88560
cagagcaaga ccctgtctaa aaaaaaaaaa agaagaagaa aggaaagcaa gaattaatgt  88620
ttgttgatcc tcctgttctg tgttacttac atttaatctt cacaaccatc ctgggtggtg  88680
gtatattatc cccatttcat aggtgataaa attgaggctt gggaatgttc agtgacttga  88740
gaactagaat tcaaatcaaa acctgactag gttctttctg tcacaccaag ctatgatgat  88800
gggtacacgc tatatttatc acatatcaaa ggacctccta aggggggcac agtgtaaata  88860
gctcttcaaa ataatgccat tgaagctgag tgtggtgcct cacacctgta atcccagcac  88920
tttgggaagc ttaggcaggt ggattgcttg agcccaggag ttcaagacaa gcctgggcaa  88980
catggtgaaa ccccatctct acaaaaagtt aattaattaa ttaaataaaa caaaataatg  89040
ccactgaaac ccaaggaata aatgcgtaat caggttacca aattattacc aatttatgat  89100
tgggtactac ctaaacatca aaaggatatg tatcaagcag taggaataaa tataaatgga  89160
actgtgttta aaaaagagag ggcaaagagg aacacacgaa gtgaaaatag aagtttacac  89220
agttgtatag agaaagggag aaggaaatgt ggcattttcc tcctcaggag acaaaaaatg  89280
aagagtcagg aactaaatag gacagaaagt ataataaaag gcaacctagg tcagatagaa  89340
gtttgttgaa gttcaagata aacattgttt tgctaaatgc caaaattttt atttttcact  89400
ttaaccgttt ctggggaaa ctgttacgtg tgcctcgtat tttctgccc taataaataa  89460
ttattgagca taactgtttg gggagagttc aagatcatct tactattgta gctcttcatt  89520
ctcatttatg ttattgggga cttaggcagc ttcaccttaa ggtaatatga tttgacgctg  89580
gagtaaacaa actagatgtg acacgtagga tctaaaataa gaaaggtctt aaaatataaa  89640
tggcttttta aaaattgtac tcctgaaatt ttgagagggg ctgtcgagac tatcatgggt  89700
tgacggctag gctgggccac ttcgttggct gtgtgagttt gaggaggtta ttttaataag  89760
ccagagcctt agttttttc atctgtaaaa tcatgataat aattgatgac acagagctga  89820
tatgagaatt taatgagaaa atgctcattt ggtagttagt acagagcctg gaatatacta  89880
agtgctcaat aaatattggc tgctgttact ggccaatcga ttccatgctt ccaagaagcc  89940
ttgtgattat aattttgctt cccatgtagt tgcactacaa gacaaaacta ttgagtccct  90000
cgcacacgta aatattttgt tgtaactaat acattgacac cgtttttatt taggatttta  90060
tggaatccac caatggttgt agtacagttt ggtgactgag taaataactt ggaagtgaca  90120
ggaatggatc ttaggttgtc atctgtgttc tctcactgtg ataatacgta ctaatataaa  90180
tgggctattc aacaacgaac aaatttaagc tataaatcag attagtaatt ttgactgtat  90240
tttaagttac atcaaaaata agttttttcc ctctctaaca cttaatatta actcacaaca  90300
ttgagttagc taataaatat tgcatatatt gttcttaaat atttataata atttttatat  90360
gccataaaat atggtattaa tatttaattt tatttttgtc ttgcaggtgt aaagggtcaa  90420
gtttttgatc agaatggaaa tccattaccc aatgtaattg tggaagtcca agacagaaaa  90480
catatctgcc cctatagaac caacaaatat ggagagtatt atctccttct cttgcctggg  90540
tcttatataa taaatgtaag tatgcaatgc tagttattgt tattaaaata ttatagaact  90600
```

-continued

```
cataatactt attcacccag aaggaatcca aaataagtct aggaagttca aaagtagatc  90660
catcgagaca gaaagaaagg atagtgtcag acttgcaatt ggcaggaggt ggaagaggtg  90720
gaaattatat gaaaaaaaaa aaaaccacaa aaattcatat tttttccctg atggcaattt  90780
ttaaaaaatg gaagccaaat cctatctctt gtgatatctt ttatgattaa aatgtaaccc  90840
gattaataat aaagaataag caatgtagca aaggtagttt atagtttccc aggatacgac  90900
acaacaccca ttccacggca tacactttct actataaaaa atgaattgga taaagttcct  90960
tagaattcat tttataagtg aaatctgatc cacaaatttt aacactatat tcagcaaatg  91020
ataaacatat tttgcagccc ttttttcatc gatgcaagta aaatttcagt ctttaattcc  91080
ataaaatata tatttctgag tcattttatc cgaagacagg aaggcatgga ctaatttgag  91140
cctgagtgga tttatgtgaa agaactaaat gaataagtat tgatatagtt ggccagattt  91200
tgcctctttc tctttgatgt gaatttctct gagaaattca ggattcttct attttgctta  91260
gtggggctta tgccaaccat agcagtcatt ctatatagag ctaatcctgg gagaaggtag  91320
tcatctcttc tgtagtgaaa actgagttgg tattttatta tttcatcttg aggacatcat  91380
ggaaaaaaca tggtttttag tttataaaac tatagaattc agagcctcca tgctccatgg  91440
gttctcccca aggtgcctag atgtgaggct tatcaattgc taatcctttt aggaatttct  91500
actcctgccg agaaaatgga tagagcttga aaaatctcaa ctcactgtga atctttgtct  91560
aaaaaggccc tttattttcc tcctatttac tgtgatattt ctattctatt taaaaatatg  91620
attttccctg tagtgaatct aaacttatat gcaacctcat aaataagcca cacctttaga  91680
ataaagttat gaattgttca tttcccatta gttagactaa cacagtacac attgacccta  91740
gatattagtt ctaggataat atttgaaggt aagactctgg acattgaaat gaatgtgtaa  91800
aatacatacc aatgagtggt tatgtaaatg tcattcccca ttttttccct tctccaccat  91860
atataataaa agcatttctc agtagacatt gcctgtagtt agtttagcat ttgtcttgtc  91920
ctgatcattt cctccactaa aaaaaaaaag aaagcctaac caaagattca ggctgatatg  91980
aacaaaacca ggtaaaatca aagcttttaa aggagggtgg atgtggtggc tcatgactgt  92040
aatctcagca ctttgggagg ctgagaggca ggtggatcac ttgaggtcag gagttcaaga  92100
ccagcctggc caatgtggtg aaaccctgtc tctactaaaa atacaaaaaa ttacctgggc  92160
atggtggtat gcacctgtaa tcccagctac ttgggaggct gaggtaggag aatcgcttga  92220
acccgggagg cggaggttgc aatgagccaa gattgagcca ctgtactcca ggctgggtga  92280
cagagcaaga ctctatctca aaaaaaaaaa aagaaaaaag aaaagaaaga aagaaaagct  92340
tttaaaagaa gcaataggct tgtaggtcag ctgaaaagaa attagtaagt tgagaaaata  92400
attctacttg aaaataatct tgatatccaa ggaggatgtt aaatacacac ttgggacaaa  92460
gggaaagagt tatctcttta cccttctgcc ccacgaaaag gatggtggca gaaacatctg  92520
ctgcttcctt ctcttgactt acattgccag atgaggtacc catctgtcct tatttcattt  92580
tgtaattctt ggcaacagca ttcacaacgc tggtctctgt caacaggcat tggataactc  92640
agcctgcagg accaaatctg ttgctggccc agaggtctgg tagattgtta catgcattgc  92700
acaaaggctg cattttagtg atggatatca gtgttttcag tgtgggcacc acgaaccatc  92760
ttaagtcact catataattg tctcttgttt cttctcaggt tacagtccct ggacatgatc  92820
cacacatcac aaaggtgatt attccggaga aatcccagaa cttcagtgct cttaaaaagg  92880
atattctact tccattccaa gggcaattgg attctatccc agtatcaaat ccttcatgcc  92940
caatgattcc tctatacaga aatttgccag accactcagc tgcaacaaag cctagtttgt  93000
```

-continued

```
tcttattttt agtgagtctt ttgcacatat tcttcaaata aagtaaaatg tgaaactcaa  93060
cccacatcac cacctggaat cagggattgc tcactccagg ttactgcaac cctaactcac  93120
tctagtggga ccttgactgg agaaactcca cgatcttcct gaagaagaga aatggatgtt  93180
tccaaattcc acaataagca atatgtggtg ataatgaaaa gaatgattca gtcttgacgg  93240
tgaatggaag acacttacct aacaagtact gctcatttac actcaaatta atcttgaagt  93300
agtcttaaaa tgtgtaagaa gttaaaactt gagaagcaaa aaaatgcctg caaaaagaag  93360
atcattttgt atacagagaa ccggatgaat ataagcaatg aagatgaaca tttattgatc  93420
ttctacatac aagacttcac cataaggcca ggagcagtgg ctcacacctt gtaatcccag  93480
cactttggga ggccaaggtg ggcggatcac cctgaggtta ggagttcaaa accagcctga  93540
ccaacatggt gaaaccctgt ctctactaaa tattagcggg gtgtggtggc gggcacctgt  93600
aatcgcagcc tttcaggagg ctgagacagg agaatcgctt gaaccctaga ggcggagttt  93660
gcagtgagcc gagatagtgc cattgtactc cagcttgggc aacagagtaa gactctgtct  93720
caaaaaaaaa aaaacaaaaa caaacaaaca aaaaaaacac ctcaccatga gtgctacatg  93780
tgaatagata ttaagtgcca tatataatta gttctcagaa gaagggagaa atgatcatag  93840
gactgggaat tgttttgcaa acgttctagg agatgtgaga gaaaatatgt aaccacatct  93900
tagtggccca agaaaataca ggcctgaagg gataagattg tgtctctata gagcttcaaa  93960
gcatacaggt caattaagaa agcccctctc tctccagagc cgtttcccta gcttttggca  94020
cctggatgcc acagtcctcc attaggctga tgactccaaa gatgtaactc tagcctcttg  94080
cctgagcttc agactcgcgt cccactgccc acaggacaca tccacctgga tgtgactcac  94140
aggtacctcc aacccatcat gtggagatac tcatcctgtt cccccctagag ctgctcttcc  94200
tgctgcattc tctctctcaa ttactgggac caccaagcta ggaacctggg agtcatcctt  94260
gatactttct cttcctcctt aatcctgtgt attcagcaag taactaaagg ttggtgttgg  94320
ccaggcatgg tggctcatgc ctgtaatccc agcattttgg gaggccaagg cgggcggatc  94380
acttgaggtc aggagctcaa gaccagcctg gccaacatgg tgaaacccca tctctactaa  94440
aaaaaaaaaa aaaattagtc gggcgtggtg gtgcatgcct gtaatcccag ctactgggga  94500
ggctgaggca ggagaatcgc ttgaacctgg gaggcagagg ttgcagtgag ccgggattgc  94560
gccattgtac tccagcctgg gtgaagaagt gagactctgt cttaaaaaaa aaaattggtg  94620
ctgataaata ttgatgaatt ctgctctctg ctctctatgg ttgtcaacac tgcagagttg  94680
aggcctcata tctcacctgc actgctgcaa cagcttactg gtcccttgct cccagccttc  94740
tcctcttcag tccatcgtcc acacagcact ggggaagggg agccacttga aacaaaagtc  94800
aacaactggt tgtagttcat aaacacagag ctgtttgtgt cccctgtatc tggaatgcca  94860
ttatgaccca ctacattttt tctttcctac ccctcttaaa actcagttca ggtagcagct  94920
ccactaggaa gccttggctg accataatcc cattcaattc catttcacct cttcgcaggc  94980
agtctggggt tagggaccct ttctctttgc tccccaaaat aaactggtta tctctactat  95040
tggatttaca acattgtatt ataatcttct ccatgtgtgc cttctctagt agaatgtgag  95100
ctctttgagg ccaaggtcta tttaatttgt ttgaaaaatt cattgttata tcctcaaagc  95160
ctagcacata gtaggtactg aatgaatgaa tgaacaaggg gtgccaggag actgctactc  95220
ccagtccttc ccagaaactg cctagggctt tgagtcattt tatgaagcta ggtcttaatg  95280
cgtaggcaac ctcccagctc actatgaacg ctgacagaag agtgttttca tgtctataat  95340
```

-continued

```
caagaattcc agatacattc cttttactga accttgaatt gatcctaaga ttggtagtaa  95400
aggtattatg ttacctccta acagcactac aaagtacctt tttttatcag aaaaaaattt  95460
taccattagg actcaatttg aagtactaat gcttctcaag ttctccacta tgagagttac  95520
cctgtattag accgttacct ataagaatta aggggtaaag cactaaacag aaaagaaaaa  95580
aaaaatagca actctggtga gcagatttct ttcctttctt ccttccttct cctcttccta  95640
ccttcctccc tcctttccct ctcctcccct tctctccctt tccctcccct tcccttcctt  95700
ttcttctttc ctccgctccc ctccccttcc ctccccttcc catccttctt tctcttttt  95760
ttacttaatc cccagtgtga cagtaatata ggctgatttc tagaagtgtg gtgtattact  95820
catggaaagt gagttgcctt ggttattact ttcaattgaa agttctatgg gatctagaaa  95880
tgagacatac tggcatggag agtgagaacg acaaaggaat gaagagctac aggagcattt  95940
aggccatttc tatgccaagc ttattctaca tgcacaaaat catacatgtt aataaatata  96000
aacaaattgg aggcttattt aaaccaatta tgaaatctgg taatttgtgc agcagcaata  96060
gatgataacc aaaaaaaact cataataatc tgaatatctt gatcatttgt atttaaagaa  96120
gcagtaatta tatacttgaa agtacataat atagtattgc aaaaatgact ttggtatatt  96180
acaaattaaa agtatataag atgaaacttg atttgctatc aagccccaag caatttttca  96240
actgggcatt gaattctaac ttttctaaga tagcaatttt tgaagagaca cgaacaaaaa  96300
tctgaattag ttcatgagcc ttaatgtaaa tctcttgctg aaatagtttt taaaatcaga  96360
atttagttat ctatcagact caaaatcatt taaagactaa caaaacacaa tcatgatatt  96420
ctaactgtgg tcaaaccagg tacccaagcc acctccctgc ccaacgcctt tccggctttt  96480
cccctccctc ttgggctggt ggttatgctc ctccagctct agttcagcta taattccttt  96540
tatagagaaa ccaacctgat acacactttc atgatgggag aaaaatgtgg gagtgaaatg  96600
gtatttagaa agcagcagtc aggcacggtg gctcatgcct gtaatcccag cactttggga  96660
ggctgaggca ggcggatcac ttgaggtcag gagctcgaga ccagcctggc caacacggtg  96720
aaaccccatc tctactaaaa aaaaatacaa aaattagccg ggcgtggtgg caggcacctg  96780
taatcccagc tacttgggag gctgaggcag gagaaatcgc ctgaacccag aaggcagagg  96840
ttgcagtgag ccaagatcac atcactgcac tgcactccag ccggggtgac agagcgaacc  96900
tctgtctcaa aaaaaaaaaa agaaaaaaga aagaaagaaa aaaggcagaa gccctggatt  96960
caaatccgcc acacattcag tttctttatc tgtaaaatgg agaccacccc ccgccacgct  97020
gaacggtgat tctgtgactg gtaagagatg ctacattttt ggtgcttgtt caggtggagg  97080
aaagatgata gttaacactc aggtaataag tattttgaag gcagtataat ataccttctt  97140
aaagagtata cctactcaaa tgttggtaaa tgttgacatg attgaatcta aatggcaaag  97200
agtattttag aaaaacatta agtccctgca gataaatgac agtgttgatt tggatgctta  97260
attacattca gacatgaact gttggatgta tctgaaatgt taaaagcttt ttctcaacat  97320
ttccaaaagt ctttccaaga aatcaatgtt atgttttgtt ccagaagcaa atttgcattt  97380
gtgatctgtt tctaaaaatg gtacaagtta gctctgttta gaaagtaaaa atatctgatg  97440
ttagattgga agtatctctt cctggggaat ccagaaagat aagcatagca tattgtctta  97500
ctgcaataga taagttgctt attgagaagt ctggttgtta ttctatatgg taacaataca  97560
gttgatgtat attttatgat agatccttta tattttcctc atgactttag aagggggaag  97620
ggggagaaaa ttatgatgac cagactagtt aaagagcatt gaaagtccac agtactgtag  97680
ctaaagtaga agtttgggtt tgttatagac tttacattat atcaactaat aagcagatac  97740
```

-continued

```
tgtacagtat tgctcaccat tttatcatac ttttgcatat gaactactcc attgcctttt  97800

atagatgttt tatagctgat cttaccagtt ttcctggtaa cttttttat ttctttttt  97860

tttttgag acggagtctc gccctaacac ccaggttgga gtgcagtgcc gtgatctcgg  97920

ctcactgcaa cctctgcctc ccgggttcaa gcaattctcc tgtctcagcc tcccgagtac  97980

ctgggactac cggtgcctgt ctccacgccc ggctaatttt ttgtatttgt agtagagacg  98040

gggtttcacc gtgttagcca ggatggtctc gatctcctga cctcatgatc tgcctgcctc  98100

tgcctggacc tcccaaagtg ctgggattac aggcgtgagc cccgcgccc agccactttc  98160

tttaatacta taactaagaa tttattaaaa tgcacaaatt gtctaagact gtaaagttta  98220

ttggggagag gccatgacta cctctgaatt tagtaaattt aaaatatttc tgattctcaa  98280

taaagaacta atatccatat aaataatgct tttttcccat tatgttacct gaaaataagt  98340

acttatgcaa gtataacaaa gtccactaaa aataactgat taccaccaaa taaagcttgg  98400

gaaagaccaa acttaatgac cttttatgag gcaataacat tgcaacaact cttcaaagtc  98460

cagatagttc ttccagaaca agttacatat gctatatgtt atatatatta tatataatac  98520

attccaaatt aatttgtgtt gtggggcagt gtgttccatg gacaagatga tggatggaaa  98580

gtatgccttc tggtcagaaa aaatatttga aaattcacaa tttatattaa tgtaataaag  98640

aatctgagaa atgcagaaaa gaaatggatt tcccaaacat gctaagctat gggaccattt  98700

ccttaaataa tacagcctcg taccatccct ttggattaac atacctatat ttccaaacac  98760

attttgggaa atactgatat atagagaagg cttttgttct gaataacaaa ttttattgat  98820

ttccaggtgc ttttgaaata cagagaacag tggtaaacaa agaatttgcc tccagtagga  98880

actggaaaac taacagtcct aacccctgct aatatcgact tagtcatagg acagaggatg  98940

ggctcaagct tacatctgct ctttgaaaca cgctaaacaa ataatagttt aaatgagaca  99000

ttgctgagta ggaaatggct aaattacagg taccaatttt taaaaagtga cgtctcaatt  99060

tagaaaataa acaggaaata gtttctctgt tttcaagaga atttcattac atagaagcct  99120

cttaagcaga agttccctgg tatatttacc tagacttcaa cgtttaaatt tgcagctttt  99180

tttttttt ttgggacgaa gtctcgctct gtcacccagg ctggagtgca gtggtgggat  99240

ctcggctcac tgcaacctcc acctcccagg ttcaagtaat tctcatgcct cagcctctcg  99300

agcagctgga attaacaggc acatgccatg acgcctggct aatttttgta tttttagtta  99360

agacagggtt gcaccatgtt gcccaggttg gtcttgaatt cctggcctca agtgatccac  99420

ccacctcagc ctcccaaagt gctgggatta caggggtgag ccatcacccc ccagccaagg  99480

gttttttgtt tgctgtttga caactgagaa tagaactatt atttctctgc tctcttggag  99540

tggtctctca gcgctgttaa gagtctacca agcgtagtga ctcacatctg taatcccagc  99600

actttgggag gccgaggcga ctggatcacc tgaggtcagg agttcgagac tagcctggct  99660

aacatagcaa aaccccatct                                              99680
```

<210> SEQ ID NO 4
<211> LENGTH: 51039
<212> TYPE: DNA
<213> ORGANISM: Homo sapiens

<400> SEQUENCE: 4

```
tggtctctca gcgctgttaa gagtctacca agcgtagtga ctcacatctg taatcccagc     60

actttgggag gccgaggcga ctggatcacc tgaggtcagg agttcgagac tagcctggct    120
```

-continued

```
aacatagcaa aaccccatct ctactgaaaa tacaaaaatt tgccaggcat ggtggctcat    180
gtctgtaatc ccagcacttt gggaggccga ggcaggcaga tcacgaggtc aggagttcaa    240
ggctagcatg gtggctcatg tctgtaatcc cagcactttg ggaggccgag gcaggcagat    300
cacaaggtca ggagttcaag gctagcatgg tgaaaccccg tctctactaa aaatacaaaa    360
aattagccat gcatggtggc atgcgcctgt aattccaact actgggaggc tgaggcagga    420
gaatcatttg accttgggag gcagagtttg cagtgagctg agatagtgcc actgcactcc    480
aacctggagt gagagactgt ctcaaaacaa acaaacgaac aaacaacaac aacaacaaaa    540
aaaaaaacgg ccaggcgcag tggctcacac ctgtaatccc agcactttgg gaggccaaag    600
caggtgggtc acctgaggtc aggagttcga gaccagcctg gccaacatgg tgaaaccccg    660
tctctactga aaatacaaaa actagccagg tgtggtggtg gacccctgta atcctagcta    720
ctctagaggc tgaggcagga gaatcacttg aacctggggg gcagaggttg cagtgagccg    780
agatcgcgcc acttcagtct agtctgggcg acagtgaaac tccatctcaa aaaaaaaaaa    840
aaaagggtct accgttagtg gacaccttta gtcttccaac gagatacttc cacctcccac    900
cttgtggtta aaaaatgctt aactttgggc tgggtgcggt ggctcatgcc tgtaatccca    960
acactttggg aggcagaggc aggcggatca tgaggtcagg agttcgagac cagcctggcc   1020
aatatagtga aaccctgcct ctattaaaaa tacaaaaatt agctgggcat ggtggcaggc   1080
gcctgaattt ccagctactc gggaggctga ggcaggagaa ttgcttgaac ccaggaggca   1140
gaggttgcag tgagccgaga tcatgccact acactccagc ctgggtgaca gaacgagact   1200
tcgtcccccc caaaaaaaca aaaagcttaa ctttgaagag atttggtctt ctcagatgcc   1260
tcctataaaa agaaacaaat gtgagaaaag gtagaaaagg cctttttttgt agggagcaat   1320
tttttctaaa aaggcttttc agccaagacc ctctctctta caattctgac accatatcaa   1380
cttttaagac tactttttttc ttagaatgct tcttttttgc catttattgc acaaacaata   1440
atttgggggg ggactttaaa aaatcataat caggccaggc acagtggctc aatgcctgta   1500
atcccagcac tttgggaggc cgaggcaggt ggaccacatg aggtcaggaa ttcgagacca   1560
gcctggccaa catggcaaaa ccccatctcc actaaaaatg aaaaaattag ctgaaataac   1620
acagctactt gggaggctaa agcaggagaa tcacttgaac ccaggaggtg gaggctgcag   1680
tgagccaaga tcacgccatt gcactccacc ctgggcaaca gagcaagacg ccatctcaaa   1740
aaaacaaaca aaaaatcaca atcagtgaga ttaatgttta atgaacatac tgttattttt   1800
tattttttta agagacaagt ctccatctgt ctcctaagca gagtgtagtg gcgcaatcat   1860
agctcattgt aacattggac tcctgggctc aagtgatcct cccacctcag tctcccatgc   1920
atgccaccac aattttttgg atacagggtg tcattatgtt gcccaggctg atctcaaact   1980
cctggcctca agtgatcctc cttccttggc ctcccaaagt gttgagatta caggcgtgag   2040
tcacagagcc tggcccagga tgttatttta aaattgtctt tttgtcttct aaatcaacaa   2100
gaacttgata gttgctttca atgccaatca acatccttta ctactgtata cacaatgtat   2160
ttatttgaca tttgaaagga gatacggctg ggcgcggtgg ctcacgcctg taatcccagc   2220
actttgggag gccgaggcgg gcggatcaca aggtcaggag atcgagacca tcttggctaa   2280
cacggtgaaa ccccgtctct actaaaaata caaaaaatta gccaggcgcg gtggcgggcg   2340
cctgtagtcc cagctactcg ggaggctgag gcaggagaat ggcgtgaacc tgggaggcgg   2400
agcttgcagt gagccgagat tgcgccactg caatccggcc tgggctaaac agcgggactc   2460
cgtctcaaaa aaaaaaaaaa aaaaagaaag gagatacaaa aggatgttac aacctgctat   2520
```

-continued

```
ggcaagaaga tacaaaggaa catattggta tgaacagaat acctcagagt tgagtgtata   2580
aaaaaggctt aattcaccag atgcagtggc tcgcacctgt aatcccagca ttttgagagg   2640
tcaaggtcaa gacacgagga ttgcttgagc ccaggagttc aaggccagcc tgggcaacat   2700
agcaggactc tgcctctaaa aaaagtatat atatatatat aatgtacaca cacatacata   2760
cataaacaca tatgtattat atatatatat gtaatatatg tatattatat ataatatata   2820
tattagccag gcatggtggc aacaggcctg tgttcccagc tactcaggag gctgcagtga   2880
gtcatgtttg cgccactata ctccagcctg ggtgacagaa tgagaccctg tctcagcaaa   2940
aaacaaataa aaaacttcaa ggtggagtag gggttaattc aaggctacct aagctggatt   3000
tggggtgatt atggtcgagt ggatgcaaac agaatattaa acttccattc attaaaagtg   3060
cttactacct gccagacccc atactaggct ctatagattt attgtctcta aggtcactag   3120
gcgagtaagt accagatctg tgactttgaa cttcccacta caataagctt atgaactttg   3180
tttaagcaaa aaaggtttga aaagtgaaaa gcaagcaccc atttcatagt gttctaaaag   3240
tctaaaataa tccagtagaa catcagagat aaaatccaaa aagcaagttt ttcccccaat   3300
atttaaatca gggaagcaac atgatggtat ctgtaaacta taactgaacc aaaaatagga   3360
ccaaacgtag tgaaatccat ttagggagat attactgtga tcttgaagga aggcctactt   3420
aatacaggac agtgggctgg ggaggtgtga accaaaaata gacacaggca aaagcgctaa   3480
aatttaaccc tgagaaataa atgaaattca cctacaaaat aaatggaata aatttaaaag   3540
gtgaaatttt gggcttggcg tggtggctta cacctgtaat ctcagcactt tgggaagcca   3600
agacgggcag atcacttgac cccaggagtt tgagaccagc ctgggcaaca tggtgaaact   3660
gtctctacaa aaaatacaaa aattaggccg ggcacggtgg ctcacgcctg taatcccagt   3720
actttgggag gccgaggtgg gcggatcatg aggtcaggag ttcgagacca gcctggacaa   3780
catgctgaaa ccccatctct actaaaaata caaaaaaaat tagccaggtg tggttggcga   3840
gcacctataa ttccagctac tcaggaggct gaggcagaat tgcttgaacc tgggaggtgg   3900
aggttgcaat gagccgagat tgcaccactg cactccagtc tgggtgaaag agcaagactc   3960
tgtctcaggg cgggtggcag cggggtcggg ggaggtgggg ggaaggttag ctggacctgg   4020
tggcttgcac ctgtggtccc cagctacttg ggaggctgag gtgggaggat tgcttgagcc   4080
caggaggttg aggctgtagt gagtcatgtt tgcagcactg cattccagcc tgggcgacag   4140
agcaagaccg catctcaaaa caaaacaaac aaaaggtgaa attttggaat taggaaagat   4200
gctattttta taaattggct ttaagctgtt ggctggacat ctaagttgta gcattctgaa   4260
ggcagcagag atgtgggatt gtaggactga aacatgaaaa tgcctatcga atttttttta   4320
aagtctttaa aggagagctt taaaggaaag caatacgaat tcaagtatgt ttcagtacca   4380
ctcctctctc taaagacaat caactatggt tttcattcaa aatactatta ctctaacgtt   4440
aaatatttga gtacagcaat catttcagat gcattatgaa taagttactg aacacgcctc   4500
ccatctgctt gctttacggt tttattttgc ctttcgtttg ttagctcatt ttataatttg   4560
ttacttctga acaccttcca agtgctggtg ctttcagata tctacctcaa agtattattt   4620
gtaaatgtca aaaagtccct cttacatata attgaaagct ggctacatgg tagacaatat   4680
gatcacaaac ttttaaacaa ttttttaagc tgaagaaata ctttttcttt ttataagtat   4740
caaatcaaaa tgtaattcag catccaccca taaagcgcaa ctaaaaactt ttcacaatgc   4800
cattaacaac ttgtggttac catcataagc ctacagacct acacactaat tatctttaaa   4860
```

-continued

```
acccttatta ggctgggcgt ggcggctcac gcctgtaatc acagcacttt ggggggccaa   4920

ggcgggcaga tcacttgagg tcaggagttt gagcccagcc tggccaacat agtgaaactt   4980

catctctgct agaaatacaa aaattagcgg ggcgtggtga cagggtgctc taaccccagc   5040

tacttgggag gctgaagcag aaccacttga acacagccag gaggcagagg ttgcagtgag   5100

ccaagattgc accactgtac tccagcctga gccacagagc aagactccgt ctcaaaaaat   5160

aaataaaaat aaaataaaac ccttattaag gatttaaaaa atcttaatta tataatgcca   5220

aaagctagtc cccgtctggc ttaggggccc acaagctcct gctttaaagc cagttttttt   5280

gtttttttct gatgtactta catttgtgcc tcacaatcaa gaggttccca gcttggtgga   5340

actttcaaag atgaggcaga aaactaaaca ggcaattaca atcttacttt tcacgctgac   5400

aagtggtacg gtggctagcc caaactcccc tccctgtccc agctacctcc cttatagacc   5460

attcacgatc acttaggcca ggctgccatg tgacctaaga gaagacaggg agaacacagc   5520

atttcttact cctactaact tgcaacatca ttctctcaag ttgctctcat tggaggctcc   5580

caactgcttc aagctgccca gtgatatttg tatttctaaa gtgggcaggc atggccattc   5640

cagaaaaaga aacacattca gacttgtgcc ttttgttacc caaatatatg atattcaaat   5700

aatttctatt ttaacaactc ataaaaattt aagatcaaat aattgcattc ttgaaacaat   5760

tcttaatcat ttattttcaa cacgtgtact ataaagaacc taagaaatca gacaatttta   5820

ataacccata aacatgttga atccatttgc agatttaaat tttgtaaaaa tagctgtcac   5880

tgcctccata tatcaagtgt actatgttta taatcacatt tatgctaccg atactcctca   5940

gaaaaaaaca gattctgctt ggttctagct tcagtattat gaactccaat aatgctttga   6000

ggacctccaa aggaaaaaaa cagattctac taggttctag ctgaaatatt atcaactcca   6060

aattgaagct gaagtattat caactccaaa taatgcttcg aggacctcca aaaaaaagag   6120

attctgcttg gttgtagctg aagtattatc aactccaaat aatgcttgga ggacctccac   6180

aggtaaacta ctaatccctt tggccattta ttgagacaga cagagagaga gagagagagt   6240

tttgaagcaa caatgtacca ttagtaaagt tgctgtgcag aattacctca gtcctattct   6300

aagcttacag ttcagttgat tttattgtct tcacctaagt atatacaatt cacatatggg   6360

agaaaaacac taaatcaaga tggttatttt cactgttttg cttaagattc atatttaaat   6420

ataaatcaag aagttaatcc acagtttgag agatacttat attagaaatt ttaaatgtta   6480

aatacataat tgtaaatatg gtgtatgtac tgtttcacat acaatgggta ttgatcaaat   6540

cagtgtaatt agcacaccca tcagctcaaa tatcatttat ttgtagcaag aacattcaat   6600

acattaacta tagtcaccct actctctctc tctctctctc tcaataaatg gccaaaggga   6660

ttagtacttt tacctttgga ggtcctcaaa gcattatttg gagttcataa tacttcagct   6720

agaacttatt ccttcaaatt taactctgta cccattaaaa gtggttttgt gtgcaattaa   6780

cagacacatg ttctacccat acattgtttt ccaaaattat tgtgtggctt taaaaaaaaa   6840

aaaacccaca caacaaattg caaaaggcac tgagataaca tctgcttcta gatcattgct   6900

aggctcgaaa aataaagctt gttctaccag gaatgacaag ttagaactta gtatttgcca   6960

aagcagaaat tatatagtgt cagttatttc aggcaaacct tattcggctc tcatccccaa   7020

ctatctgtca gaacaattaa aagagatcaa aacagtccag cataactagg cttcattata   7080

taaggccatt ttgttctaag acactaataa accaaaataa gaaatattaa aatcaaaata   7140

aaagatatta tttgagctat tttcatacaa actgttggtt ccttatatcc tcccttctat   7200

aataaagggc atattttact gcaaagaaaa ttttacttta tatatatcac tagccataaa   7260
```

-continued

```
tttttgaatg tcattaatta catgttgtct agtaccatta accaaatagc gtaactattt   7320
tatgtccaca tttcacttct gtatttacaa acatatcagt aaagagttaa caatgagatg   7380
cgatcaaaca tccatattat ctgttttgta gacagcaatg tagatgattt tgtaatcacc   7440
tttcatcgga gtgaccttat ataaaaaata agtcaataat ttagaggttc taagtctcca   7500
aaggagattt tcaaatgtaa atatagaaat ggttatagat aatgagattt ttaggaaacc   7560
tctgccatgt ctgcatcctg ttaactgtta tatcatcttt tcttccagct gcgttccttt   7620
gcctgcaaca ggggtcaaga tgagttttgc ctgacttctt tgatgtcctg aactttccgt   7680
agtccttttt cttgaatttg ttcattataa atatagcttg gcatttgttt gatcttttca   7740
actgtcttca ctgcatcagt agttttattc catagttctt gcagatattt gacaggcttg   7800
ttactatatt tttcaaattc aaatccactg taagctcatt attagcagtt gctttacaga   7860
atgctttagt ccacctaacc ttttgagaat tgcacttctt ttaaagtttt tgtgacattt   7920
atgtttatac aatctgaaca ccttgcaaca gctgcagatg aacatcatga tgtggtcagg   7980
gtagatgggt cccaaagaaa ctaacacttc tcagtgctga gctcggatgg gcctccactg   8040
accaaacacg gagcttgaga ggaagtcaag aggtatcttg gaattccaca tgctgaccct   8100
gtcattcttg aaggaaaatg atgcataatt tctgaataat tcagaaagaa cttaacaatc   8160
tttccagtta gtttttaaat aacaattctg tttatcaaat ttctgaatta acttttctga   8220
attcacgggt ttctaaaact ggccttaagc aaaagtctga aacctaggct gggaaccatg   8280
taacccaggc caagaaggta ctttaaagtg tcttagagtt gtttttcaac ttagggggaa   8340
acaacagatt ccattaaatc ccataaagga tttttttgtg tgtgaaaaag ggcctgatgt   8400
aatctaggtt agactcagga ggctttaaca agttttgtct tacgggtaaa tggtggctat   8460
tttcacagat aacatcatta ctcccatccc ttactatggt ttatacaaaa gaggctggag   8520
aataagtaca tttttacagc cgggtgtggt ggctaacgcc tgtaatccta cttagcactt   8580
tgcgaggcca agacaggagg atctcttgag cccaggagtt cgagaccagc ctgggcaaca   8640
cagggagacc ctgtctctat tgttaaatca agaaaaccta aaaaacattt tcatttacat   8700
agcaccaaat ataagagcct tttttttttt aacctagaaa gagtattttg gagagagaaa   8760
ctaaggatca gaaggtttaa gagtatcaaa aatctgaggc caggtgcctc acatctgtaa   8820
tcccagcatt ttgggaggct gaggtgagta gatcacttga gtttaggagt tcaagatcag   8880
cctggctaac atggtgaaac cctgtcttta ctaaaaatac aaaaaaatca gctggtatgg   8940
tggtacatgc ctgtaatccc agttacttgg aaggctgagg caggagaata gcttgaaccc   9000
agaaggcgga agttgcagtg agccgagatc actccactgc actctagcat gggtgatgga   9060
gcaagactct gtctcaaaaa aaaaaaaaaa aaaaaaaaaa aagagtatct aaaatttaaa   9120
tactaattct tggctggaca tggtggctca catctgcaat cccagcactt cgggaggccg   9180
aggcgggtga cctcacttga ggtcaggagt tcgtgaccag cctggccaac atggtgaaac   9240
cctatctcta ctaaaaatac aaaaattagc tgggcatggt ggtgcatgcc tgtaatccca   9300
gctgctccag aggctgagcc aggagaatgg cttgaacccg ggaagcggag actgctagat   9360
catgacactg cactccagcc tgggcgacag agagactcat ctcaaaacaa acaaacaaac   9420
aaacaaacaa aaaaacaaaa aactaaatct ttcacacatt ttctctttat atcaaaggta   9480
ctaagtgaca tttaggccgg acgcggtggc tcatgcctgt aatcccagca ctttgggagg   9540
ccgaggtggg cggatcacga ggtcaggaga tcgagaccat cctggctaac acggtgaaac   9600
```

-continued

```
cctgtctcta ctaaaagtac aaaaaattag ccaggtgtgg tggcagatga ctgtaggcca    9660
agctaattgg gaggctgagg caggagaatg gtgcgaaccc gggaggcaga gcttgcagtg    9720
agccaagatc acgccactgc actccagcct gggtaacaga gcaagactcg gtctcaaaaa    9780
aaataataag ttacatttaa atgtcatata catatttaag aaaaaaaaaa accaagtact    9840
tctcatttaa gacagagtag aaattattta aaattaggag ttggtgtaaa ggatgagcta    9900
catattcaag tcaaattata gtaagtattc actattccac taccaaagta ggtcaattat    9960
actaaagaga agaaatctat gtgaattgag gcattttctc actttgatat atgtgaataa   10020
atttcaggtt gtctaaattc ctagggttat atagttagaa atatataatt ctcttataga   10080
caggtcaact aggggaaata agttagcaca atcatttgaa ttggttgtct acatactggg   10140
cagggcttat tccttttctt tagcttcttt gcacatgtaa agcaggccat aagatgtcct   10200
gttttgccat ggacaatgca accattttta ggtcgacctt gacaaatcac acaaggttca   10260
atggcattaa ggggcaaact agattccaca ctctcttctt tgtcttgggt ttcttccctt   10320
tcaaactctt tcacatcttc ttggctgcta taaataatgc tactagaagt tgatggctga   10380
gaatagtctt cactttcttg tgattgtgaa gcttgtgtaa ttttatcatc attttcctca   10440
acacatgact ctctggaatc attcactata gtttttttac aatcaggaac atcaaagccc   10500
tcttcagctt gtgttgagtt ttccagtttg gctttctcag agatttcccc tttatctttc   10560
cctttatctt caggaagcca attctcacga agggcccaac atctgttgca atgtgatgga   10620
aggggggat tcatttcatt gcatgaagtg catttccaat agtccttcaa tgaaataaga   10680
cacacagtca gtttctgtaa ccctttaact gctcagtcac aggaatgcta gcaactttgc   10740
tatgtctaag gtaaagtata tcatagggct caatattcag tgtttcatgt tttatataaa   10800
atagtcactg taaacagcat gaggactata gttagttata tattggtata ctggaaattt   10860
actaaaagaa tagattttag gtattttaac catacacaca agaaaggtta actattcaag   10920
ataatggatt acattaattt gcttgactgt agtgatcatt tcactattta catgtgtgtc   10980
aaaacatcac gttatatgtc tcaattatac acaaaacaga tttttaaagg tcaatatgta   11040
acagtctctc ctaaagtaga gtaagtacac ccattttttt caccccttacc atcctgaaaa   11100
attctaaact aaaaatatat taactgtgat gtgatattaa tcatgtacct ataaagttat   11160
ctgtttcagg atacaaatgc agttgcttcc tttagttgaa gcaagtctat gggatctttt   11220
actctgtcat gcagcctata tccactccct taaaggctca accctaggcg ctattccaag   11280
agtccatccc atcaatctag atgaaacctg cctcctcgag aaagacttcc taatccacca   11340
gtgactagaa ctaccttaga agtactctaa aaccatggct taactgagta ttccctaact   11400
ccatccacaa gagaaatgct aaaacatttt tcacagcaag tattgctgct aaaacctatc   11460
atccttggtc actaaccgta atatcctttc ctttacctgt ctatcctttc ctgtgttctc   11520
atctttgtaa ctgctcaatg cttcttcctt ttcccaacgt tttatcccac aaacctttcc   11580
accatgcaat ttggataaca aactctccca catccccagc ctttttacat aacctatctt   11640
cttgccttag ctgaagcatg gttcttgcct gaggacattt aacaagtgaa aactcttaag   11700
taagaggtat ttccgtaacc attttgagat tgcctcacaa atgatgttaa gacaggagca   11760
ataaagatag actattcatt cttctttttt caagttatag aagggggttt ttcacagctc   11820
ataaaaccaa agaaaaaggt cttgcaatat gggagtaaaa gtgcatcaaa aagtccaata   11880
aattccaaga tgaatatcta aaataatttg agtcttaaaa tagatttaaa aaattaaaag   11940
tatctaaaat attttactca acttgacatc aaatgattca attagttatt tattttctaa   12000
```

```
tacagtaaaa attttggaaa ctcttgaatt ttcatccttt tttgcacttg aataattagt  12060
aactgtctat aactcagaaa aaatggaatt tatttcctat tcaaatataa taaaggcaat  12120
attaagaaca aaaactaaag cacaatagtt ttaaaaaaac ctataatacc tcaggaactc  12180
agtgaagtat gcatgagatg taaacattta agtgttaatt tctttaatgg caaatcctac  12240
cacattctat aatacaaatc agtaataaaa atgtttacat ttggctgggt gtgatggctc  12300
acacctgtaa tccttgcact ttgggagact gaggcaggtg gatcacttga gcccaggagt  12360
tcaagaccat cctgggcaac atggtgacat ttctacaaaa aatacaaaaa ttagctgggg  12420
tgtgatggca tgcacctgtt attccagcta ctcaggaggc tgaggtggga ggatcacttg  12480
agcctgggag gtgggggctg cagtgagcca tgatcacatc actgcactcc agcctggaag  12540
acagggcagg accctatctc aattgaaaaa aaaaaaagtt tacgtttgac aaggttggca  12600
aaatgttggt aatagttaaa gctgggtgat gagtatactg gagatacact gaaattttcc  12660
aaaataacat caaaatgtac aaattcagct gggcagtgac tcatgcttgt aatcccagca  12720
ctttgagaga ccaaggtggg cagatcactt gaggtcagga gttcatgacc agcctggcca  12780
acatggtgaa accccatctc tactaaaaat aaaaaaatta gtggggtata gtggtgcatg  12840
cctgtaattc cagctactca ggagactgag gcacgagaat cacttgaacc tgggaggtgg  12900
aggctgcagt gcactgagat tgcaccactg cactccagct tgggagaagg gtaagaccct  12960
gtttaaaaaa aaaaaaaaaa aagttcaaat tccagcacct aaaaataaaa attatagcta  13020
caggtctcat cacaacaaat aaaagaaaaa tgctttaaat tattcagact ttacaaaaac  13080
attttaactt tataaaaatc agttcatttc agaaagaagc tagatatagt ctcctaatct  13140
tgaccttaat gaaattttta tttcttaaaa aagtagatgt atacttacag ctaaggaaat  13200
ttcaggatct tcttcaaatg aatctgtatc actctcccct gcctgataca cagtaacttg  13260
atatacctaa taaaacacat tcattagcat caattcatcg ccctatttcc ttcaatcaga  13320
aggcttccta gtaataagtc ctaaacaaat atcatgtact acaatatatg agaaagcctt  13380
agacaatatc aaatagagta agtgagtgta aagggggaaa aaatggagga gagagaaatc  13440
cttacccaca atggtaaaag tcaatacaaa ggatgtttag gatgaataaa acaaaacatt  13500
cagctaggtg gttttacttc ataaataact aatatggaga tattaaataa tagggaaata  13560
gctagaaatg ttaaaggcag tcacttctgg gaaacagatc tctaagggta ctacttgact  13620
ttaactgtat gcatgtttta cttttataga aagtaagtta atattaaaac agtagttgaa  13680
ttatatgttt ttaaaagtga acagaccatt ataataagca tgttcattga ggtctattga  13740
cttcttggca attagtagta atataataat ataaatcaga tgataaagaa ctatgaaatc  13800
ctcaagtcca caaaccaatg tgttagttta aacaaatcaa gaggtaaaga tttcaagtga  13860
aatctgaata atattatttc aatctcaaag tcaatgaaca tagaaaatat ttaataattt  13920
tccaatataa ttagagggga aaaaaaatac tacctcatca tcttcatctg agagttcttg  13980
tccttcttca ctaaggctat aatcttctga gtcgagagat tcaacttcaa attctacact  14040
aaactgatct gaaactgaat cctgatccaa ccaatcacct gaatgttcac ttacaccagc  14100
atcaagatcc taaaacaaga aaaaaatata taacttaata aacatcacct cttgacctct  14160
gtatctgttt cctaactcat ccctgtgcct ctgctgctgc cagcagggtg taacagttgg  14220
gggatgggcc tgctgctctg atccgggact tcccgaggga gatcggcggg cagaagacta  14280
ggccccccag ccagccatcc cggagccggt tgccacgcac atttcctcct cagatccatc  14340
```

-continued

```
ctgcatactg aaactagatt aaggtttcaa ggttattact acattatttt ccctgttcaa  14400
aaccccactg cataaaggaa aaacaccaaa gcctcttggc atcgaaagta cctacagtgt  14460
gactgtatta acatcttcgt ctgtcttcaa ctagacaccc ctcctccctt actaaatatg  14520
gataatcccg ccagatctag attgcttcct caactaatct tggcatttca acttccacac  14580
tttccccctc taactagaat aatttcagtt tcaaaatcct attcatcctt ctttgactaa  14640
gcctttgtca ataccataac tgaaaaggct cttccacctt taattatcct tactacttgt  14700
ataataatga attatatagt ctcacacata aattatgcaa aacataattt tgcaggcatg  14760
tttctcatct gaattatata tactttgagc taaaacctgt cactcatctt tctatgtcca  14820
aattggtaga atacacgtaa caagacacaa cacttgtaat acttatgggt tttttttctt  14880
agaaaaatgt ctcgagtcat agatacttat gtttttttaat aaactttgag attttctttt  14940
aaagagcctt tagacaatta aaaaaaattc tgtagctgct catctgattc ttcgtttcag  15000
gacttcaata aattgtataa gaacctagta agaccttcag ggcaataata tttgctgtca  15060
gtggctaagg gtaggagcat atataagcag aaggctacaa ttggaaaaag tctagaagtc  15120
gggatatggc ttattctaca cttgccacta agtagctaat ttaaccttaa acaacatcat  15180
ttaacttatt ttatttattt tgagatggaa tcttgctcca tcacccaggc tggagtgcag  15240
tggcctgatc tcagctcact gcaacctaca cctcccaagt tcaagcaatt ctcctgcctc  15300
agcctcccaa gtagctggga ctacaggcgc atgccaccat gcctggctaa tttttgtatt  15360
tttagtagag gcagggcttc accatgttgg ccaggctggt cttgaactcc tgacctcaag  15420
caattcaacc gccttggcct cccaaagtgt taggattaca ggtgtgagcc accatgcccg  15480
gcccttttttt tttttgagac aagagtcttg ctctgtcacc caagatgaaa tgcagtggca  15540
tgatctcagc tcactgcaac ctccgcctcc ggggttcaag ctattctcct gcctcagcct  15600
cccaagtagc tgagattaca ggtgtccact accacacccg gctaattttt atgtttttag  15660
tggagacggg gtttcgtcat gttggctggg ctggtctcga aatcctgacc tctagtgatc  15720
cgccacctcg gcctcccaaa atgctgggat tacacctgtg agccacctcg cccagcccat  15780
atcatttaac ttctaaaggc tgtagctact tcatctagaa aaggagctta gattaaatga  15840
tttccatatc tgtatcagtt ttaaaaacag aaacaaagta tattatttta cagcctctga  15900
catcaaaaga cttttttaga gtaatgttag gaaggagagt aaaagcaaca ttcatcaagt  15960
tgcagctcaa attcctaaca agggctctac taccaatcag attagaatca caagtcaagt  16020
taggatacaa ttaacactaa caaagtaacc caacaaacca aatacttcaa ctaactaaag  16080
tctttagtgc actaatttta gaataagggg gtaaatcaca agaaacatta aatctcagaa  16140
aacatactct acggtagggg tctgcaaact gtggcccatc acccatcgac ttttataaat  16200
aaagttttat tgaacacagc catgcctatt tgttgacttg ttgtctacag ttgctcctgc  16260
attacaagag cggggctgag tagctgtgac agaaaccatg gcccggcaga gcccaaataa  16320
ttaactatgt ggctctttac agaaagtttg ccaactcctg tcctaggata ctataaaaat  16380
actataaaaa ataccatgaa aaaatgcaat attgggagtg gtttttaaag ttttggctaa  16440
tgttcgcaaa agaatgcccc agaaactatt aaattatctc tctctatata tatttttaaa  16500
atatataaaa taaatattta aaatatatat ttatatttat ataaatagta atatatataa  16560
tatatacagg tgcctgccca tttatattta cataaatata tatttttata tttatataat  16620
tatattttta tatttatata aatatatata tttatattta tataaatata taattatata  16680
aatatatata acaatgtaat atataatata cattaatata taatagattt ataattatat  16740
```

-continued

```
attatatatt tatacattat ttaaatataa atatatatat atatatattt ttttttttt  16800
ttttttttt tggagacaga gtctcgctct gtcacccagg ctggagtgca gtggcaccat  16860
ctcggctcac tgcaagctcc acctcctggg ttcacgccat tctcctgcct cagcctcccc  16920
agtggctggg actataggtg cccgccacca cgcccggcta attttttgta tttttagtag  16980
agacggggtt tcgccgtgtt agccaggatg gtctcgatct cctgaccttg tgatccgccc  17040
gcctcagcct cccaaagtgc tgggattaca agcatgagcc actgcaccag acctaaatac  17100
tatatattta aaaagcatca ggctggaggt ggtggctcat gcctgtaatc ccaatactct  17160
gggagccaaa gcaggagaat cacataagcc cagcggtttg agaccagcct gggcaacagg  17220
ccaagatctc atctctgaaa aaaaaaaagt aaaaaaaatt agccaggtgt ggtggtgcac  17280
acctgtagtc ccagctaact ctcaaggctg aggaggaagg attgcttgaa cccaggaggt  17340
tgaggttgca gtaagccatg atcatgcgct gcactcccgc ctgggcaacg gagtgagaga  17400
ctgtctcaaa aatttaaaaa atatatattt ttttaagcat cagataggct tgctctgcaa  17460
agatcttaga tctttgtagt caaaaatacc tagaattgtt tgaattccaa ttgtgacaat  17520
tagttgtagg aaccttaaac aagttattta aaaccccagt cttagctaaa aatggaatct  17580
gaggctgcaa agatgacaga agatcataat ataaactgca tggtgtacag tctagaacac  17640
agtcttagtt tcccacaatt tattaaaccc caaagaaaga aaagatggga gaggaatgca  17700
ctttccttta actcccttca caaactggtg aatgatgaca cccaatgatg actacaacat  17760
tctcaaatga gggaaattaa aacgaagaag aaaaaaaaac tggccctacc aaaagctttc  17820
acaactaggg acttaacctg aaaaacgaga ttttgttgtt gttgtttgag atggaatttc  17880
gttctcgttg cccaggctgc agtgcaatgg cgtgatctca gctcactgca acctccgcct  17940
cccgggttca agcgattctc ctgtctcagc ctcctgagta gctagattac aggtgcccgc  18000
cactatgccc agctaatttt tggtattttt agtagagatg ggttttcaca acatgttggc  18060
gaggctggtc ctgaactcct gacctcaggt gatccgcccg cctgggcctt ccaaagtgct  18120
gggattacag gcatgagcca ccacgcccgg ctgagatttt ttatagatag gattttttaa  18180
gagaatgcag gacaggacta acaaaaagaa aaaaagaaat acccctctac tccacacgag  18240
ttattaagaa attattttag gcaaatggag aggaaaagtg gtccttggaa ggtttttcgt  18300
agctccagaa aaatttcttg tctagcataa aagccctggc tcttaaaggc tggcaacctt  18360
taagatgcaa atgcaagagg gtccacccaa catggcgatt cccaccgttg tcctcttgcc  18420
cttgctccat caggtaccta acagcatggc cgcccccaca taaccccgtg tgtaaaatgt  18480
catggcatcc tgcatttgtg tattaaagga ctggggtggg agggccagtt ttcttgaggg  18540
ctaaatgaca tgcctggtca aaccaatcct ctgagcccta tgcaaataag acaccacccc  18600
ctccagccgt cacataaaac tggctagtat tgtcagaatg taaggtctcc tctttcagct  18660
ttagagcccc cctccctctg tctgtgtaag ggggagcttc ttccttctgc cttctccctt  18720
cttgcctatt aaacgctctg ctccttaaaa ccactccacg tgtgtccgtg tcgttttatc  18780
taattcaact caaaacaaaa aacctggtgt tcctctactc ctcaaagcca tatcagtaac  18840
aaggcagtgt cccaggtaca aagcaggaac aaggactcta aatatcattc agctagaatt  18900
ctgatataac tttaacaaaa actatacatt aaataggggt ccgggcaggt ggctcacatc  18960
tgtaatccca acactttggg aggccaaggc aggcagatca cttgaggtca ggagctcaag  19020
accagcctgg ccaacatagt gaaaccccat ctctactaaa aatacaaaaa ttagccaggt  19080
```

-continued

```
gtggtgatgg gagcctgtaa tcccagctac tcaggaggct gagacatgag aatcgcctga  19140
accggggagg tggaggttgc agtgagccaa gattgcacca ctgcactcca gcctgggaga  19200
cagagagact caatctcaat aaataaataa atagggtata ataattctct ttttaaccaa  19260
acttgtaggt tggatactca tcaagtttta attggattca attttatcac atatatttcc  19320
gctcaagagc ctatttttc cactggattt attaaatgtt ttcatttttg tcattaatga  19380
tctatctccc aatgaaggca agaaccatat ctaccttgac taccactgta tctgcagtgc  19440
catctcaact gtatggaatt tggtataaac ttaaatatct acaaatgaag aacctgctct  19500
cagactgagc aggagctcat catgccatct agcggtctac ataagtaaca gctccgttag  19560
gtacagtaac tctagagggc aggtatgcgt tcatacaatc actgctttgg aagagaaaaa  19620
aagataatac aggaagtaac aagaataggt aaaagactag gattactatc acaattggtt  19680
ccacttccta catcttctag agtactatac aatgattact aatacccaga ataatggcca  19740
tgagacactg ccatattacc aaaaaatgta tccaatcctt tggtttccgt gggcgacatt  19800
ggaagaattg tcttgggcca cacataaaat acactaacaa tagctgatga gcagaaaaaa  19860
aattgtaaaa aaaaaaatca taatatttta agaaagttta tgaatttgtg ttgggccaca  19920
ttcaaagcca tcctggcata tggcccacag gccatgggtt ggacaagctt gattaaagac  19980
atacaaaaca aaatattcca tttgtcaagc attcttgtta acaaaaaaat tttttaccaa  20040
acttctttca gtgacatctc ttaagaaatg ctgctcacta atattttgga agtctgtatt  20100
agtaatgaga aagtactgat actctcccgt catccatgca ataataaacc tgcatttttt  20160
tttttttttt ttgagatgga gtctcgctct gtcacccagg ctagagtgca gtggcacaat  20220
ctcagctcac tgcaacctcc aactcctggg ttcgagcgat tctcctgcct caggccccca  20280
agtagctggg actgcaagca tgcgccacca cgcctggcta atttttgtat tttcagtaaa  20340
gacatggttt catcttgttg gccatgctgg tcttgaactc ctgacctcag gtgatccacc  20400
cgcctcagcc tccgaaagta ctgattacag gcatgagcca ccgcacccag cccagtataa  20460
acctgtattt tacagcataa gtaaatagaa cttacctgat gtctagacct atttggcaaa  20520
tgttaagttc agactatgct gactttttg ctgatggctg taataaaata tatttttact  20580
ctaaatagtc aaatttgcct taaaatgcta aaatatttaa ctgaaccaaa tttttggttt  20640
tgttcctttt ttaaaaagtg taactctcaa attctcaaac aactctatac tccaatttat  20700
ttgactgtac tattggtgca gtggtccaca aatattctct aatacataca gtgacattga  20760
taattactaa tactactact aattttacca ataccggtgt tactccacta ttttccacat  20820
ttctcacaat accttgggtt gaaggtggag atcaatatag tagttttatt ttaaagtaaa  20880
atttagcact gtgttttcta tcaatctcgt aagacacatg tacattctat ccgtatcctt  20940
attaggactg ccaggactag actttgaaca gtaagagtct tgccttactt aaaatgagaa  21000
cattaccgga ttcgatggcg tccctgtaga ttcactgcta ctgcttcttt cacaacatat  21060
ctcccttatt acacacagag ccaggctttc atcaaaggaa agggaaatac tatcagattt  21120
gtggcgtttt ctttgtcgtt caccagataa ttcatctgaa ttttcttctg gatatgtaag  21180
gaaaaaaaat aaattgctgt actgtgattt agaaaattga gctgttttga gtacctattt  21240
gtacagaaac ttagtttcaa taaaattagt tcaaaagtta acactgtttt attgaatctg  21300
tccaactgtt acagcagaac actatctgtg tgtatttatt tatttgttta tttatttatt  21360
gtctgagaaa gggtcttgct ctgtcaccca ggctggagta cagaggcaca atctcggctc  21420
actgcaacct ctgcctcatg ggctcaagtg atcctcccac ctcaacctca gcctcccgag  21480
```

-continued

```
tagctggtac cataggaacg gtaccatagg aatgcaccat tttgtatttt ttgcatagac  21540
agggtttcac catgttgcct aggctgagaa tactattttt aaaaagcttt ctattcttct  21600
ttcagaactt tatctccata catcacaatt taatctatct aataaagttt ttattaacca  21660
aaaaatctag gaattttttt ctgtcaaaac caaactttaa aatataagag ctcatctgtt  21720
tttttccgaa aagagccaaa gtgtttaatt tactcatatg gtattcttaa tgtttcaatt  21780
tcttcagtac cctacacttt ttcttttgag acagagtcac actcgaccac ccaggctgga  21840
gtgcagtggt acattctcag ctcattgcaa cctctgcctc ccaggttcaa gtgattcttg  21900
tgacttcagc ttccaagtag ctgggattaa aggtgcacac caccatgcct ggataatttt  21960
tgtatttttg gtagagacag ggtttcacca tgttggccac actggtctca aactcctggc  22020
cttaagtgat cctcctgcct cagcctccca aagtgctggg attacaggcc taagccacta  22080
agcccggctc ttcagtaccc tatattttaa acagaaatca aaaccagtaa aaagtttcca  22140
tttcatttta aataataaat tatctctgaa tgggtcagaa tgttagacaa atccgttaga  22200
cataaatgag aatactacct tatactagac ataaaaatga attccaggtg gattaaagat  22260
ctaaatataa agaacaaaac cattcaagta cctataacaa aatattctta taatgctggg  22320
gtggagaagt atttcataat actgcaaagt cctcaataaa aagactatca agattagacc  22380
atgtcaaggt ttacatgaca aaataaaata ccaaacaaaa gttaaaaggc aaaggtcaaa  22440
ttcgaagata atatctgcaa catatatagt aaaaattacc catagtatac atattataca  22500
aagtcctacc aaatcaagat agactgtatt ttcttttaag gaaacaggaa aaagcaagtc  22560
acagaagaaa tacaaatgac taataaacat atgaaaaatc ttgagtcatg tacttgagta  22620
atagaaaaaa aaactcttac ctcctaggga tcaaagaaat gcaaagtgaa atgatatcat  22680
ttttcaccca tgagaatgac aaaaaattaaa atgagatagt atcacagatt tctgaaagga  22740
ctttttttat cattttcttg agacaaagtc tcactcttgt cccccaggct ggagtataat  22800
ggcacaatct cggcacactg caacctccac ctcctgggtt caagcaattc tcctgcctca  22860
gcctcctgaa tagctgggac tacaggtgcc caccactgtg cccggctaat tttttttgta  22920
tttttagtag agacggggtt tcaccgtgtt agccaggatg gtctcaatct cctgacctcg  22980
tgatcctccc tcctcggcct cccaaggtgc tgggattaca ggcgtgagcc actggacctg  23040
gccgggattt ttacgtttta tcgagatcac aagttctgca cgtgagttct taatcatgtt  23100
tgtgttccct atttttaaaa aggtgatctt ggccgggctg caattataaa taatgctgta  23160
attagtatct ctacatataa atctttgaat tttttattac atccttagga tagattacta  23220
gaaatggagt tactaggata atgttaagaa ctctaagact ttttttttctt ttctttttt  23280
ttttttttta agagggagtc tcactctgta ccccaggctg gagtgcagtg gtgcgacctt  23340
ggttcactgc aacctccaca tcccaggttc aagcgattct cctgcctcag cctcccaagt  23400
agctgggatt acaggcgcct gccaccacac ctggctaatt tttgtatttt taatagagat  23460
ggggtttcac catgttggcc aggttggtct cgaactctta acctcaagag atccacccgc  23520
ttcggccttc caaagtgctg ggattacagg tgtgagccac cgcaccaggc catctaagct  23580
tttttataat ccgaaaaatt taatcaattt ttacccactt ttaccaattt acagaccaac  23640
agtttatcag tgctaataca caagttatta gcactgatga gtaaggatga gtaaaaattt  23700
tatttttact aatttgatag atcaaaagga caccctttg gcattttttta ctatctgtaa  23760
agctaaaaat caccaaaatt caccctctcc ccatatttat tagtcattcg tatttactgt  23820
```

-continued

```
gagaaatttt tgtgaactgt ctgccctttt tgctatttga agttttaatg ttttccttat  23880
tgatttggga agacttttta tgtaatacag atattaacag tcaaatttaa agtgactatc  23940
tttcaaatat gttgtattct atttttcatt taacttttaa actcatttga aattcatttt  24000
ggcataaggt acagatctaa cttcaccttt tccccaagta actaccattt gttctagttc  24060
cacctctgcc ctagacacct ctgcccttcc tgtcttctgc ccgcatgtac gagattctgg  24120
tctgggttca tttattctgt ttcactgatc tgacattctc tttcatctga atcatacggt  24180
cttagttact gcgacttcct caggcaacag ccttctcgtc tactacgtct actaactgtt  24240
ctcaactatt ttctctctgt caactatttt ctctctctct cttttttttta gacagtctca  24300
ctgtgtcgcc caggcggagt gcagtggcgt gatctcggct cactgtaagc tctgcctccc  24360
cagttcatgc cattctcctg cctcagcctc ccgagtagct gggactacag gcacccgcca  24420
ccacatccag ctaatttttt gtatttttag tagagatggg gtttcaccat gttagacagg  24480
atggtctcga tctcctgacc tcatgatcca cccgcctcgg cctcccaaag tgctgggatt  24540
acaggcgtga gccactgcgc ccggccctta tctcttcatt tctaaaatgc tatttacttt  24600
ctgttttaaa actcataggt atgtactacc atttattaaa aataacaatt taaaaattta  24660
actgttaagg tgactaagaa taatggtgaa aatagagttt atatgcctgt ctcctattat  24720
ctttcttttt agacgaagtc tcacacggtt acccaggctg gagtgcagtg gcgcaatttc  24780
ggctcactgt aacttctacc tcccgggttg aagtgattct ccttcctcaa cctcctgagt  24840
agctggatta caagtgtgcg ccaccaggcc cagctacttt ttgtattttt tttagtagag  24900
atggggtttc accacgttgg tcaggctggt ctcgaactcc tgacctcgtg atccgccagc  24960
ctcggcctcc caaagtgccg ggattacagg cgtgagccag gcgtgagcca ccacacccca  25020
gccacctcct actatcttaa cagagagttg gctaactata aactccagtg gggcacagta  25080
aactgtgcct gctgtagtca gccagaaaaa tattgctaaa taagcaattt gtaaatcaaa  25140
taaaatcacg aatgaaaaaa actcagaggt taattcatct caaccaaaaa aagggaacaa  25200
tttaattaag tctaaaagca ctaatttcat tagagaaaga atatcaaaaa gctgtgtgaa  25260
tgcgtcaaat aaatattcat atatacctgt ctcactaatt gctctccttc tagatgaggt  25320
agatggtcta gaaaccaaat gtgaagatga aggtttctct tcctgaagct cttgtacaag  25380
gtcctaagca tttaggaaaa aaataaaata caacaaactt aacataacca gtaagctaac  25440
ttgttgtaaa taacctttcc aatttgcaaa taatattaca ttagaatgag aaatttactt  25500
agattacctt ttgatcactc ccaccttcaa ggtgacacct gttctcactc acagatgtac  25560
ctgagtccga tgattctgag agaaaagaaa aaggatcaga aacttggtgg tgggcggggg  25620
gcggcggggc gctactcagt agatatgcta tcagtctaac acaaaccctt atgcaattta  25680
acctttcaat aaacattaaa catgtatttt ccaggtggca tcctcatact aaatgttgca  25740
gatgtaaata aaataattca actttaatgt agaagagtaa agtataatca agacattaaa  25800
agactgttag ataaattagc agagagacag gagagtcatt attttggtag ggacagggag  25860
tgtctgagaa acaaagaatc aggaaatatt ttgtaggaca atatgaaaat agggctagga  25920
aaggccattc cagaccaaga aaacgccatg tgaaaaagta tccaaaagca aactaacaac  25980
agttcctgtt gcaggacacc acaagcagtt cattattact ggaatgtagg caggttcaga  26040
ctgtaaagga tcctgtggtc tagccaaagc aggactcatg ctgtcattcc cttatcactg  26100
cattcttccc cgcagatact tcagaatctt ccttaatgcg atgttgcagc cactcaccat  26160
taaaaaggat tttgtccaa gaaatgaaac tgatttctag ctcacagaaa atattacatc  26220
```

```
cagagagcaa taatgaaccc ctaaatggta attttaagca gaagagtgac aaatcactct  26280
agcaaaacat aagaaaaaga gggcagaggc aggaaaacca gtattagaca attgcaataa  26340
tacaaactaa aaactattaa agcctaaact aaggcatgga aaacaaattc cagagaaatt  26400
aaataggtaa aaaccaacaa gacctggtat ttgatataga aggcaaggaa gaaaggagtt  26460
aagatgattc caagattcca acttgggtga ataaatgagt ggtaccattc actaaaagag  26520
aaactttaga aagataaaca gattggatgg gaagataaca aactgagtta ttcaggcaca  26580
taggtttcat ttgtagttgg atatacagac tttgagctca aaagtcaaag tttcagagtt  26640
gggatataca gacaattatc atcaaatacc ctttactacc ccccttggaa acattttcat  26700
cttaacagtg aactcatgcc tggacattaa cattttgaaa ttatgcatta tcatagatta  26760
attttctctt tatactatgg gtaaggcatt acactaattt tcttaagttg tacataatag  26820
gttatattgt ccaggaattt tggattagta taaacagatg ctacaaaaaa gatgtaataa  26880
aaaggaagcc ctaggctggg tgggtgcagt ggctcacact tgtaatccca gcactttggg  26940
aggccaaggt gggaggatca cctgaggtca ggagtttgag accagcctgg tcaacatggt  27000
gaaacccttt ctctactaaa aatacaaaaa ttaaccggac gtggtggcag gcacctgtaa  27060
tcccacctac tcgggaggct gaggaaggag aatcacttaa acccgggaag cagaggttgc  27120
agtgatccga gatcgcacca ctgcactcca gcctgggtga cagagtgaga ctccatctca  27180
aaaaaaaaaa agtgacaaag ttgagaacat ggaataggag ttctgaagtt aattctactg  27240
atatctaaac caaactcaga ctgcaaataa gtaatttgta agtttccatc tcaataatac  27300
aatttttcta gtaatgtgcc aaagtttatt taaacaaatg aaggaatgaa tacatcaggg  27360
ttacatactt cagaaaactc aaactactac tacaaatact acaattgtat atttagctat  27420
cacacaattt cttaaagagc tttaaaacaa caggtataca tatgtaacca acctgcacat  27480
tgtacacatg taccctaaaa cttaaagtat aataattaaa aaaaaaggaa ataaaaagga  27540
tacaatctaa agctcaaaaa aaaaaagagc tttaaaacaa taaaatgcca aatcatcagc  27600
ctaataacta cttttatttt gggataaaat ggagatactt ttctgggctt taaatcctaa  27660
ctttggaaga ataagtattc aattcaacac atttattaaa taccatatta ataaaacact  27720
atagtgtgtg atgcacaatg caaacctgaa taggacacag gtaacaaaaa tataaacaag  27780
tgcaacagcc agacgcagtg gctcatgcct gtaaccccta aactttggga ggccgaggtg  27840
agaatatctc ttgagctcag gtcaagacta gcctgggcaa catagcaaca ccgtctctac  27900
caaacataca gaaaaattag ccaggcgtgg tggagcacat ctgtagtccc agcaacttgg  27960
gaggctgagg gggaggatca tttgagccct ggaggtggag gatgcagtga gccaagatta  28020
ccactgcact tcaagcaggg tgacagagtg agagcccatc tcaaaaacaa acaaaaaaac  28080
ccacaagtaa aacaaagcaa ttttacaata aaatctgaat atggaataga ggaagtacaa  28140
gggagtggtc aattcattct aggaactaaa caagctcctg agaggtgttt ttttgttttg  28200
ttttgttttt gtcttttta agagatgagg tcttgctctg tcacctggac tggatggcat  28260
gatcacagtt cactacagtc ctgacctccc agcctcaaaa aatcctcctg cctcagcctc  28320
ctgagtagct aggactacag gcatgcacca ctataccaag ctgatttttg tagtttttgc  28380
agagttagga ttttgccatg ctgcccaggc tggtcttgaa ctcctcggct caagtgatcc  28440
tcctgcctta gcctcctaaa gtgctggaat tataggcatg agccatcaca cctggcctaa  28500
gagcatttct taactgtagt tcgaggatgg gctttaggag cagtgtagtg tattagagac  28560
```

-continued

```
agctctaagc agcactcaaa agcaaactgt gagaccgggt gcagtggctc atacctgtaa  28620
tcccaggact ttggaaggcc gaggcaggca gatcacaagg tcaggagttc gagaccagcc  28680
tggccaacat gctgaaaccc cctctctact aaaaatacaa aaattagccg ggcgtggtgg  28740
catacgcctg tagtcccatc tactcgggag gctgaggcag aagaattgct tgaacctggg  28800
aggcggaggt tgcagtgagt cgaaatcatg ccactacact ccagcctgag tgacagagca  28860
agattccttc tcaaaaaaaa aaaaaaaaaa aaagcaaact gtgtacatct cttcccaact  28920
ccatgttttt agccttcaaa tgagagtatt atactatgga agtcagcaag cacataaatc  28980
agggcttttc tcatggaaag taggttgtaa aacacttatt gacttaccca tgtatatata  29040
catgtgcatc tttctggaac aagaacccaa tgcttttatc agcttattaa agagagatgt  29100
gacccaaaaa taaccagtta agaaacggaa gtaggaacat aaaattccac ttccacaaat  29160
tggtaaacaa aattttgtct ataaccaaag aaaaagactc atccttcatc cttacacatg  29220
gtcctaccta ggtaacaata ttatttccca aagcctttca atacattttc aaggtagatc  29280
actcctaaac aggagctttt gaaattacag acctttcaaa ataaatccta actctgatat  29340
cccaagtcta aattgatcta acaggatatt taactttaca ttagaacctc agtatgtggt  29400
tttagttcat atgtacttct aataaattta tcatactttt attacaatat ttaattaaag  29460
caacttttaa agagaatcac aattataaaa catatgcaca taaacaaaaa tgtctttaaa  29520
acgtttttat ggtatttatc catgatgctc aaaattaact taccctgctg attgactact  29580
accaagttcc tgtagatcat ggtatatatt ttccttgtag acagaaaaaa aaaaaaataac  29640
aagagatgta catttttagaa taaaaatttg tattaagctg gatctaacca gacttctaca  29700
tacatactta gtatgaacta ctgcacacat tcaaaaccaa atttatcatt ggcaagcttg  29760
taggcactta aaagcacaat aattagtagc acaatgatta tgtacagcta cttttaataa  29820
ttactaaagt ctctctagct gaaagatttc acactaccaa ttcctgaaat gtgctttgtt  29880
tggactttac cagaagaccc ccaaaaaatg agtatgcaag caggaagagg ttgaacatac  29940
ttattttcaa acaggaatgt ttttagctct gtgcttagta gcaaactgcc aaaaaaaagc  30000
attgagttat gcaaaatcca ttaaatacaa actgccaaaa aaactattga gttacgcaaa  30060
atccattaaa taggaatttg attataatct tgactttcat caagcttcaa cttcctttct  30120
tgatcttaaa acgtattaac agaggccggg cgcagtggct cacagacacc tgtaatccca  30180
gcacttcgga aggccgagtc cggcagatca cccgaggcct ggagctcaag accagcctga  30240
ccaacatgga gaaaccccat ctctactaaa aatataaaat tagctgggca tggtggcgca  30300
tgcctgtaat cccagctact caggagactg aggcgggata atcacttaaa cccgggaggc  30360
agaggttgcg gtgagccaag atcacgccat tgcactccag cctgggcaac aagagcaaaa  30420
ctccgactca gggaagaaaa aaaagaaact tattaacaga taaagcagta ctcattcatt  30480
caataaatac agactgaaaa cctaccacgt accagtcact ggtactatgt accagacacg  30540
ggggaaaaca aagaatgaaa cagaaatgta tatgccctca tgaagtttat atcctaacag  30600
gaggataatt catttacccc agtattcgtt gatgtcacaa tggatttttc cttttgtttt  30660
taaactaagg atttaagaga gtgtttgtca caaaatattg tttctcactc aatattaaga  30720
ggaaatatga atcccaacta tctttttca tccttgggaa taaggataca gcaacctaaa  30780
cccacaatat ttttaattca tatccttttc aagtcagtaa tttctcctat ttcttatctc  30840
tcaacattta gaattcaagt ccaaggaaat catacttcca aacattatcc gaagattcaa  30900
tattcagacc aggcacagtg gctcacgtct gtaatcccag cactttggga ggccaagaca  30960
```

-continued

```
ggcagatcac ttgaagtcag gagttcgaga ccagcctggc caacatggca aaaccccatc  31020
tctactaaaa atacaaaaaa ttagctgctc atagtagtgt gcacctgtaa tcccagctac  31080
tcaggaggct gaggcaagag aatcgcttga acccaggagg cagaggttgc agcctgggca  31140
acagagcaag acttcatctc aaaaaaaaaa gaaaaaaaat agaagattca atattcaata  31200
ggtaaagaaa tcaccaatat accaatatag ttatttttaa aatttataaa attaaaccat  31260
atataccaag gccacgtata aaatgacaac atatatggat attaaacaga agtgactcat  31320
caataaaaaa taataattat acatatattt gtaatatata taattatatt atatgtatat  31380
tataatatat aatatacaaa ttataataca aattaagaag ctagatgaaa tttaaatata  31440
gtactatatt cataactagg ttaaaacaca cagttgcaca taatacacaa atgactggta  31500
aaaatacctt ttgttaacaa actacagtcc ttttttttcc tttacttttc ttagttttct  31560
gtcatctcct aatgttcaat aataatatat actatgttta caataataag gttgttttaa  31620
agttataaaa tcccttgctc agctgaggaa gttatgtttt ttaataaaat aaaatcccat  31680
ttaattatca tcttttcagc tatactattg agcattaaat actagcagaa gctagttaat  31740
tgtctcaggt gaacgtattc attccattta ttaatgtaat gaatgctaag gctcaacacg  31800
gattgcctgt gctaaaccaa atgtgacaaa gaattccaaa tgtaggccgg gtgtggttgc  31860
tcacatctgt aatcccagca ctttgggagg ccatggcagg tggattaccg aaggttagga  31920
gctcaagacc agcctggtca acatcgtgaa accctgtctc tactaaaaat acaaaaatta  31980
ggcatggcag caggcacctg taatcccagc tactcgggaa gccgaggcag gagaatcact  32040
tgaacccagg agacggaggt tgcagtgagc caagatcatg ccactgcact ccagcctggg  32100
ccatagagca agactccctc tcaaaacaaa caaacaaaaa aaagaataat tttagaaaaa  32160
tatatattaa aaaaattttt ttttcagatg cagttttgct cgttgcccag gctggagtgc  32220
agtggcgcaa tctcggctca cctcaaccac aacctccacc tgcctggttc aagtgattct  32280
actgcctcag cctcccgagt agctggaatt acaggcatgc accaccacac ccagctaatt  32340
ttgtattttt agtagagaca gggtttctcc atgttggtca ggctggtctc caactcccaa  32400
cctcaggtga tccacccgcc ttggcctctc aaagtgctgg gattacaggt gtgagccacc  32460
gcaccaggcc tatttctaga aatattacct gggttaaatt ctgctggtta agtgccataa  32520
tgataggtga caatgaaaat gatctccaaa ataactaagg ctcaaatgta agcctttacc  32580
acgtggtggt atactgtttc tggaataaaa agttataata gctacagcta atacttgaat  32640
gctttgtatg tgcccaaaac tatgcttttt tatacaacgt ctctcttcaa gagctttaac  32700
ctccacatga agtatttaat tatccctatt tttataaatgg ggaagcaggt ttaaaaaggt  32760
taatttatct agtcacaaaa ctagtaaatg attgggctag gtttcaaaca ctggtttata  32820
agatgccaga gctcaggttc tcaaataata tgccgcagag ctaaaaaatt aagtttcagc  32880
atgtctttaa tatgtttcaa cagtttttct ctgacaaaag tgaatgaggg tagaggtgaa  32940
ctgaaatgtt agcccagatg gctttttaca atggactaaa ctgaagaatt acctgtgctc  33000
tttcacagag aagcttggca cgccaaacaa atctcctaga agatcatttg aacaatatac  33060
aatatgttgt tgcttctcat catataatcg tttagtcata atatactggc caagataaaa  33120
aagaacctga aatacaaata tgatttctga gcattaaaga aaactaaatg ttagttgtaa  33180
atacatttaa taatatccta tttatctgaa taggggtaaa caaccaggaa ccatatccac  33240
aactatgtag aacaaccatt ttgtacttag aagctacttt tggctgggcg cagtggctca  33300
```

-continued

```
cacctgtaat cccagtactt cgggaggccg aagcggatgg atcacgaggt caggagataa  33360
agaccatcct ggtcccatct ctactaaaaa tacaaaagtt agccaggcat ggtggcagac  33420
acctgtaatc ccagctatta gggaggctga ggcaggagaa ttgcttgaac ccaggaggtg  33480
gaggctgcag tgagccgaga ttgcgccact gcactccggc ttaagcaaca gagtgagact  33540
tcatctcaaa aaaaaaaaaa aaaaaaaaaa aaaaagctac ttttaagcct tttccattta  33600
atttgacaga agcagaaata actgcttctc tatttactta agcaaacctt aaaatgtgag  33660
gtttttttcc ttgtagactt taactctgcc cagatactta gatactaaca tattaggaag  33720
ggaaaaggca gcaaaataaa aaactgatag ccaaaaaagt tgcagaaaca aaaatcaact  33780
aaaatatggc agtggtctgg agccacttag taaatagtca taaatactat aaacctcaat  33840
agcctctgag gtcaccagag gaggaagaca gaaaaacaat caatcaatga cagctacaaa  33900
acagtttgag agaattctga gaatgaaata aaccctctaa ggtatcaatt tactccatat  33960
tatgataaat aatcaaaata atgactttga accattaata aaagttaaat tatattccct  34020
gtgctgcatt aagacaagaa gttggcaata catttttaag atatccagat ataaacctat  34080
taacaactac ctaaatacat atggcatttt acagtttaca atgtactttt ataagtatta  34140
tctcattctg atatttcata agattattat cactgtatta gaaatgaaga aattgcgttg  34200
ggcacagtgg ctcacacctg taaatctagc actttaggag gccgaggtaa gcagatccct  34260
tgagcccagg agttccagac cagcctgggc aacatagtga aactccatct ctacaaaaaa  34320
atacaaaaat tagccaggca tagtggtaca agcctgtagt cctagctact gcagacactg  34380
aggtgggagg atcacctgag cccacgaggt ccaggctgca gcgagcagtg atcatgccac  34440
tgcactccag cctgggcaag agagtgagaa actgtcacat aaaaaaaaaa aaaaaaaaaa  34500
aaaagaagaa gaaactggcc ccagctcttc tgactcttaa tccaacgctc tttttactac  34560
ccatactagc tttcactacc ttcctgtgtg ccccagaaca aagatcctat aactgagaac  34620
tatatcagac aatacataca ctactgttac atagtttagc ataagcattc taagtcttta  34680
tgatggcctt ggccaatttt ctcatttcta tctactgcta aatccatact tttttgtttc  34740
cttaactgat tatccaatga taataaggtc aatcccaaat tagccttaaa aataccattt  34800
aacctggccc tttcctacaa acactgtctt tggatttaac tggctaagca ggcatcggcc  34860
ttaaaggaat attcttatgt gactgtggat tggacagatt gctgtccagc agtgggaaag  34920
gaaaaaggaa gagaacttag atttattcta ccaaacatcc tttaaggaag tttctaaaag  34980
tatagctgga gaggaaaaag aaaaatggaa gctcttcctg ccccactata ccgttgtaag  35040
aaagaaactt aaatgtttta agtaatctga gtcccataaa ctaagtggga gagacagaga  35100
acaggcatat ttcaatcaca ctgaaattct gcctaaggtt gctcaatctg tcactgaaaa  35160
tcatgcttct gtgcacaaat ttaaaggtgg ggaatgcatt aaaatgctgg aaccattaga  35220
tagaatatat ggtcatgaat cagctcacct ctatcccaga aagatcagta tactgtactc  35280
atgtatctct agtgcagaag ttcttaacct gggatccagg gatgcccaag aagtccttgg  35340
atagaattca gggggtccat taatttggat gggaaaaaaa aaattctatt cttattttca  35400
caaacttcta actagaattt agcttttcct tcgattataa atgtaggcaa caaatcacaa  35460
cagtattaat acctgtgatt tcatcaccaa caaaaatcag aggtgttttc ctatcatact  35520
gtacttatgg caaacatttc aaaatatgac ttatattcct cactatatca agataatatt  35580
tattggccag gcatggtggc tcatgcctat aatcccagca ttttgggagg ccaaggcaag  35640
tggatcacct gagactagga gttcaagacc agcctggcca acatggagaa accccatctc  35700
```

-continued

```
tactaaaaag acaaaaaatt agccaggcgt ggtggcaggt gcctataatc ccagctactt  35760
ggaagggtaa ggcagaagaa gggcttgaat ctaggaggcg gaggttgcag tgagctgaga  35820
tcgtgccact gcactccagc ttgggtgaca gagcgagact tcgtctcaaa aaacaaaaaa  35880
acattatatt tattatatct tcttctaaat cttagtattt attatgttaa taacaaaagc  35940
acacatatca caaactagtt tactattttg gtaaccgtat tttagtatgt ttcctttgta  36000
attctataca ttttatttca tacatttaaa aacatgattc tgggaaggag tctaccaaag  36060
ggttgacagc ataaaatggt caagcaccct tacggggctt ccatttatct gagttcctag  36120
ctgagaaatg aaactcgagt ataattagaa ttttcagctt taaaatatag tccaaacgac  36180
cacaaaatta aatgttgctg cttaatgaaa aatccttcta tatggccaat ttctccacat  36240
ggtcttgaaa actttaagta tggctacatg taactagtga gatactactt atctcttgat  36300
tcagcttacc tctttcatag tataagtgtc tttttgtgca ccaacagact ttaataactt  36360
caaaagcaat ggctttggtc taacctataa agagaaaaga actgctatta tacttccaaa  36420
attatcccag aactataggc cctgcagcaa acatatccat caagttcaat aaaggggatt  36480
tggaaaaaat gctggggagg atctaatcat tatgcaagta tcatggaatc atcaagtatc  36540
agttgtgatc acagacagta tccaatccaa aagagcaaag attacttttt ccttcagcta  36600
tttatattac ctgcttactg ccttacaaac aaccataaat tactgagatc caatgagctt  36660
accgtactga tccaacgagc ttattgcaag ctaacttaga gaatcaaaga gaaatgaata  36720
aatctttaga gtgggtcctg ttatcaatct tctctttcta aagattaggt tcctgaaggc  36780
tagagaacct aactaactaa cccaagctga caagggtaat taagaacaga tcagagataa  36840
caacccaggt ccctcaacta caactcagca ttttcttcct actatatcat gctgcctctt  36900
agttagtcta catttcaaat atctacttga caaacattta ttgagcttct actatgcact  36960
ggacagtggt aggtactgca aaagaaatta caaataagac atatgacctg tatgcaagga  37020
gcctgccaac tagattaggg gtcaattttt ttctgtaaag agccagactg taagtatttt  37080
aagcttttca tacaaatggt tctatccaag taaaaagcat ggctactatg taaaccaacg  37140
ggcatggttg cattccagta aaattttcct tacagaaaga aaggcagctg gctgggagag  37200
gtggctcttg cctataaccc cagcactttg ggagacagtg ctagaggttt gcttgaggct  37260
aggtgttcaa gaccagcctg ggccacactg agagactcca cctctacaaa aaaaatttaa  37320
aaactaaaac aaaaacaggt aacaggccaa agttggctga caggctaaca tttgcctgcc  37380
ccttatctag aggttttaca aatggtcttg agaaaaataa ttgtcatggg ggaggggaat  37440
gtaatatact atgcactttc tcccttcctt ttggtttatc aaaatctgca aaactcaagt  37500
atctttacag cttgccacta ccacacaaac tggtacctct gcacctctct ttaatatgcc  37560
ccggtcctct gtctaacttt aaaatctgac agcaccccca ttggggatgc cttaaaaaca  37620
gatttttaaa aattgcctat ttccagctaa tcaataaaac aaatattatt taacaattga  37680
aaaatttaaa atacatatag aattgaatta ttaatttttc tgatcacttt tttttttttt  37740
aactgtgctt acatatgcac tttactttca ggctaaagaa tggactctct caaaaaagat  37800
ttaaaaataa cctttttttct cctgaatttt tattatatgc tatattagct tcaaattaga  37860
taaaataatt caaagtaaaa atctgtaatg gaagccaggt gcagtggctc aggtctgtaa  37920
tcccagcact ttgggaggcc gaggcaggca gatcacctga ggtcaggagt gtgagaccag  37980
cctggccaac acagtgaaac tccgtctcta ttaaatatac aaaaattacc caggtgtggg  38040
```

-continued

```
ccaggcgcag tggctcatgc ctttaatccc agcactttgg gaggccaaga caggcagatc  38100
aggaggtcag aagttcaaga ccagcctgga caacatggtg aaaccctatc tctactaaaa  38160
gtacaaaaat tatccgggtg tggaggtggg tgcctgtaat cccagctact cgggaggctg  38220
cggcagaatt gcttgaaccc aggaagcaga ggttgcagtg agccgagatc atgccactgc  38280
actccagcct gggcaacaga ccaagactca gtctcaaaaa aaaaaaaaaa aaaaaatctg  38340
taatggaaag ccatcagtat attagtgact taaaagacat gtattaatga gaaaacagct  38400
ataaaagata atagcatttg taatcttaca ttgaagaaca agaaggtaaa ttacaggtga  38460
agatctaaat atttaaaaaa tttaaatcta gaagaaaata taggaatata tttgcaagat  38520
cttgggacag gagagttctt ccaaagcatg atatgaaatt caaaagccaa caaattttac  38580
ttcacagaat tgttctcaat ggggaaaaga caacataaaa ttaaatgcta cattagtaaa  38640
caacaaaagt taaatatact tgaaacacat agagctactc caattactaa gaaaaatttt  38700
aaaaaactaa aaggaaaatg gacagataag actaggcaag tcccagaaga aataaatgac  38760
ttaacaaaat ggaggcctgg tgcagtgatt cacgcctgta atcccagcac tttgggaggc  38820
cgaggcaggc agatcacctg aagttgggag ttcaagacca gcctgaccaa catggaaaaa  38880
ccccatctct actaaaaata caaaattagc tgagcgtggt ggcgcatgcc tgtaatccca  38940
gctactccag aggctgaggc aagagaatcg cttgaacccg tgaggcagag gttgcaatga  39000
gacaagatct cgccattgca ctccagcctg ggcaacagga gtgaaactct gtctcaaaaa  39060
aaacaaaaac aaaaacaaaa aggaaaggtg cccagcctca ccaagaaact agagaaaaat  39120
gaatttaaac aatggtacag taccttttat caaaaaaata gtaataataa taaaagaggc  39180
caggcgcagt gactcacgcc tgtaatccca gcactttggg aggccgaggc gggcggatca  39240
ccaggtcagg ggatcaagat catcctggct aacatggtga aaccccgtct ctactaaaaa  39300
tacaaaaaat tagccgggcg tggtggtggg cgcctgtagt cccagctact cgggaggctg  39360
aggcagggga atggcgtgaa cccggggaac ggagattgca gtgagccgag attgtgccac  39420
tgcactccag cctgggagac agagcaagac tccgcctcaa aaaaaataat aataataata  39480
attaaagatt ggtgatattc agtattggca ggagtgaaac tgttagagcc ttttggtgag  39540
caagttacca gtagcaatca aatagtaaaa ttgagaactc aggagttcta attctctaaa  39600
atctttttct tttctttttt tttttttag acggagtttc gctcttatcg cccaggctgg  39660
agtgaaatgg cgcaatcttg gctcaccgca acctctgcct cctgggttca agcgattctc  39720
ctgccccagc ctcctcagca ggggattata ggcgcgcgcc accatgcccg actaattttt  39780
gtatttttag tagagacagg ttttcaccat gttggccagg ctagtcttga actcctcatc  39840
tcaggtgatc ggtccgcctt ggcctcccaa agtgatggga ttacaggggt gagccaccga  39900
ggccagccta taattctata aaatctttct tacagaaata gtcacacggg atgcatgtac  39960
aaagcggcac tatctgtaat actcaaaaac aggaggcaat ttttaaaaac ctatcagtaa  40020
aggcataaat aatttttaaa atggtatact catgctgtgg aatactatgc agccattaaa  40080
aagaattctg tagactttat ttattgacaa ggatgcaagt cacagaacaa ctacagtttc  40140
atcttgttag tacaacaaac aggacaataa catagattta aattcaaatg taaatatatg  40200
tgggtacgca cacaaaaaat ctaaaaggaa acatggagca aaaagcctgg aattttcagg  40260
ttttacttta aaatttctct aatgacaaaa atctttaaaa caagcacgaa taacttttt  40320
gacttttaga aaccattttt aaaaattaaa tactgggagg tcaaaaagga aaaaaaaatc  40380
agtcacgtaa caaacgtaac ttcaaccacg cttaacaatg taatggaact aatttttaaa  40440
```

-continued

```
gcaaatgtgg caaatggcta aaaaaatact gaccagttct taacagtttt taactccacg  40500
cagttacgcc agaggtagca cactttaagc tatgcacata caattttatt tacagagcca  40560
tgctacaatt gaggtatacg aaatttagtt tatcacttca taaaataaat tattcttaaa  40620
agttacacga gacaaaaata ctaaccaggg tctcttgttc cgaagctgga atctgtgagg  40680
tggttacagc accatcagta ggtacagaca tgttggtatt gcacatttgc ctacaaggaa  40740
aaaaaagaca cgatgaaaac tggaaatcat gaaacatctg tggaaaatac atcatatata  40800
aagaacataa acaacagtta aaactaaagc tacaagcaag tcggtgctta cctggatcag  40860
cagagaaaaa gtggcgtgcg tccgtgccca caggtctacc ctccaatcgc cactgaacac  40920
agctgggaaa atgcatggtt taaatagccc cagctggaga caagtcagga cttaactcct  40980
tttactgcag tttcggaacg tgtctgaact tgaccagctc aagaggaaaa gctgagtcaa  41040
cctgcccact gaaccggccc aatcccgccc agactacgcg cagcgttcac actagtgacc  41100
cgacaggcac ctgcgatcat ccggacctcc cgcgccgaag cggccccgca gcccccggcc  41160
cccgtgacct ttaccctgaa ctcccgcgga gacctccgaa ccacccccac ccccaccgcc  41220
gcgagagccg tccgaaatcc cgccctcctc cctggcggcg actgcctagc cccagtccaa  41280
caaaacctcc gcaaagccac gtgccccatg ccccgcgccc cgcgccccga gcccccagcc  41340
acgaaccgca caaaggctgc gaacgggcag aggctgggaa ccagcgatag aggggacacc  41400
gtcagagccc agacccaaaa gtgaccgctc gctgccgggc cagtacctgc tcctcaccat  41460
ccggggtttt cgcgcttgga gtcgggggtc cctcaagact ccccagtttc cttcacgggg  41520
cgcgcggaag cacgacgccc tggcctcgg ggatcattcc actctccggg ccagggcact  41580
gggcgctcgt acgcactaat ccggggaggg acggtgctcc tggctgcgaa agcagcagga  41640
tctcggtcag aggggtcgcg gccgcccctc gggctcggct tcttgctcca tctttccgac  41700
acacagggcc acacaggccc cagaagcagc caagctcgcc gcggtgcctc ggtgcgcgcc  41760
ccctaccgcc cgaggggagc gcgcgggtcg tcgcggcgca tccgggcatt tgtgcgcgcg  41820
cacacaaccg gccccgcttc cgccaattgg gtccggggct cggccgcacc acctccggga  41880
tgatggagtg gggggtgtcg ccccgcgggc gcggcgggct gtgaggcggg gtgggggtgt  41940
tggccgcgag ctgagagggt ggggctcggc ctggcgcgga gccagcaagg tttggcgctg  42000
tgacactcct ttagccgttg cgctatgttt gtatttcttg tgtttacact tcccgcccgc  42060
ggtggaaact gcgacaaatg cggatctccg tgtcgctgtt accaaaaaga aaccaaaatt  42120
aacagctgtt taatatatta agcccactcc accagccgct ggagttgtac ccaaatgagt  42180
tattttaagg cctgttttta aaaaagatta aaaatagcac ttaaggcagg cttatacacc  42240
ggtgcataca gctgttctgg ttggagaacg aagatgctgg ttaccgttgg cggggagggg  42300
agcggttact ctgcgctttt agaatgtttg ggtttggctg ggcgcggtgg ctcacgcttg  42360
taatcccatc actttgggta ggccgaggcg ggtggatcac ttgaggtcag gagttcaaga  42420
ccaacctggc caacatggga aacgccgtct ctactaaaaa ctacaaaaat tagtcgggcg  42480
tggtggcggt cacctgtaat cccagctact ctactccgga ggctgaggca ggacaatcct  42540
gtgaacccgg gaggcagagg ctgcagtgag ccaagatcat gccattgcac tccagcctgg  42600
gcgacagggc aagactctca aaaaaacaaa aacaaagttt gggtttgtta atctacacat  42660
tcattatcat taaaatatat acttatatat tatgcactca ttctgactca cctactttcc  42720
cacagagatg tggcaaaaac gtttttgatg cggtctcata aattgaggac ataaagaatt  42780
```

-continued

```
gagttagcta aacccaaaaa cacagccatt gcaaagaagg aacacgtttc ttctctggcc  42840
agtaagtgat tagctccttg tgaacaagga cctttttta taaagttata tccttccctt  42900
ctgcagcttt ttttttttta taaagttata tccttccctt ctcccgcttc ccagcctacc  42960
agaaaggaaa cttccttaaa catagtggtc actcagttga tttaagttga ttgccaatat  43020
tattaactta agagatttaa tatgtggctt ttaaaaagat aatctcatct tcatcagatc  43080
atatacagtg ggtttctaa tagactcagt gcttgaccct ggatgaaaga aaatctcaag  43140
cagtgagaaa atgtaagcat gaaaagataa gtgataggct gcgcacggtg gctcacgctt  43200
gtaatcccag cactttggga ggctgaggtg ggtggatcac gaggttagga gttcgagacc  43260
agcctggcca agatggtgaa accttgtctc tactaaaaat acaaaaatta gccgggcccc  43320
gtggcgggcg cctgtaatcc tagccacttg ggaggctgag gcagaagaat cgcttgatct  43380
cgggaggcag aggttgcagt gagcggagat cgcgccactg cagtccagcc tgggtgacag  43440
agcaagactc catctcagaa gaaaaaaaaa aaaaaagaga taagtgatag aggttgatat  43500
ttgttaaata tcaagtgaac gaatgggttt gtgctataaa agttcagaga cagaattaat  43560
tgcttagtaa atgctggagg cagttcacaa aggcctcaga gatcacacat attttgtgtc  43620
ttgaaagatg gtgagactta aataaaagca gagaatattc caggcacaag aaaattatca  43680
aaaaatacag aaaggaaaat ataagaggac tgtttgagat acaataaata aatccgtttg  43740
acttgcatga aagtcaagaa gaagttttaa gaacttggag tctccttaaa tgccaagcaa  43800
ggaaatttgg gctttcgaca gagtagacat tagaagcata aaaacaagtg atttgcttca  43860
aactgtattt taacaggacc accaagagta gattcaaact cagaatagtc gggccggctg  43920
ccttctggac cgactttccc ccttctcatt ggccttgtgc tttgaaaaaa ttatcttgac  43980
aaaattatta gagcagaaaa aaaaaggcag aactgataag attagtcctt ttctaatgga  44040
accagaaaag aagggtcaga aatgaaggca gaagggagaa gcgggggtgg gggagagaga  44100
gagaagtaaa aaggattcac tcaagaacct ggtattcaaa actacgtgta ccagcactac  44160
cacagcagta tgactcagtg tccacctaaa gcatgatgat actgcttacc aaaaaaagtc  44220
tggagggaat gaaaagttgg gttagtttta agttatgggt cacagaacag aattcggtgg  44280
taaaaagctt aggctgggaa cagagcttga aacagcaaag gaatgagagg aacgaccaaa  44340
aagccaagga ccatatagtg atgtctgaaa aatcagaatc aggtaataat attgaatact  44400
gcaaaagtca gagaaaatgt ggaaataaga aagcaagcga tctggaaagt ggcgagtaag  44460
atggaatatg aggaggttgc tgagagctgg gaggagacgg cagacagcgg ggaaatagac  44520
gtctggaaaa aaaactgaag atcacacaga aagcaggaaa ttcaaatctc ccaaagtgcc  44580
cattgtgatt caggatgata attttccccc gggacccccct ccacaggtcc gcatcctcaa  44640
gaggcccacc agcaacggtg tggtcagcag ccccaagtcc gctagcaggc ccgcccttcc  44700
agtcaagtcc ctggcacagt gggaagccga gtacaccgag gccaggaagc ggatcctggg  44760
cagcgccaac ccgaggagaa gcaggagaaa cccatcctcg ataggtcttc ctctgatctt  44820
cttcccttca ggccaaccag gatctcctaa cccgaagaca gcagacagcc caataatgtg  44880
atcagacagc ctctgggtcc tgatgggtca cacggcttca aacagcgcag ataaatgcag  44940
gcaagaagag atggcgcgac tgccgcgtca acgcgtcctg ggtcgtccgc caagggttgc  45000
actaccgtgg cagacagctg gacttgagca gcgggaactt gacttacttg cctggtgatc  45060
cccgttgctc cgcccactgt gaccttgaat cccatgcact gtgacctccc cccttctcct  45120
ccttcccact gtgattggca ctttgacaag gactgtccca agtcaatgga aagggaaaaa  45180
```

-continued

```
gggtgagggt taggagaagg ttggggggaa cccaccaatt actcagagta gagagtcaga  45240
cagggccagc aatagcggtt tatcatgctc attaatttgg gatttcaaaa cacaaatgaa  45300
ctcacaccta cccacccccca agtgcatgtc atcacttaaa aagtgagttc catttgaaaa  45360
aaaagaaagc aaactacctg ctcactctaa aagcagttgc tgttgtttgt gactttgcca  45420
tttaaaaaaa tacagaccag ctgctgctgt ttgcttgcat tccacagtta tcttgtgtca  45480
ctttgccctt tgttgtgctt acttgaagtt tctctagagg caaactgctt atttctagta  45540
gcgttgttct tgatgcccaa gaggtgttcc aagaggttga gatactttga gtgtctttat  45600
attctctggg acctaaactc tgcaaacaag gctcacacct gtaatcccag cactgtggga  45660
ggccaaggct ggaggatcta ttgaggccaa gagtttgaga ccagcctgag caacatggcg  45720
aaaccctgtc tctataaatt gcaaaaaaaa attagccagg cgtggtggca ctcacctata  45780
gtcctagcta cttgggagcc agagctggga ggatggcttg agcccggata ggttgtggtg  45840
tgatcctgcc actgcactcc agcctatgtg acagagtgag accatgtctc aaggggaaaa  45900
aaaaaagtct acaacagact tatcttgacc caagggccac ttcgtacttg tatttattag  45960
tcataactaa tcttttgtct ttcttttttt ttttttttg agacggagtc tcactctgtc  46020
acccaggttg gagtgcagtg gcacgatctc agctcattgc agcctccacc tcctgggttc  46080
aagtgattct cctgcctcag cctcccgagt agctgggatt acaagcttgt gccaccatac  46140
ccggctaatt tttgtatttt tagtagagac gggatttcac tatgttggcc aggctggtct  46200
cgaactcctg gcctcaggtg atccacccgt ctcaccctcc caaaatgctg ggattacagg  46260
cgtgagccac tgtgcctggc cacaactaat ctttaaagca tggtgaaaac taaacaagat  46320
ttagctcaga aaccgtgttt agaatgctga gtttcacaat atttatgaga ccatctaaaa  46380
ttacagaagt agttcaaatt ccttatgtct ttccaaacat ctggaactga atagtgttat  46440
ttaaaaggca aaatccgggc cggacgcagt ggctcacgcc tgtaatccca gtactttggg  46500
aggccaagac aggcagatca ctgaaggtca ggagtttgag accagcatgt aaaaccccgt  46560
ccctgctaaa aatacaaaaa ttaggcgggc atggtggtgc aagcctgtaa tctcagctgc  46620
tcgggaggct gaggcagcag aatctcttga acctgggagg cagatgttgc agtgagccga  46680
gatcgcgcca ctgcactcga gcctgggcgg cagagcaaga ctctgtcctg gaaaataaaa  46740
aagtaaaaaa taggccgggc atggtggctc atgcctgtaa tcccaccact ttggcagggt  46800
gaggcgagtg gatcacctga ggccaggagt tcgagaccag cctggccagc atggtgaaac  46860
cctgtctcta ctaaaaatac aaaaaattag ccgggtatgg tggtgcacgc ctgtaatccc  46920
agctactcca gaggctgagg caggagaatt gcttaaacct gggaggcaga gatcatgcca  46980
ctgcgctcca gcctgggaga cagagtgaga gtgagactcc atctcaaaaa ataaataaat  47040
aaataaagta aaaaataaaa agcaaaatcc cagcaagtag tgaatacaaa gactttttgt  47100
ttttactttg aaaattaatc aactttttgt ttgactgaaa catacagaaa cattcacaga  47160
acaattaata ttcaacaaaa gaaaccaccg cctcaagttc ttctgctctg aagaacaaaa  47220
aaagaaaaaa agaaaccact acccagaatt cacatttgtc attcctgcat caaacatatt  47280
ttttttatta tttatttatt tatttttgaa acagagtctt gctctgtcgc ccacactgag  47340
tgcagtgagc caagattgta ccactatgcc tggctaatct ttagtatttt tagtagagat  47400
ggggttttac catgttggcc aggctggtct caaactcccg acctcaagca atccacctgc  47460
cttggcctcc caaaatgcta ggattacagg tgtgagccac tgagcctggc ctaaataaat  47520
```

-continued

```
ttttttaatg aaacattgct taaaaaatta aaatttcact gttattcttt atcccattcc  47580
cctcccttct cttgataatg atcaatttga tgcctgtcca ctaagtctgt gttttataca  47640
ttcactgtaa atttatgaat ccataaacaa cacggacagt aggctgcata cctataagag  47700
gacttgctgg gcaacagaat agtaaacctt agagtaagtt tcaatatgta acaggaaaag  47760
ctctctttat ctttttcagt attgttttgg ctcttcctgg atgttaactt ttagaaccag  47820
tttgtctaat tcacaaaaag aatcctcttg ggattttgct tttcattgca ttggattgtt  47880
agactaattt gacttatttt cagtatgaat tcttcccaga taagaacatg atatatcact  47940
ccatttttag gtctctctta acatccttta ataatgcttt attgtttcct ccttaaagct  48000
gttgtatgtt tggctggctt ttttctgaag tgctttataa gttttattgc tgtttttaaa  48060
ttacaccttt taaaattttc ttttcttttt ttttgagatg gagtttcgct ctgtcaccca  48120
ggctggagtg cagtggtgcg atcttggctc actgtaagct ccgcctcccg ggttcatgcc  48180
attctcctgc ctcagcctcc ggagtagctg ggactacagg cgcctgccac cacgcccggc  48240
tatttttttt ttgtattttt agtagagaca aggtttcacc gtgttagcca ggatggtctc  48300
gatcttctga cctcgtgatc cgcccacctc ggcctcccaa agtgctggga ttacaggcgt  48360
gagccaccat gcccagccgt aacattttat tttctatttg gttattgcta acatatgaaa  48420
caattactca tttttgtgtt ttgatcttat agccagccag caatactgct tttttgttct  48480
ttctgttttt gtttttttgtt ttttgggttt tttttgagac ggagtctcac tctgtcaccc  48540
agacgggagt gcagtggcac aatctcggct cactgcagtg tctgcctccc tggttcaaag  48600
gattcttctg ccttagcctc ctgagtatct ggcactacag gtgcgtgcca ccacacctgg  48660
ctaattttta tatttttact agagatgggg tttcgccatc ttggccaggc tggtctcgaa  48720
ctcctgacct cgtgatccac ccaccttggc ctcccaaagt gctgggatta caggctgtat  48780
tttgttttgt tatacagtac tattagtttt tcagtagatg ctcttggatt ttctatgtta  48840
ataatatcat atgcaaaaat cactaacttg tctcttcctt aaacctcttt ttcattttct  48900
tacaaccatt ggaatggaat agtagcaatg atagtgggca tcctcatctt attcatgaca  48960
ttagtaaaaa tgcttttaaa atgtgatgtt tgctgtaaat tttaggtaga tgctctttat  49020
tacataaaag tttccttcta ttcctggttt tttgagctta taaaaaagta tgaatcagtg  49080
ttcagtttta tacactgctt ttttatgcac ctagaaatga ccctgtggct tttctccttt  49140
aatctgtcta tgtggtgaga ttatattgat agatttccaa tattgacctt ccttgtttta  49200
ctcagataaa attctactta gttacaatag atctcttttt ttggacattt atgaactgaa  49260
tttttaagag gaaaaatatt acacaatgat atgggagcat aattgagttc ctgctcttag  49320
aagataacaa atatttcaga gattttagta ggaatattgc cctgttaaga acgctcaatt  49380
ctctaaagct aagttcaaat aaggcccaat tcttggcctg agactctggt tcccacaagg  49440
gcaatacagg ctgaactggt ttgataactt ttaccattga gagttttttt tttctttttg  49500
agacggagtt ttgctcttat tgcccaggct ggagtgcaat ggcttgatct cggctcagtg  49560
caacctccgc ctcccagata caagtgattc tcctgtctca gcctccgaag tagctcagat  49620
tacaggcatg tgccaccaca cccagctaat tttttgtatt tagtagagac atgtttcatc  49680
atgttagtca ggctggtcgt gaactcctga cctcaggtga tccacccgcc tcagcctccc  49740
aaagtgctgg gattataggc gtgcgccact gcacccggcc acgtttaaga gttttaagga  49800
aggaccagga ataatagagg tcatcttttc gtggaacgaa gagtttataa tctcccagct  49860
gacctaaatc tgagatctgt gatcgtatct agtctgaaag ttacagagcc attcagctgg  49920
```

-continued

```
cagaagaaag gtagtgaagt tgaacagcat ccccactctt tggggtggaa aggttgctgg  49980

agtttccccc agattaagtg gttcctggag aagatggaag gagtataagc agttctgctg  50040

gtaactccta aaatggccac tacctgggta atagaaccct ggaagcaaaa gacatagaat  50100

atctattggt agaatgtgct ggactaggga gaaagaagtt gagcttcatt catatacccc  50160

tgctcaactt cctaccagga ccatgccacg agtctttctg gagaaatatc atttggacac  50220

ctgccagatg aagagaactg gtggtcaatt ggtaataatc agagaaactg ggacaaccaa  50280

cagaaaggga cagaaatgtt tcccatgatc tagttgaggt tgttcataca atgaaccaca  50340

gttatgtcct gctaataaaa gggcaactaa ttttgaaggg caattatgta aagaaatgta  50400

attttcctct ccttcctcct tgccacccca actggtatcg ggatggcagg agtcatgtgt  50460

ggttttctat ggctgtgtaa caaattacca taaatgtagt agcttaaagc aacacaaatt  50520

attagctcac agtccatata tcagaaatcc aggtaggctc acctggttcc tctgctccag  50580

gtgtcataaa gcctaaatca aggtgtgggc cagcttgggc tcttaaggat ctagggaaga  50640

acctgctttc tagcttattc aaattgtcag ccaaattcag ttccttgtgg ttgtaggacg  50700

gtagtcccct ttttcttgct agcagtgagg accactctca gctcctgaag gcttcctgca  50760

ttccttgcta cacactcccc tccatcttca agccagcaac agggtgttga atcacccttg  50820

tgctttgaac ctgacttact ctcctgctat cagccagaaa aaaactctga cttcaaaggc  50880

tcatgtgatt tgatgaggcc aacccagatc atctcccttt tgccatgtaa tgtaacagaa  50940

tgatgggagt aatatctcct catattcaca ggttcctccc acgcttaaag gggaggggat  51000

catccatagg caaggtcact gggagtcatt cttggaatt                         51039
```

ISOLATED GENOMIC POLYNUCLEOTIDE FRAGMENTS FROM CHROMOSOME 12 THAT ENCODE HUMAN CARBOXYPEPTIDASE M AND THE HUMAN MOUSE DOUBLE MINUTE 2 HOMOLOG

FIELD OF THE INVENTION

The invention is directed to isolated genomic polynucleotide fragments from the human chromosome 12q13-q15 region that particularly encode human carboxypeptidase M and human mouse double minute 2 homolog, vectors and hosts containing these fragments and fragments hybridizing to noncoding regions as well as their reverse complements t. The invention is further directed to methods of using these fragments to obtain human carboxypeptidase M and human mouse double minute 2 homolog and to diagnose, treat, prevent and/or ameliorate a pathological disorder.

BACKGROUND OF THE INVENTION

Chromosome 12q13-q15 contains genes encoding, for example, interleukin 22, a protein tyrosine phosphatase, interferon-gamma, carboxypeptidase M and the human mouse double minute 2 homolog; the last two of which are discussed in more detail below. The chromosome 12q13-q15 region is known to be aberrant in tumors such as sarcomas (Oliner et al., Nature 358: 80-3, 1992).

Human Carboxypeptidase M

Human carboxypeptidase M is a cell membrane-bound basic carboxypeptidase believed to act by activating, inactivating and modulating excitatory peptides such as the anaphylatoxins and kinins (Tan et al., J. Biol. Chem. 264: 13165-70. 1989). Its expression is increased as monocytes differentiate into macrophages (Rehli et al., J. Biol. Chem. 270: 15644-9, 1995). It is also widely distributed as an ectoenzyme of specialized epithelia and endothelia. Its ability to convert anaphylatoxins to their less active C-terminal des-Arg forms protects against complement-linked tissue damage.

Human Mouse Double Minute 2 Homolog

Human mouse double minute 2 homolog plays a key role in modulating actions of p53 (Oliner et al., supra), in part by targeting p53 for destruction (Ries et al., Cell 103: 321-30, 2000). Over-expression of this oncogene increases tumorigenic potential. The human mouse double minute 2 homolog is over-expressed in both sarcomas and some leukemias. In addition to its ability to in effect neutralize p53, it reacts also with a retinoblastoma protein.

SUMMARY OF THE INVENTION

The invention is directed to isolated genomic polynucleotides, said polynucleotides obtainable from the human chromosome 12q13-q15 region having a nucleotide sequence at least 95% identical to a sequence selected from the group consisting of:

(a) a genomic polynucleotide encoding a polypeptide selected from the group consisting of human carboxypeptidase M depicted in SEQ ID NO:1 or human mouse double minute 2 homolog depicted in SEQ ID NO:2, or variants of SEQ ID NOS:1 or 2;

(b) a genomic polynucleotide selected from the group consisting of SEQ ID NO:3 which encodes human carboxypeptidase M depicted in SEQ ID NO:1 and SEQ ID NO:4 which encodes human mouse double minute 2 homolog depicted in SEQ ID NO:2, or variants of SEQ ID NOS: 3 or 4, (c) a polynucleotide which hybridizes to any one of the polynucleotides specified in (a)-(b) and (d) a polynucleotide that is a reverse complement to the polynucleotides specified in (a) to (c)

as well as nucleic acid constructs, expression vectors and host cells containing these polynucleotide sequences.

The invention further relates to a polynucleotide comprising:

(a) a genomic double stranded polynucleotide set forth in SEQ ID NO:3 encoding human carboxypeptidase M set forth in SEQ ID NO:1 and the polynucleotide set forth in SEQ ID NO:4 encoding human mouse double minute 2 homolog set forth in SEQ ID NO:2;

(b) a polynucleotide that hybridizes to one strand of the polynucleotide of (a) and (c) a reverse complement of (a) and (b).

as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (a) with an adjuvant and (c) obtaining antibody from said immunized host animal.

The invention is further directed to a nucleic acid molecule or reverse complement thereof comprising a sequence of nucleotides which specifically hybridizes to noncoding regions of said polynucleotide sequences of SEQ ID NO:3 (human carboxypeptidase M gene) or SEQ ID NO:4 (human mouse double minute 2 homolog gene). These sequences may be used to modulate levels of human carboxypeptidase M and human mouse double minute 2 homolog in a subject in need thereof and specifically for the manufacture of a medicament for prevention, treatment or amelioration of a medical condition. As defined herein, a “polynucleotide fragment” may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, a “reverse complement” is a molecule encoding a sequence complementary to at least a portion of an RNA molecule or to a genomic DNA segment and may be used interchangeably with "antisense oligonucleotide". The sequence is sufficiently complementary to be able to hybridize with the RNA or DNA, preferably under moderate or high stringency conditions to form a stable duplex or triplex. A "reverse complement" also includes peptide nucleic acid reverse complement sequences.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising (a) isolating genomic DNA from said subject;

(b) detecting the presence or absence of a variant in said genomic DNA using a probe or primer derived from a polynucleotide hybridizing to non-coding region(s) of a human carboxypeptidase M gene and human mouse double minute 2 homolog gene; and (c) diagnosing a pathological condition or susceptibility to a pathological condition based on the presence or absence of said variant.

Probes or primers derived from SEQ ID NO:3 (human carboxypeptidase M gene) or SEQ ID NO: 4 (human mouse double minute 2 homolog gene) may be used to identify variants including but not limited to mutations, duplications, translocations, polysomies and mosaicism on the human carboxypeptidase M gene or on the human mouse double minute 2 homolog. Therefore, the invention is also directed to a method for identifying variants of SEQ ID NO:3 and 4 comprising (a) isolating genomic DNA from a subject and (b) determining the presence or absence of a variant in said genomic DNA using the probes or primers.

DETAILED DESCRIPTION OF THE INVENTION

The invention is directed to isolated genomic polynucleotide fragments that encode human carboxypeptidase M and human mouse double minute 2 homolog, which in a specific embodiment are the human carboxypeptidase M and human mouse double minute 2 homolog genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The genes encoding human carboxypeptidase M and the human mouse double minute 2 homolog are disposed in the chromosome 12 genomic clone of accession number AC025423, 150579 base pairs, at, respectively, nucleotides 1-99860 and 99541-150579.

The polynucleotides of the invention have at least a 95% identity and may have a 96%, 97%, 98% or 99% identity to the polynucleotides depicted in SEQ ID NOS:3 or 4 as well as the polynucleotides in reverse sense orientation, or the polynucleotide sequences encoding the human carboxypeptidase M or human mouse double minute 2 homolog polypeptides depicted in SEQ ID NOS:1 or 2 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 3 or 4. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The term "variant" also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "variant" also encompasses naturally occurring variants such as single nucleotide polymorphisms (SNPs).

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human carboxypeptidase M or human mouse double minute 2 homolog genes. These include but are not limited to an expression control element, an intron, a 5'-non-coding region, a 3'-non-coding region and splice junctions (see Tables 1-2, as well as transcription factor binding sites (see Table 3). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600, 2000 or about 5000 nucleotides in length may be used.

Table 1. Exon/Intron Organization of the Human Carboxypeptidase M Gene (cDNA Accession No. XM__006768) in SEQ ID NO: 3, 99680 Base Pairs; Nucleotides 1-99680 in the Genomic Clone of Accession No. AC025423 (Forward Strand Coding).

TABLE 1

EXON/INTRON ORGANIZATION OF THE HUMAN CARBOXYPEPTIDASE M GENE (cDNA ACCESSION NO. XM__006768) IN SEQ ID NO: 3, 99680 BASE PAIRS; NUCLEOTIDES 1-99680 IN THE GENOMIC CLONE OF ACCESSION NO. AC025423 (FORWARD STRAND CODING).

| EXON | NUCLEOTIDE NO. | AMINO ACID NO. |
|---|---|---|
| 1 | 16641-16796 | 1-52 |
| 2 | 63585-63686 | 53-86 |
| 3 | 77522-77692 | 87-143 |
| 4 | 79077-79262 | 144-205 |
| 5 | 79982-80152 | 206-262 |
| 6 | 82429-82581 | 263-313 |
| 7 | 90406-90555 | 314-363 |
| 8 | 92799-93038 | 364-443 |
| STOP CODON | 93039-93041 | |

Table 2. Exon/Intron Organization of the Human Mouse Double Minute 2 Homolog Gene (Variant of Accession No. NM__002392) in SEQ ID NO:4, 51039 Base Pairs; Nucleotides 99541-150579 in the Genomic Clone of Accession No. AC025423 (Reverse Strand Coding).

TABLE 2

EXON/INTRON ORGANIZATION OF THE HUMAN MOUSE DOUBLE MINUTE 2 HOMOLOG GENE (VARIANT OF ACCESSION NO. NM__002392) IN SEQ ID NO:4, 51039 BASE PAIRS; NUCLEOTIDES 99541-150579 IN THE GENOMIC CLONE OF ACCESSION NO. AC025423 (REVERSE STRAND CODING).

| EXON | NUCLEOTIDE NO. | AMINO ACID NO. |
|---|---|---|
| STOP CODON | 10089-10091 | |
| 10 | 10092-10664 | 491-301 |
| 9 | 13189-13266 | 300-275 |
| 8 | 13954-14109 | 274-223 |
| 7 | 21007-21168 | 222-169 |
| 6 | 25288-25383 | 168-137 |
| 5 | 25508-25576 | 136-114 |
| 4 | 29565-29615 | 113-97 |
| 3 | 32995-33126 | 96-53 |
| 2 | 36310-36384 | 52-28 |
| 1 | 40646-40726 | 27-1 |

Table 3: Transcription Factor Binding Sites on Genes that Encode Carboxypeptidase M (CpM) and the Human Homolog of Mouse Double Minute 2 (huMDM2)

TABLE 3

TRANSCRIPTION FACTOR BINDING SITES ON GENES THAT ENCODE CARBOXYPEPTIDASE M (Cpm) AND THE HUMAN HOMOLOG OF MOUSE DOUBLE MINUTE 2 (huMDm2)

| BINDING SITES | CpM | huMDM2 |
|---|---|---|
| AP1FJ__Q2 | 60 | 25 |
| AP1__C | 16 | 11 |
| AP1__Q2 | 39 | 13 |
| AP1__Q4 | 24 | 12 |
| AP4__Q5 | 47 | 27 |
| AP4__Q6 | 22 | 14 |
| ARNT__01 | | 4 |
| BRN2__01 | 29 | 6 |
| CAAT__01 | 7 | 4 |
| CDPCR3HD__01 | 19 | 7 |
| CEBPB__01 | 26 | 6 |
| CMYB__01 | 7 | |
| CREL__01 | 15 | 4 |
| DELTAEF1__01 | 196 | 98 |
| FREAC7__01 | 30 | 29 |
| GATA1__02 | 40 | 25 |
| GATA1__03 | 63 | 21 |
| GATA1__04 | 109 | 46 |

TABLE 3-continued

TRANSCRIPTION FACTOR BINDING SITES ON GENES THAT ENCODE CARBOXYPEPTIDASE M (Cpm) AND THE HUMAN HOMOLOG OF MOUSE DOUBLE MINUTE 2 (huMDm2)

| BINDING SITES | CpM | huMDM2 |
|---|---|---|
| GATA1_05 | 21 | 13 |
| GATA1_06 | 33 | 26 |
| GATA2_02 | 59 | 35 |
| GATA2_03 | 20 | 19 |
| GATA3_02 | 30 | 23 |
| GATA3_03 | 18 | 20 |
| GATA_C | 61 | 15 |
| GFII_01 | 23 | 8 |
| HFH2_01 | 20 | 13 |
| HFH3_01 | 32 | 13 |
| HFH8_01 | 23 | 7 |
| HNF3B_01 | 10 | 7 |
| IK1_01 | 12 | |
| IK2_01 | 216 | 63 |
| LMO2COM_01 | 86 | 23 |
| LMO2COM_02 | 85 | 23 |
| LYF1_01 | 45 | 41 |
| MAX_01 | 8 | 4 |
| MYCMAX_02 | 8 | |
| MYOD_01 | 5 | |
| MYOD_Q6 | 49 | 21 |
| MZF1_01 | 187 | 61 |
| NF1_Q6 | 10 | 5 |
| NFAT_Q6 | 134 | 71 |
| NFY_Q6 | 16 | |
| NKX25_01 | 48 | 35 |
| NKX25_02 | 30 | 9 |
| NMYC_01 | 16 | 10 |
| OCT1_01 | 3 | |
| OCT1_02 | 6 | |
| OCT1_06 | 3 | |
| OCT1_07 | 5 | |
| OCT1_Q6 | 5 | |
| RORA1_01 | 8 | 9 |
| S8_01 | 183 | 128 |
| SOX5_01 | 76 | 29 |
| SRY_02 | 38 | 27 |
| STAT_01 | 11 | |
| TATA_01 | 28 | 22 |
| TATA_C | 20 | 8 |
| TCF11_01 | 182 | 51 |
| USF_01 | 16 | 10 |
| USF_C | 16 | 10 |
| VMYB_02 | 7 | 11 |
| XFD2_01 | 11 | 8 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 12 genomic clone of accession number AC025423 has been discovered to contain the human carboxypeptidase M gene and the human mouse double minute 2 homolog gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC025423 was compared to the human carboxypeptidase M cDNA sequence, accession number XM_006768 and the human mouse double minute 2 homolog cDNA sequence accession number NM_002392, one of several splice variants.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human carboxypeptidase M gene or the human mouse double minute 2 homolog gene may be accomplished in a number of ways. For example, if an amount of a portion of a human carboxypeptidase M gene or the human mouse double minute 2 homolog gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 15 and preferably 40, nucleotide fragment of the sequences depicted in SEQ ID NOS:3 or 4. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human carboxypeptidase M or human mouse double minute 2 homolog polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:3 or 4 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human carboxypeptidase M or human mouse double minute 2 homolog polypeptide.

A gene encoding human carboxypeptidase M or human mouse double minute 2 homolog polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human carboxypeptidase M gene (nucleotides 1-99680 of SEQ ID NO:3) or human mouse double minute 2 homolog gene (nucleotides 1-51039 of SEQ ID NO:4) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 3 or 4 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (VIIIa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C(CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5Ô-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM§1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, carboxypeptidase M activity can be determined by measuring the release of the C-terminal arginine of bradykinin or a synthetic acyl-dipeptide such as benzoyl-Ala-Arg. The human homolog of mouse double minute 2 may be detected by its ability to bind p53.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human carboxypeptidase M or human mouse double minute 2 homolog polypeptides produced according to the method of the present invention may be used as an immunogen to generate any of these antibodies. Such antibodies include but are not limited to polyclonal, monoclonal, chimeric, single chain, Fab fragments, and a Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the human carboxypeptidase M or human mouse double minute 2 homolog polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human carboxypeptidase M or human mouse double minute 2 homolog polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human carboxypeptidase M or human mouse double minute 2 homolog polypeptide.

Antibody fragments that contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments for hybridizing to non-coding regions of SEQ ID NOS:3 or 4 may be attached to a substrate or reverse complements of said fragments. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides hybridizing to a non coding region of SEQ ID NO:3 or 4. Alternatively the microarray may comprise a polynucleotide(s) hybridizing to said non-coding region and/or coding regions of SEQ ID NO:3 or 4.

Uses of Polynucleotides

Diagnostics

Polynucleotide fragments containing noncoding regions of SEQ ID NO:3 or 4 may be used as probes for detecting variants from genomic nucleotide samples from a patient. The variants may be allelic variants or substitution, insertion or deletion nucleotide variants. Genomic DNA may be isolated from the patient. Alternatively the polynucleotide fragments may be used to monitor expression of SEQ ID NO:3 or 4 from samples from a patient. A mutation(s) may be detected by Southern blot analysis, for example, by hybridizing restriction digested genomic DNA to various probes between 10-500 nucleotides in length, preferably between 20-200 nucleotides in length, more preferably between 20-100 nucleotides in length and most preferably between 20-50 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998)). Single base extension (see, for example, U.S. Pat. No. 6,004,744) may be used to detect SNPs. Additionally, primers may be obtained by routine or long range PCR that yield products containing contiguous intron(s)/exon sequence(s) and products containing more than one exon with intervening intron(s). The sequence of the amplified genomic DNA from the patient may be determined using methods known in the art. Such probes may be between 20-5000 nucleotides in length and may preferably be between 20-50 nucleotides in length.

Thus the invention is directed to kits comprising these polynucleotide probes. In a specific embodiment, these probes are labeled with a detectable substance.

In one embodiment, the probes are in solution. In another embodiment, the probes are attached to a substrate. In a specific embodiment, the probes are contained within a microarray and are separately detectable.

The probes or primers of the present invention could be used to identify patients with or having a propensity for sepsis (SEQ ID NO:3—carboxypeptidase M gene) or for sarcoma or leukemias (SEQ ID NO:4—human mouse double minute 2 homolog gene).

Antisense Oligonucleotides and Mimetics

The antisense or reverse complement oligonucleotides or mimetics of the present invention may be used to decrease levels of a polypeptide. For example, human carboxypeptidase M has been found to form des-Arg9-bradykinin, an agonist of the B1 receptor activated by sepsis. Therefore, the human carboxypeptidase M antisense oligonucleotides of the present invention could be used to inhibit formation of des-Arg9-bradykinin. Human mouse double minute 2 homolog antisense sequences may be used to treat sarcomas and leukemias in which the gene is over-expressed.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human carboxypeptidase M modulates actions of anaphylatoxins and kinins and human mouse double minute 2 homolog plays a role in cell proliferation. Therefore, the human carboxypeptidase M gene may be used to modulate or prevent complement-linked tissue damage, in subjects in need thereof, for example, those exhibiting allergic reactions to a given substance. The human mouse double minute 2 homolog gene may be used to stimulate cell proliferation in subjects in need thereof, for example, for wound healing and those suffering from neurodegenerative or neuromuscular diseases, ischemic stroke, anoxia, ischemia/reperfusion damage and intoxication septic shock.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propy 1]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Feigner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4_spermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid molecule 20-51039 contiguous nucleotides in length consisting of a reverse or forward strand of a region of SEQ ID NO:4, wherein said region is selected from the group consisting of a 5'-non coding region between nucleotides 51039-41739 of SEQ ID 4; a 3'-non-coding region between nucleotides 9503-1 of SEQ ID NO:4; a contiguous intron-exon region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; a contiguous exon-intron region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; an intron depicted in nucleotides 36385-40645, 36309-33127, 32994-29616, 29564-25577, 25507-25384, 25287-21169, 21006-14110, 13953-13267, and/or 13188-10665; a region comprising a dinucleotide of the following group: 41739-41738, 40645-40646, 36309-36310, 36384-36385, 32994-32995, 33126-33127, 29564-29565, 29615-29616, 25507-25508, 25287-25288, 25383-25384, 25576-25577, 21006-21007, 21168-21169, 14109-14110, 13953-13954, 13266-13267, 13188-13189, 10664-10665 and/or 9504-9503; a transcription binding site selected from the group consisting of

| BINDING SITES | huMDM2, location in SEQ ID NO:4 |
|---|---|
| AP1__C: | 36-46, 2876-2886; |
| AP4__Q5: | 7944-7980; |
| AP4__Q6: | 7943-59, 8924-8940, 9294-9310; |
| ARNT__01: | 1682-1706, 2193-2217, 9201-9225; |
| BRN2__01: | 1040-1058,7803-7821; |
| CAAT__01: | 3292-3306; |
| CDPCR3HD__01: | 6522-6540; |
| CEBPB__01: | 1424-1438, 3917-3931, 4178-4192,4787-4801, 6855-6869; |
| CREL__01: | 5630-5642; |
| DELTAEF1__01: | 83-95, 6328-6340; |
| FREAC7__01: | 2757-2773, 5154-5170, 5823-5839; |
| GATA1__04: | 4846-4858, 7017-7029; |
| GATA1__05: | 8464-8476; |
| GATA2__02: | 6045-6057, 6073-6085, 6142-6154; |
| GATA2__03: | 2489-2501, 3323-3335, 3384-3396, 7393-7405: |
| GATA3__02: | 3264-3276, 6870-6882: |
| GATA3__03: | 40-52, 5729-5741, 6529-6541, 6874-6886, 7041-7053, 7589-7601; |
| GATA__C: | 7349-7361, 8188-8200; |
| HFH2__01: | 1743-1759, 7995-8011; |
| HFH3__01: | 502-518, 1739-1755, 4160-4176, 9402-9418, 9418-9434; |
| HFH8__01: | 8184-8200; |
| IK2__01: | 951-963, 3588-3600; |
| MZF1__01: | 1202-1210, 1447-1455, 4997-4005, 5424-5432; |
| NF1__Q6: | 1480-1500, 8166-8182; |
| NFAT__Q6: | 4190-4208, 6009-6027; |

-continued

| BINDING SITES | huMDM2, location in SEQ ID NO:4 |
|---|---|
| NKX25_01: | 741-755, 1648-1662, 1885-1899, 1984-1998, 3609-3623,4928-4942, 5060-5074, 5889-5903, 8850-8864, 9190-9204; |
| NKX25_02: | 2584-2599, 2970-2984, 4644-4658, 5179-5193, 6482-6496; |
| NMYC_01: | 2560-2572; |
| RORA1_01: | 220-238, 2638-2656; |
| S8_01: | 4644-4656, 4842-4854, 4845-4857, 5200-5212, 5371-5383, 5735-5747, 6482-6494, 6541-6553, 6544-6556, 6772-6784, 7270-7292, 7273-7285; |
| SOX5_01: | 1355-1371, 1430-1446, 3094-3110, 3155-3171, 4669-4685, 4692-4708, 4789-4805; |
| SRY_02: | 4164-4180, 5665-5681; |
| TATA_01: | 1261-1277, 2574-2590, 2723-2739, 2733-2749, 2770-2786, 4199-4215, 4206-4222; |
| TATA_C: | 5900-5916, 7456-7472, 7702-7718, 7917-7933; and |
| XFD2_01: | 7702-7218,7917-7933; |

a transcription binding site selected from the group consisting of

| BINDING SITES | huMDM2, location in SEQ ID NO:4 |
|---|---|
| AP1_C: | 12109-12119, 12695-12705, 22600-22610, 24166-24176, 31311-31321, 35234-35244, 39184-39194; |
| AP1_Q2: | 11952-11962, 12068-12078, 14798-14808, 21748-21758, 22613-22623, 23676-23686, 26562-26572, 30046-30056; |
| AP1_Q4: | 12695-12705, 31311-31321, 35234-35244, 36295-36305, 38784-38794, 39188-39198; |
| AP4_Q6: | 31635-31651; |
| BRN2_01: | 13448-13466, 14764-14782, 28094-28112, 40027-40045; |
| CAAT_01: | 11288-11302, 15054-15068; |
| CDPCR3HD_01: | 11286-11304, 13284-13302, 20846-20864, 29344-29362; |
| CEBPB_01: | 29241-29255; |
| CREL_01: | 36091-36103, 38873-38885; |
| DELTAEF1_01: | 18083-18095, 20385-20397, 26955-26967; |
| FREAC7_01: | 11982-11998, 15187-15202, 16523-16539, 16529-16545, 16587-16603, 16604-16620, 16676-16642, 16633-16649, 16644-16660, 16650-16666, 16657-16673, 16673-16689, 16762-16778, 21332-21348, 25689-25700, 26529-26545, 27767-27783, 29495-29511; |
| GATA1_02: | 10916-10928, 15775-15789, 18162-18174, 26088-26100, 32518-32530; |
| GATA1_03: | 28012-28024; |
| GATA1_04: | 11153-11165, 11630-11642, 13778-13790, 17439-17451, 19300-19312, 21606-21618, 22743-22755, 23747-23759, 25806-25818, 26529-26541, 29424-29436, 30455-30467, 32761-32778, 33352-33364, 33960-33972, 36101-36113, 40007-40019; |
| GATA1_05: | 11590-11602, 26550-26562, 36737-36749; |
| GATA1_06: | 18772-18784, 23054-23066, 35568-35580, 37855-37867; |
| GATA2_02: | 20755-20767, 30830-30842, 34755-34767, 36285-36297, 39143-39155, 39641-39653, 40586-40598; |
| GATA2_03: | 13535-13547, 22711-22723, 23161-23173, 25028-25040, 27237-27249, 36277-36289; |
| GATA3_02: | 11558-11570, 16470-16482, 17225-17237, 19619-19631, 22156-22168, 22443-22455, 24713-24725, 27619-27631, 32716-32728, 34124-34136, 34163-34175, 36832-36844, 38403-38415; |
| GATA3_03: | 10869-10881, 11515-11527, 13845-13857, 17221-17233, 18952-18964, 20050-20062, 40171-40183; |
| GATA_C: | 15848-15860, 18899-18911, 23640-23652, 29072-29084, 30881-30893, 33198-33210, 37472-37484, 38621-38633; |
| GFI1_01: | 35469-35481, 35492-35504; |
| HFH2_01: | 15939-15955, 24636-24652, 25866-25882, 32171-32187, 35372-35388, 39457-35473; |
| HFH3_01: | 13340-13356, 19218-19234, 21328-21344, 21336-21352, 21344-21360, 28062-28078, 32125-32141; |
| HFH8_01: | 14133-14149, 22578-22584; |
| HNF3B_01: | 13150-13166, 16505-16521, 25264-25280, 29443-29459, 37654-37670; |
| IK2_01: | 11547-11559, 17144-17156, 18961-18973, 23883-23895, 27617-27629, 28908-28920, 29241-29253, 30752-30764, 34768-34780; |
| LYF1_01: | 12319-12331, 19191-19203, 37226-37238, 39430-39442; |
| MAX_01: | 22974-22986, 33339-33351; |
| MZF1_01: | 26105-26113, 35187-35195; |
| NF1_Q6: | 12048-12064, 33334-33354; |
| NFAT_Q6: | 13295-13313, 14157-14175, 14311-14329, 14414-14432, 18269-18287, 19326-19344, 20801-20819, 21177-21195, 22537-22555, 23861-23879, 25392-25410, 25879-25897, 27524-27542, 30636-30654, 30718-30736, 31525-31543, 33655-33673, 34726-34744, 34917-34535, 34990-35008, 35979-35997, 36479-36493, 36577-36595, 37154-37172, 40224-40242, 40365-40383; |
| NKX25_01: | 12041-12055, 12340-12354, 12471-12485, 12742-12756, 12877-12891, 13849-13863, 18995-19009, 21440-21454, 21883-21897, 28426-28440, 30964-30978, 32033-32047, 32265-32279; |
| NKX25_02: | 10998-11012, 12711-12725, 14131-14145, 14726-14740, 16024-16038; |
| NMYC_01: | 18753-18765, 18754-18766, 23076-23088, 30534-30546, 34400-34412; |
| RORA1_01: | 13134-13152, 22966-22984, 24934-24952, 33341-33359, 34760-34778; |
| S8_01: | 11000-11012, 11977-11989, 12048-12060, 12051-12063, 13747-13759, 13923-13935, 13926-13938, 14676-14688, 14679-14691, 16026-16038, 16313-16325, 16316-16328, 17515-17527, 20756-20768, 20759-20771, 23154-23166, 23157-23169, 25198-25210, 25201-25213, 26651-26663, 27508-27520, 27511-27523, 29450-29462, 29478-28490, 29775-29787, 29778-29790, 29813-29825, 29816-29828, 31329-31341, 31677-31689, 31680-31692, 31732-31744, 31735-31747, 36137-36149, 36140-36152, 36812-36824, 36815-36827, 37413-37425, 38679-38691, 39474-39486, 39477-39489; |
| SOX5_01: | 27397-27413, 27572-27588, 28100-28116, 29230-29246, 29439-29455, 30690-30706, 31595-31611, 33871-33887, 34113-34129, 34624-34640, 37668-37684, 38582-38598, 39124-39140, 40410-40426; |
| SRY_02: | 20016-20032, 22410-22426, 27329-27345, 29162-29178, 29499-29515, 30646-30662, 31503-31519, 35928-35944, 37324-37340; |
| TATA_01: | 32722-32738, 32729-32745, 32807-32823, 33825-33841, 34120-34136, 35433-35449, 36593-36609; |
| TATA_C: | 11015-11031, 11817-11833, 13635-13651, 14930-14946; |
| TCF11_01: | 18543-18549, 22574-22580, 31281-31297, 31489-31505, 38754-38770; |
| USF_01: | 23075-23087, 32577-32589; |
| VMYB_02: | 11526-11538, 17384-17396, 18400-18412, 19549-19561, 22188-22200, 40486-40508 and |
| XFD2_01: | 16620-16636, 18153-18169, 22102-22118, 23141-23157; |

And a transcription binding site selected from the group consisting of

| BINDING SITES | huMDM2, 1 location in SEQ ID NO:4 |
|---|---|
| AP1_C: | 44584-44594, 49069-49079: |
| AP1_Q2: | 42174-42184, 45217-45227, 48422-48422, 50447-50457; |
| AP1_Q4: | 42702-42712, 50806-50816; |
| AP4_Q6: | 42117-42133, 42118-42134, 42244-42260, 45432-45448; 45433-45449, 46609-46625; |

-continued

| BINDING SITES | huMDM2, 1 location in SEQ ID NO:4 |
|---|---|
| BRN2_01: | 42310-42328, 44022-44040, 47514-47532, 48900-48918, 48967-48985; |
| CAAT_01: | 44866-44880; |
| CDPCR3HD_01: | 45671-45689, 49219-49237; |
| CREL_01: | 42437-42449, 49797-49809; |
| FREAC7_01: | 47026-47042, 47292-47308, 47658-47674; |
| GATA1_02: | 43482-43494, 48926-48938, 49284-49296; |
| GATA1_03: | 47371-47383; |
| GATA1_04: | 43054-43066, 43162-43162, 43967-43979, 45464-45476, 45916-45928, 47763-47775; |
| GATA1_05: | 49319-49331, 49459-49471; |
| GATA1_06: | 47590-47602; |
| GATA2_02: | 42660-42672, 43475-43487; |
| GATA2_03: | 43714-43726, 50948-50960; |
| GATA3_02: | 49155-49167, 49844-49856; |
| GATA3_03: | 42202-42214, 44810-44822, 48438-48450, 49136-49148, 49337-49349, 49869-49881; |
| GATA_C: | 44011-44023, 45256-45268, 45823-45835, 47915-47927, 49201-49213, 49573-49585; |
| GFI1_01: | 46606-46618, 47063-47075; |
| HFH3_01: | 47030-47046, 47284-47300, 47288-47304; |
| IK2_01: | 45275-45287; |
| LYF1_01: | 44564-44576, 46991-47003, 49567-49579; |
| MAX_01: | 43234-43246, 48726-48738; |
| MZF1_01: | 41772-41780, 42290-42298, 42295-42303, 44507-44515, 45105-45113, 45203-45211, 49948-49956, 50774-50782; |
| NF1_Q6: | 50209-50229; |
| NFAT_Q6: | 42061-42079, 44418-44436, 46399-46417, 47974-47992, 49267-49285, 49964-49982, 50392-50410; |
| NKX25_01: | 42394-42408, 43507-43521, 46115-46129; |
| RORA1_01: | 45073-45091, 48718-48736; |
| S8_01: | 43552-43564, 45214-45226, 47160-47172, 48419-48431, 49295-49307, 50379-50391; |
| SOX5_01: | 43716-43732, 46351-46367, 47156-47172, 47774-47790, 47868-47884, 47974-47990, 48915-48931, 50323-50339; |
| TATA_01: | 45588-45604, 47625-47641, 48026-48042, 48659-48675, 49056-49072, 49079-49095, 49152-49168; |
| TCF11_01: | 49115-49131; |
| VMYB_02: | 42010-42022, 42279-42291, 44651-44663; and |
| XFD2_01: | 42870-42886, 42910-42926. |

2. A composition comprising the nucleic acid molecule of claim 1 and a carrier.

3. A kit comprising the nucleic acid molecule of claim 1.

4. The kit according to claim 3, in which the nucleic acid molecule is labeled with a detectable substance.

5. A solid support comprising the nucleic acid molecule of claim 1.

6. The solid support of claim 5 wherein said support is a microarray.

7. The solid support of claim 6, which further comprises a nucleic acid molecule encoding human mouse double minute 2 homolog, complementary sequence thereof or a portion of said nucleic acid molecule containing at least 20 contiguous nucleotides.

8. A method for detecting the presence or absence of SEQ ID NO:4 or its fully complementary sequence in a sample, said method comprising (a) contacting the sample with the nucleic acid molecule of claim 1 and (b) determining whether the nucleic acid molecule binds to said nucleic acid sequence in the sample.

9. An isolated nucleic acid molecule 20-5000 contiguous nucleotides in length consisting of a reverse or forward strand of a contiguous exon-intron region between nucleotides 41738-9502 of SEQ ID NO:4 or a contiguous intron-exon region between nucleotides 41738-9502 of SEQ ID NO:4, wherein a sequence segment between 41738-9502 of SEQ ID NO:4 encodes human mouse double minute 2 homolog depicted in SEQ ID NO:2.

10. The isolated nucleic acid molecule of claim 9, wherein said nucleic acid molecule is 20-5000 contiguous nucleotides in length and comprises nucleotides 41739-41738, 40645-40646, 36309-36310, 36384-36385, 32994-32995, 33126-33127, 29564-29565, 29615-29616, 25507-25508, 25287-25288, 25383-25384, 25576-25577, 21006-21007, 21168-21169, 13953-13954, 14109-14110, 13188-13189, 13266-13267, 10664-10665 and/or 9504-9503 of SEQ ID NO:4 or their reverse strands.

11. A microarray comprising a plurality of the nucleic acid molecules of claim 1.

12. The microarray of claim 11 wherein said microarray further comprises a nucleic acid molecule encoding human mouse double minute 2 homolog, complementary sequence thereof or a portion of said nucleic acid molecule containing at least 20 contiguous nucleotides.

13. A method for detecting the nucleic acid molecule of claim 1 in a sample comprising (a) amplifying said nucleic acid molecule and (b) detecting the presence of the amplified nucleic acid molecule of (a) wherein amplifying is carried out by polymerase chain reaction.

* * * * *